(12) United States Patent
Ahmed et al.

(10) Patent No.: US 9,303,035 B2
(45) Date of Patent: Apr. 5, 2016

(54) SUBSTITUTED PYRAZINO[1',2':1,2]PYRROLO[3,4-D]PYRIMIDINES, PYRIMIDO[4',5':3,4]PYRROLO[2,1-C][1,4]OXAZINES AND PYRIMIDO[4',5':3,4]PYRROLO[1,2-D][1,4]OXAZEPINES FOR INHIBITING THE CFTR CHANNEL

(71) Applicants: Mahbub Ahmed, Horsham (GB); Alexander Ashall-Kelly, London (GB); Graham Charles Bloomfield, Horsham (GB); Louisa Gueritz, London (GB); Jeffrey McKenna, Horsham (GB); Joseph McKenna, Hove (GB); Simon Mutton, Guildford (GB); Rakesh Parmar, Hove (GB); Jon Sheperd, Horsham (GB); Paul Wright, Ashtead (GB)

(72) Inventors: Mahbub Ahmed, Horsham (GB); Alexander Ashall-Kelly, London (GB); Graham Charles Bloomfield, Horsham (GB); Louisa Gueritz, London (GB); Jeffrey McKenna, Horsham (GB); Joseph McKenna, Hove (GB); Simon Mutton, Guildford (GB); Rakesh Parmar, Hove (GB); Jon Sheperd, Horsham (GB); Paul Wright, Ashtead (GB)

(73) Assignee: Novartis AG, Basel (CH)

( * ) Notice: Subject to any disclaimer, the term of this patent is extended or adjusted under 35 U.S.C. 154(b) by 223 days.

(21) Appl. No.: 14/109,927

(22) Filed: Dec. 17, 2013

(65) Prior Publication Data
US 2014/0171412 A1 Jun. 19, 2014

Related U.S. Application Data

(60) Provisional application No. 61/906,154, filed on Nov. 19, 2013, provisional application No. 61/739,337, filed on Dec. 19, 2012.

(51) Int. Cl.
| | |
|---|---|
| *A61K 31/519* | (2006.01) |
| *C07D 239/70* | (2006.01) |
| *C07D 487/14* | (2006.01) |
| *A61K 31/5383* | (2006.01) |
| *A61K 31/553* | (2006.01) |
| *A61K 45/06* | (2006.01) |
| *C07D 498/14* | (2006.01) |

(52) U.S. Cl.
CPC ............ *C07D 487/14* (2013.01); *A61K 31/519* (2013.01); *A61K 31/5383* (2013.01); *A61K 31/553* (2013.01); *A61K 45/06* (2013.01); *C07D 498/14* (2013.01)

(58) Field of Classification Search
CPC ............................ A61K 31/519; C07D 239/70

USPC ........ 514/267; 544/250, 251; 548/202, 373.1; 549/59, 505
See application file for complete search history.

(56) References Cited

U.S. PATENT DOCUMENTS

| | | | |
|---|---|---|---|
| 2009/0163545 | A1 | 6/2009 | Goldfarb et al. |
| 2014/0171412 | A1 | 6/2014 | Mahbub et al. |
| 2014/0171417 | A1 | 6/2014 | Mahbub et al. |

FOREIGN PATENT DOCUMENTS

| | | |
|---|---|---|
| JP | 2002-255967 A | 9/2002 |
| WO | 01-14386 A1 | 3/2001 |
| WO | 2008/073365 A1 | 6/2008 |
| WO | 2011/019737 A1 | 2/2011 |
| WO | 2012/166658 A1 | 12/2012 |

OTHER PUBLICATIONS

Carosati et al., Ligand-based virtual screening and ADME-tox guided approach to identify triazolo-quinoxalines as folate cycle inhibitors. Bioorg Med Chem. Nov. 15, 2010;18(22):7773-85. Epub Oct. 1, 2010.

Lee et al., Development of improved inhibitors of wall teichoic acid biosynthesis with potent activity against Staphylococcus aureus. Bioorg Med Chem Lett. Mar. 1, 2010;20(5):1767-70. Epub Jan. 20, 2010.

Snyder et al., Absolute Configuration and Biological Properties of Enantiomers of CFTR Inhibitor BPO-27. ACS Med Chem Lett. May 9, 2013;4(5):456-459.

Snyder et al., Potent, metabolically stable benzopyrimido-pyrrolo-oxazine-dione (BPO) CFTR inhibitors for polycystic kidney disease. J Med Chem. Aug. 11, 2011;54(15):5468-77. Epub Jul. 12, 2011.

Tanifum et al., Novel pyridopyrimidine derivatives as inhibitors of stable toxin a (STa) induced cGMP synthesis. Bioorg Med Chem Lett. Jun. 1, 2009;19(11):3067-71. Epub Apr. 12, 2009.

Toropov et al., QSAR models for inhibitors of physiological impact of *Escherichia coli* that leads to diarrhea. Biochem Biophys Res Commun. Mar. 8, 2013;432(2):214-25. Epub Feb. 10, 2013.

(Continued)

*Primary Examiner* — Douglas M Willis
(74) *Attorney, Agent, or Firm* — Jing Grace Sun

(57) ABSTRACT

The present invention provides a compound of formula I or a pharmaceutically acceptable salt thereof;

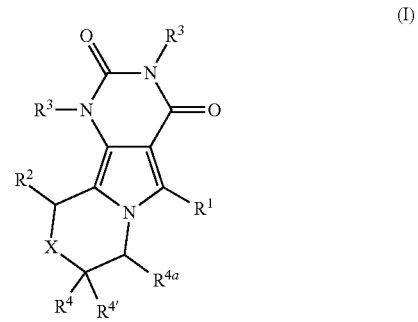

and its therapeutic uses. The present invention further provides a combination of pharmacologically active agents and a pharmaceutical composition.

22 Claims, No Drawings

(56) References Cited

OTHER PUBLICATIONS

Tradtrantip et al., Nanomolar potency pyrimido-pyrrolo-quinoxalinedione CFTR inhibitor reduces cyst size in a polycystic kidney disease model. J Med Chem. Oct. 22, 2009;52(20):6447-55.

Tsupak et al., [3,4] Annulated pyrroles 1. Polynuclear heterocyclic systems based on pyrrolo[3,4 d]pyrimidine 2,4 dione. Russian Chemical Bulletin. 2006;55(12):2265-70.

Tsupak et al., Pyrrolopyrimidines. 5. Reaction of 6-Amino-1,3-Dimethylpyrrolo[3,4-d]Pyrimidine-2,4(1H,3H)-Diones With 1,3-Diketones. Chemistry of Heterocyclic Compounds. 2003;39(7):953-9.

Wetzel et al., A scaffold-tree-merging strategy for prospective bioactivity annotation of gamma-pyrones. Angew Chem Int Ed Engl. May 10, 2010;49(21):3666-70.

SUBSTITUTED PYRAZINO[1',2':1,2] PYRROLO[3,4-D]PYRIMIDINES, PYRIMIDO[4',5':3,4]PYRROLO [2,1-C][1,4]OXAZINES AND PYRIMIDO[4',5':3,4] PYRROLO[1,2-D][1,4]OXAZEPINES FOR INHIBITING THE CFTR CHANNEL

FIELD OF THE INVENTION

The invention provides tricyclic compounds, the use thereof for inhibiting the CFTR channel and methods of treating disease using same.

BACKGROUND OF THE INVENTION

The cystic fibrosis transmembrane conductance regulator protein (CFTR) is a cAMP-activated chloride channel which is expressed in epithelial cells in mammalian airways, intestine, pancreas, and testis (Sheppard et al., *Physiol. Rev.* 79:S23-45 (1999); Gadsby et al., *Nature* 40:477-83 (2006)). The CFTR chloride channel is known to be associated with a number of diseases and conditions, including cystic fibrosis (CF), polycystic kidney disease and secretory diarrhea.

Diarrheal disease remains an area of high unmet medical need, resulting in approximately 2 million deaths in 2002, of which more than 95% were children under the age of 5 years. Infectious secretory diarrhea, the result of poor sanitation and close living conditions, is responsible for most acute episodes and there is a defined need for an adjunct therapy to be used in combination with existing oral rehydration and antibiotic therapies.

CFTR inhibitors are discussed by Thiagarajah and Verkman in Clinical Pharmacology and Therapeutics (2012): 92, 3, 287-290.

SUMMARY OF THE INVENTION

There is a need to provide new CFTR inhibitors that are good drug candidates. In particular, compounds of the invention should bind potently to the cystic fibrosis transmembrane conductance regulator protein whilst showing little affinity for other receptors and show functional activity as CFTR inhibitors. They should be well absorbed from the gastrointestinal tract, be metabolically stable and possess favourable pharmacokinetic properties. Furthermore, the ideal drug candidate will exist in a physical form that is stable, non-hygroscopic and easily formulated.

The compounds of the invention are high affinity inhibitors of the CFTR channel and are therefore potentially useful in the treatment of a wide range of disorders, particularly polycystic kidney disease and diarrhea (including infectious secretory diarrhea, travellers diarrhea, diarrhea associated with HIV and diarrhea predominant irritable bowel syndrome (IBS)).

The treatment of polycystic kidney disease and diarrhea is a contemplated use. All forms of polycystic kidney disease and diarrhea are potentially treatable with the compounds of the present invention including infectious secretory diarrhea, travellers diarrhea, diarrhea associated with HIV and diarrhea predominant irritable bowel syndrome (IBS).

The invention therefore provides, as Embodiment 1, a compound of formula (I), or a pharmaceutically acceptable salt thereof:

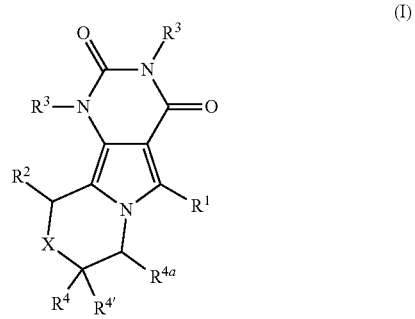

wherein $R^1$ represents phenyl, $(C_4-C_7)$cycloalkenyl or $Het^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1-C_4)$alkyl, halo, halo$(C_1-C_4)$alkyl, cyano, hydroxy$(C_1-C_4)$alkyl, $(C_1-C_4)$alkoxy, halo$(C_1-C_4)$alkoxy, $(C_1-C_4)$alkoxy$(C_1-C_4)$alkyl-, $R^6OC(O)$—, or $R^6OC(O)(C_1-C_4)$alkyl-;

$R^{a1}$ represents $(C_1-C_4)$alkyl, hydroxy$(C_1-C_4)$alkyl, $(C_1-C_4)$alkoxy$(C_1-C_4)$alkyl-, $(C_1-C_4)$alkylamino$(C_1-C_4)$alkyl-, di[$(C_1-C_4)$alkyl]amino$(C_1-C_4)$alkyl-, aryl$(C_1-C_4)$alkyl- or $R^6OC(O)(C_1-C_4)$alkyl-;

$R^2$ represents $(C_1-C_6)$alkyl, $(C_3-C_7)$cycloalkyl, $(C_4-C_7)$cycloalkenyl, phenyl, furanyl, thiazolyl, thienyl or pyrazolyl, which $R^2$ may be unsubstituted or substituted on from one to three carbon atoms with substituents $R^b$, and may further be substituted on a nitrogen atom with $(C_1-C_4)$alkyl;

each $R^b$ independently represents $(C_1-C_4)$alkyl, halo, halo$(C_1-C_4)$alkyl, cyano, $(C_1-C_4)$alkylamino$(C_1-C_4)$alkyl-, di[$(C_1-C_4)$alkyl]amino$(C_1-C_4)$alkyl-, $(R^6)_2NC(O)(C_1-C_4)$alkyl- or $R^6OC(O)(C_1-C_4)$alkyl-;

X represents O, NH or NMe; or

X represents —$CH_2$—O—, wherein the O atom is attached to the —$C(R^4)(R^{4'})$ atom of the ring;

each $R^3$ independently represents methyl or ethyl;

$R^4$ represents hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, phenyl, $Het^1(C_1-C_4)$alkyl-, $Het^2(C_1-C_4)$alkyl-, $(C_1-C_4)$alkylS(O)_2NH(C_1-C_4)$alkyl-, or $R^7C(O)NH(C_1-C_4)$alkyl-;

$R^{4'}$ represents H or methyl;

$R^{4a}$ represents hydrogen, $(C_1-C_4)$alkyl, halo$(C_1-C_4)$alkyl, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, $Het^1(C_1-C_4)$alkyl-, $Het^2(C_1-C_4)$alkyl-, or $R^6OC(O)$—;

$R^6$ represents hydrogen, $(C_1-C_4)$alkyl;

$R^7$ represents $(C_1-C_2)$alkyl, $(C_1-C_2)$alkoxy, $(C_1-C_2)$alkoxy $(C_1-C_2)$alkyl or phenyl;

$Het^1$ represents a 5- or 6-membered heteroaryl ring comprising a) one oxygen or sulphur atom and optionally one or two nitrogen atoms; or b) from one to four nitrogen atoms; and $Het^2$ represents a 4- to 7-membered heterocyclic ring comprising a) 1 or 2 heteroatoms selected from N, O and S; or b) —C(O)— and 1 or 2 heteroatoms selected from N and O. In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof and one or more therapeutically active agent.

In another embodiment, the invention provides a method of modulating CFTR activity in a subject, wherein the method comprises administering to the subject a therapeutically effective amount of a compound according to the definition of formula (I), or a pharmaceutically acceptable salt thereof, or subformulae thereof.

In another embodiment, the invention provides a method of treating a disorder or disease selected from polycystic kidney disease and diarrhea, comprising administering to the subject a therapeutically effective amount of a compound according to the definition of formula (I), or a pharmaceutically acceptable salt thereof, or subformulae thereof.

DETAILED DESCRIPTION

The invention therefore provides a compound of the formula (I) as described hereinabove as Embodiment 1.

Unless specified otherwise, the term "compounds of the present invention" refers to compounds of formula (I) and formula (Ia), salts of the compound, hydrates or solvates of the compounds, as well as all stereoisomers (including diastereoisomers and enantiomers), tautomers and isotopically labeled compounds (including deuterium substitutions). Compounds of the present invention further comprise polymorphs of compounds of formula I and formula (Ia) and salts thereof.

For purposes of interpreting this specification, the following definitions will apply and whenever appropriate, terms used in the singular will also include the plural and vice versa.

As used herein, the term "$C_{1-6}$alkyl" refers to a fully saturated branched or unbranched hydrocarbon moiety having 1 to 6 carbon atoms. The terms "$C_{1-4}$alkyl" and "$C_{1-2}$alkyl" are to be construed accordingly. Representative examples of $C_{1-6}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, and n-heptyl.

As used herein, the term "halo$C_{1-6}$alkyl" refers to a $C_{1-6}$alkyl group as defined herein, wherein at least one of the hydrogen atoms is replaced by a halo atom. The halo$C_{1-6}$alkyl group can be monohalo$C_{1-6}$alkyl, dihalo$C_{1-6}$alkyl or polyhalo$C_{1-6}$alkyl including perhalo$C_{1-6}$alkyl. A monohalo$C_{1-6}$alkyl can have one iodo, bromo, chloro or fluoro within the alkyl group. Dihalo$C_{1-6}$alkyl and polyhalo$C_{1-6}$alkyl groups can have two or more of the same halo atoms or a combination of different halo groups within the alkyl. Typically the polyhalo$C_{1-6}$alkyl group contains up to 12, or 10, or 8, or 6, or 4, or 3, or 2 halo groups.

Non-limiting examples of halo$C_{1-6}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-6}$alkyl group refers to an $C_{1-6}$alkyl group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-6}$alkoxy" refers to $C_{1-6}$alkyl-O—, wherein $C_{1-6}$alkyl is defined herein above. Representative examples of $C_{1-1}$alkoxy include, but are not limited to, methoxy, ethoxy, propoxy, 2-propoxy, butoxy, tert-butoxy, pentyloxy, and hexyloxy.

As used herein, the term "$Het^2$" or "heterocyclic ring" refers to a saturated or unsaturated non-aromatic ring or ring system, which is a 4-, 5-, 6-, or 7-membered monocyclic ring comprising a) 1 or 2 heteroatoms selected from N, O and S; or b) —C(O)— and 1 or 2 heteroatoms selected from N and O. The heterocyclic group can be attached via a heteroatom or a carbon atom. Examples of heterocyclic rings include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, pyrrolidinonyl, oxazolidinonyl and thiomorpholine.

The term "$C_{3-7}$cycloalkyl" refers to a fully saturated or unsaturated monocyclic hydrocarbon group of 3-7 carbon atoms. Exemplary monocyclic hydrocarbon groups include, but are not limited to, cyclopropyl, cyclobutyl, cyclopentyl, cyclopentenyl, cyclohexyl and cyclohexenyl.

As used herein, the term "$Het^1$" or "heteroaryl ring" refers to an aromatic ring system, which is a 5- or 6-membered monocyclic ring comprising a) one oxygen or sulphur atom and optionally one or two nitrogen atoms; or b) from one to four nitrogen atoms. Typical Heteroaryl rings include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), and 4- or 5-(1,2,3-triazolyl), tetrazolyl, pyrimidinyl and pyridinyl.

As used herein, the term "halogen" or "halo" refers to fluoro, chloro, bromo, and iodo.

Various (enumerated) embodiments of the invention are described herein. It will be recognized that features specified in each embodiment may be combined with other specified features to provide further embodiments of the present invention.

Embodiment 2

A compound of formula (I), or a pharmaceutically acceptable salt thereof:

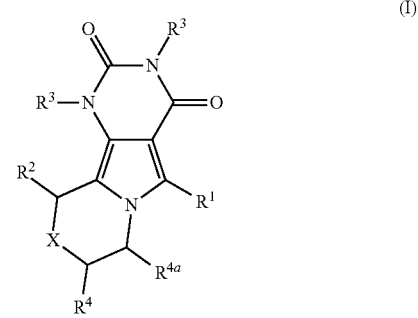

(I)

wherein $R^1$ represents phenyl, $(C_4\text{-}C_7)$cycloalkenyl or $Het^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1\text{-}C_4)$alkyl, halo, halo$(C_1\text{-}C_4)$alkyl, cyano, hydroxy$(C_1\text{-}C_4)$alkyl, $(C_1\text{-}C_4)$alkoxy, halo$(C_1\text{-}C_4)$alkoxy, $(C_1\text{-}C_4)$alkoxy$(C_1\text{-}C_4)$alkyl-, $R^6OC(O)$—, or $R^6OC(O)(C_1\text{-}C_4)$alkyl-;

$R^{a1}$ represents $(C_1\text{-}C_4)$alkyl, hydroxy$(C_1\text{-}C_4)$alkyl, $(C_1\text{-}C_4)$alkoxy$(C_1\text{-}C_4)$alkyl-, $(C_1\text{-}C_4)$alkylamino$(C_1\text{-}C_4)$alkyl-, di[$(C_1\text{-}C_4)$alkyl]amino$(C_1\text{-}C_4)$alkyl-, aryl$(C_1\text{-}C_4)$alkyl- or $R^6OC(O)(C_1\text{-}C_4)$alkyl-;

$R^2$ represents $(C_1-C_6)$alkyl, $(C_3-C_7)$cycloalkyl, $(C_4-C_7)$cycloalkenyl, phenyl, furanyl, thiazolyl, thienyl or pyrazolyl, which $R^2$ may be unsubstituted or substituted on from one to three carbon atoms with substituents $R^b$, and may further be substituted on a nitrogen atom with $(C_1-C_4)$alkyl;
each $R^b$ independently represents $(C_1-C_4)$alkyl, halo, halo$(C_1-C_4)$alkyl, cyano, $(C_1-C_4)$alkylamino$(C_1-C_4)$alkyl-, di[$(C_1-C_4)$alkyl]amino$(C_1-C_4)$alkyl-, $(R^6)_2$NC(O)$(C_1-C_4)$alkyl- or $R^6$OC(O)$(C_1-C_4)$alkyl-;
X represents O, NH or NMe;
each $R^3$ independently represents methyl or ethyl;
$R^4$ represents hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, or phenyl;
$R^{4a}$ represents hydrogen, $(C_1-C_4)$alkyl, halo$(C_1-C_4)$alkyl, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, Het$^2$$(C_1-C_4)$alkyl-, or $R^6$OC(O)—;
$R^6$ represents hydrogen, $(C_1-C_4)$alkyl;
Het$^1$ represents a 5- or 6-membered heteroaryl ring comprising a) one oxygen or sulphur atom and optionally one or two nitrogen atoms; or b) from one to four nitrogen atoms; and
Het$^2$ represents a 4- to 7-membered heterocyclic ring comprising 1 or 2 heteroatoms selected from N, O and S.

Embodiment 3

A compound according to Embodiment 1 or Embodiment 2, wherein X represents 0.

Embodiment 4

A compound according to any preceding claim, wherein $R^1$ represents phenyl, cyclohexenyl, thiazolyl, pyrazolyl, thienyl, pyrimidin-2-yl or pyridine-2-yl and wherein $R^1$ may be unsubstituted or substituted on one or two carbon atoms by substituents $R^a$, and may further be substituted on a nitrogen atom with a substituent $R^{a1}$.

Embodiment 5

A compound according to any preceding Embodiment, wherein $R^1$ represents thiazol-2-yl, thiazol-4-yl, thien-2-yl or pyrazol-4-yl, which $R^1$ group may be unsubstituted or substituted on one or two carbon atoms by substituents $R^a$, and may further be substituted on a nitrogen atom with a substituent $R^{a1}$ Embodiment 6

A compound according any preceding Embodiment, wherein $R^1$ represents phenyl, which may be unsubstituted or substituted by 1 or 2 substituents $R^a$.

Embodiment 7

A compound according to Embodiment 6, wherein the $R^a$ substituents are in the 3-position, 2- and 3-positions, 3- and 4-positions, 3- and 5-positions or 3- and 6-positions.

Embodiment 8

A compound according to any preceding Embodiment, wherein each $R^a$ independently represents $(C_1-C_4)$alkyl, halo, halo$(C_1-C_4)$alkyl, cyano, $(C_1-C_4)$alkoxy, $R^6$OC(O)—, or $R^6$OC(O)$(C_1-C_4)$alkyl-.

Embodiment 9

A compound according to any preceding Embodiment, wherein $R^2$ represents phenyl, furanyl, thiazolyl, thienyl or pyrazolyl, which $R^2$ may be unsubstituted or substituted on from one to three carbon atoms with substituents $R^b$, and may further be substituted on a nitrogen atom with $(C_1-C_4)$alkyl.

Embodiment 10

A compound according to any preceding Embodiment, wherein each $R^b$ independently represents $(C_1-C_2)$alkyl, halo, halo$(C_1-C_2)$alkyl, or cyano.

Embodiment 11

A compound according to any preceding Embodiment, wherein each $R^b$ independently represents methyl, ethyl, bromo, chloro, fluoro, trifluoromethyl, or cyano.

Embodiment 12

A compound according to any preceding Embodiment, wherein each $R^3$ represents methyl.

Embodiment 13

A compound according to any preceding Embodiment, wherein $R^4$ represents hydrogen, methyl, phenyl or HOCH$_2$—.

Embodiment 14

A compound according to any preceding Embodiment, wherein $R^{4a}$ represents hydrogen or methyl.

Embodiment 15

A compound according to any preceding Embodiment, wherein $R^6$ represents hydrogen, methyl or ethyl.

Embodiment 16

A compound according to any preceding Embodiment, wherein the compound is of formula (Ia):

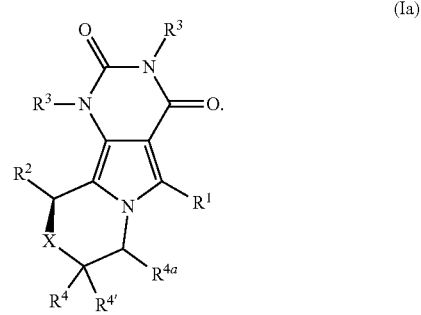

(Ia)

Embodiment 17

A compound according to any preceding Embodiment, wherein the compound of formula (I) is a racemate or has the stereochemistry as shown in formula (Ia).

Embodiment 18

A compound of formula (I) or formula (Ia), which is selected from the list consisting of:

Example 1.1

1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione;

Example 1.4

10-(5-chlorofuran-2-yl)-1,3-dimethyl-5-phenyl-7,8,9,10-tetrahydropyrazino[1',2':1,2]pyrrolo[3,4-d]pyrimidine-2,4(1H,3H)-dione;

Example 1.5

1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione;

Example 1.6

10-(4-Bromothiazol-2-yl)-1,3-dimethyl-5-phenyl-7,8,9,10-tetrahydropyrazino[1',2':1,2]pyrrolo[3,4-d]pyrimidine-2,4(1H,3H)-dione;

Example 1.7

1,3-Dimethyl-5-phenyl-10-(thiazol-2-yl)-7,8,9,10-tetrahydropyrazino[1',2':1,2]pyrrolo[3,4-d]pyrimidine-2,4(1H,3H)-dione;

Example 1.8

1,3-Dimethyl-10-(4-methylthiophen-2-yl)-5-phenyl-7,8,9,10-tetrahydropyrazino[1',2':1,2]pyrrolo[3,4-d]pyrimidine-2,4(1H,3H)-dione;

Example 1.9

1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione;

Example 1.10

10-(5-Ethylfuran-2-yl)-1,3-dimethyl-5-phenyl-7,8,9,10-tetrahydropyrazino[1',2':1,2]pyrrolo[3,4-d]pyrimidine-2,4(1H,3H)-dione;

Example 1.11

5-(4-Fluorophenyl)-1,3-dimethyl-10-(5-methylfuran-2-yl)-7,8,9,10-tetrahydropyrazino[1',2':1,2]pyrrolo[3,4-d]pyrimidine-2,4(1H,3H)-dione;

Example 1.12

1,3-Dimethyl-10-(1-methyl-1H-pyrazol-3-yl)-5-phenyl-7,8,9,10-tetrahydropyrazino[1',2':1,2]pyrrolo[3,4-d]pyrimidine-2,4(1H,3H)-dione;

Example 1.13

1,3-Dimethyl-10-(5-methylthiophen-2-yl)-5-phenyl-7,8,9,10-tetrahydropyrazino[1',2':1,2]pyrrolo[3,4-d]pyrimidine-2,4(1H,3H)-dione;

Example 1.14

10-(2,3-Difluorophenyl)-1,3-dimethyl-5-phenyl-7,8,9,10-tetrahydropyrazino[1',2':1,2]pyrrolo[3,4-d]pyrimidine-2,4(1H,3H)-dione;

Example 1.15

1,3-Dimethyl-5,10-diphenyl-7,8,9,10-tetrahydropyrazino[1',2':1,2]pyrrolo[3,4-d]pyrimidine-2,4(1H,3H)-dione;

Example 1.16

10-(5-Chlorofuran-2-yl)-1,3-dimethyl-5-(m-tolyl)-7,8,9,10-tetrahydropyrazino[1',2':1,2]pyrrolo[3,4-d]pyrimidine-2,4(1H,3H)-dione;

Example 1.17

10-(Cyclohex-3-en-1-yl)-1,3-dimethyl-5-phenyl-7,8,9,10-tetrahydropyrazino[1',2':1,2]pyrrolo[3,4-d]pyrimidine-2,4(1H,3H)-dione;

Example 1.18

10-(4-Bromofuran-2-yl)-1,3-dimethyl-5-phenyl-7,8,9,10-tetrahydropyrazino[1',2':1,2]pyrrolo[3,4-d]pyrimidine-2,4(1H,3H)-dione;

Example 1.19

3-(1,3-Dimethyl-2,4-dioxo-5-phenyl-1,2,3,4,7,8,9,10-octahydropyrazino[1',2':1,2]pyrrolo[3,4-d]pyrimidin-10-yl)benzonitrile;

Example 1.20

10-(furan-2-yl)-1,3-dimethyl-5-phenyl-7,8,9,10-tetrahydropyrazino[1',2':1,2]pyrrolo[3,4-d]pyrimidine-2,4(1H,3H)-dione;

Example 1.21

1,3-Dimethyl-10-(2-methylthiazol-4-yl)-5-phenyl-7,8,9,10-tetrahydropyrazino[1',2':1,2]pyrrolo[3,4-d]pyrimidine-2,4(1H,3H)-dione;

Example 1.22

10-(4-Fluorophenyl)-1,3-dimethyl-5-phenyl-7,8,9,10-tetrahydropyrazino[1',2':1,2]pyrrolo[3,4-d]pyrimidine-2,4(1H,3H)-dione;

Example 1.23

10-(4-Chlorophenyl)-1,3-dimethyl-5-phenyl-7,8,9,10-tetrahydropyrazino[1',2':1,2]pyrrolo[3,4-d]pyrimidine-2,4(1H,3H)-dione;

Example 1.24

3-(10-(5-Chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile;

Example 1.25

3-(1,3-Dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile;

Example 1.26

10-(5-Chlorofuran-2-yl)-1,3-dimethyl-5-(4-methylthiazol-2-yl)-7,8,9,10-tetrahydropyrazino[1',2':1,2]pyrrolo[3,4-d]pyrimidine-2,4(1H,3H)-dione;

Example 2.1

1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione;

Example 2.2

10-(3-chlorophenyl)-1,3-dimethyl-5-phenyl-7,8,9,10-tetrahydropyrazino[1',2':1,2]pyrrolo[3,4-d]pyrimidine-2,4(1H,3H)-dione;

Example 2.3

10-(5-Ethylfuran-2-yl)-1,3-dimethyl-5-phenyl-7,8,9,10-tetrahydropyrazino[1',2':1,2]pyrrolo[3,4-d]pyrimidine-2,4(1H,3H)-dione;

Example 2.4

1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione;

Example 2.5

10-(2,3-Difluorophenyl)-1,3-dimethyl-5-phenyl-7,8,9,10-tetrahydropyrazino[1',2':1,2]pyrrolo[3,4-d]pyrimidine-2,4(1H,3H)-dione;

Example 2.6

10-Cyclohexyl-1,3-dimethyl-5-phenyl-7,8,9,10-tetrahydropyrazino[1',2':1,2]pyrrolo[3,4-d]pyrimidine-2,4(1H,3H)-dione;

Example 2.7

10-(Furan-2-yl)-1,3-dimethyl-5-phenyl-7,8,9,10-tetrahydropyrazino[1',2':1,2]pyrrolo[3,4-d]pyrimidine-2,4(1H,3H)-dione;

Example 2.8

1,3-Dimethyl-5,10-diphenyl-7,8,9,10-tetrahydropyrazino[1',2':1,2]pyrrolo[3,4-d]pyrimidine-2,4(1H,3H)-dione;

Example 2.9

3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile;

Example 2.10

3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile;

Example 3.1

10-(5-Chlorofuran-2-yl)-5-(3-chlorophenyl)-1,3-dimethyl-7,8,9,10-tetrahydropyrazino[1',2':1,2]pyrrolo[3,4-d]pyrimidine-2,4(1H,3H)-dione;

Example 3.2

5-(3-Chlorophenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

Example 3.3

5-(3-Methoxyphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

Example 3.4

10-(5-Chlorofuran-2-yl)-5-(3-methoxyphenyl)-1,3-dimethyl-7,8,9,10-tetrahydropyrazino[1',2':1,2]pyrrolo[3,4-d]pyrimidine-2,4(1H,3H)-dione;

Example 3.5

5-(3,5-Dimethylphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

Example 3.6

10-(5-Chlorofuran-2-yl)-5-(3,5-dimethylphenyl)-1,3-dimethyl-7,8,9,10-tetrahydropyrazino[1',2':1,2]pyrrolo[3,4-d]pyrimidine-2,4(1H,3H)-dione;

Example 3.7

Methyl 3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzoate;

Example 3.8

Methyl 3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzoate;

Example 3.9

10-(5-Chlorofuran-2-yl)-1,3-dimethyl-5-(3-(trifluoromethyl)phenyl)-7,8,9,10-tetrahydropyrazino[1',2':1,2]pyrrolo[3,4-d]pyrimidine-2,4(1H, 3H)-dione;

Example 4.1

1,3-Dimethyl-10-(5-methylfuran-2-yl)-5-phenyl-7,8-dihydro-1H-pyrimido[4',5':3,4]pyrrolo[2,1-c][1,4]oxazine-2,4(3H,10H)-dione;

Example 4.4

10-(5-Bromofuran-2-yl)-1,3-dimethyl-5-phenyl-7,8-dihydro-1H-pyrimido[4',5':3,4]pyrrolo[2,1-c][1,4]oxazine-2,4(3H,10H)-dione;

Example 4.5

1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione;

Example 4.6

10-(3-Chlorophenyl)-1,3-dimethyl-5-(m-tolyl)-7,8-dihydro-1H-pyrimido[4',5':3,4]pyrrolo[2,1-c][1,4]oxazine-2,4(3H,10H)-dione;

Example 4.7

1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione

Example 5.0

1,3,7-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione;

Example 6.0

10-(5-Chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 6.1

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

Example 7.0

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione;

Example 7.1

10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione;

Example 7.2

10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione;

Example 7.3

10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione;

Example 8.0

5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 8.1

10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 9a 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

Example 10

10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 11a 10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione;

Example 12

1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione;

Example 12.1

10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione;

Example 12.2

10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione;

Example 12.3

10-(5-chlorofuran-2-yl)-1,3-dimethyl-5,8-diphenyl-7,8-dihydro-1H-pyrimido[4',5':3,4]pyrrolo[2,1-c][1,4]oxazine-2,4(3H,10H)-dione;

Example 12.4

10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione;

Example 12.5

10-(5-Chlorofuran-2-yl)-1,3,8,8-tetramethyl-5-phenyl-7,8-dihydro-1H-pyrimido[4',5':3,4]pyrrolo[2,1-c][1,4]oxazine-2,4(3H,10H)-dione;

Example 13

11-(4-Chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione;

Example 14

3-(11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile;

Example 15

8-((1H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione;

Example 16

(5-Chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione;

and pharmaceutically acceptable salts thereof.

Embodiment 19

A compound of formula (I) or formula (Ia), which is selected from the list consisting of:

Example 6

(8R,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione:

Example 8.0a 5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 7.0a 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione;

Example 8.1a 10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 6.1

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

Example 11a 10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione;

Example 12.2

10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione;

Example 12.4

10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione;

Example 12

1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione;

Example 7.1a 10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione;

and pharmaceutically acceptable salts thereof.

Embodiment 20

A compound of formula (I) or formula (Ia), which is selected from the list consisting of:

Example 6

(8R,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione:

Example 8.0a 5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 7.0a 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione;

Example 8.1a 10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

Example 6.1

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

Example 11a 10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione;

Example 12.2

10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione;
and pharmaceutically acceptable salts thereof.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides as Embodiment 21, a compound of formula (I), or a pharmaceutically acceptable salt thereof, according to any one of embodiments 1 to 20, in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Embodiment 22

A compound of formula (I), or a pharmaceutically acceptable salt thereof, according to any one of Embodiments 1 to 20, which is in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by CFTR or (ii) associated with CFTR activity, or (iii) characterized by activity (normal or abnormal) of CFTR or (2) reduce or inhibit the activity of CFTR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CFTR; or at least partially reducing or inhibiting the expression of CFTR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra.

Compounds of formula (I), wherein X is NH, $R^4$ is H, and $R^1$, $R^2$, $R^3$ and $R^{4a}$ are as defined hereinabove, may be prepared according to Scheme 1.

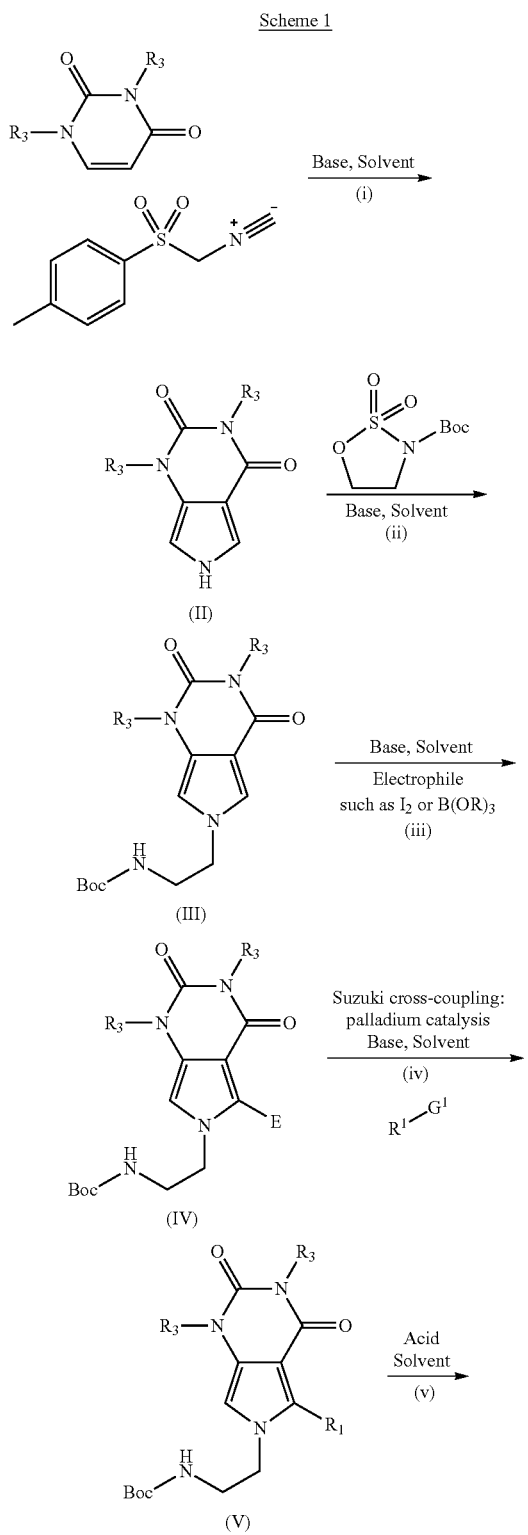

-continued

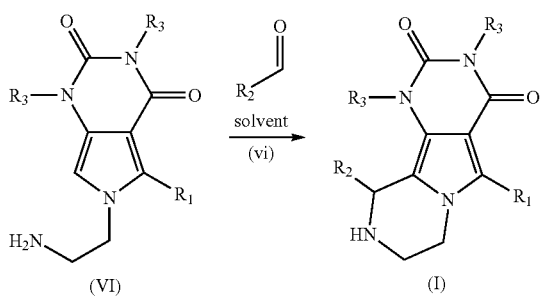

wherein R represents methyl or i-propyl; E represents I and G¹ represents boronic acid or boronate ester; or E represents $B(OH)_2$ and $G^1$ represents Cl, Br, I or OTf.

Step 1(i) An intermediate of formula (II) may be prepared by reaction of a suitable pyrimidine-2,4(1H,3H)-dione with 1-(isocyanomethyl)sulfonyl)-4-methylbenzene in the presence of a suitable base, such as sodium hydride in DMSO/THF or potassium t-butoxide in 2-methyl-THF.

Step 1(ii) An intermediate of formula (III) may be prepared by N-alkylation of an intermediate of formula (II) with tert-butyl-1,2,3-oxathiazolidine-3-carboxylate-2,2-dioxide, in the presence of a suitable base, such as NaH in THF.

Step 1(iii) An intermediate of formula (IV) maybe prepared from an intermediate of formula (III) by reaction with a suitable electrophile, such as $I_2$ or $B(OR)_3$, in the presence of a suitable base, such as LDA or BuLi. The skilled person will recognize that the C5-lithiated species may either be pre-formed or formed in-situ in the presence of the appropriate electrophile.

Step 1(iv) An intermediate of formula (V) may be prepared from an intermediate of formula (IV) via a Suzuki cross-coupling reaction with a compound of formula $R^1$-$G^1$, in the presence of a suitable palladium catalyst, such as tetrakis (triphenylphosphine)palladium (0) or 1,1"bis(di-t-butylphosphino)ferrocene palladium dichloride (Johnson Matthey PD-118).

Step 1(v) An intermediate of formula (VI) may be prepared from an intermediate of formula (V) by removal of the BOC protecting group in the presence of a suitable acid, such as TFA.

Step 1(vi) A compound of formula (I) may be prepared from an intermediate of formula (VI) by reaction with the required aldehyde and the application of heat in a suitable solvent such as ethanol, optionally in the presence of catalytic protic acid, such as TFA.

Compounds of formula (I), wherein X, $R^1$, $R^2$, $R^3$, $R^4$ and $R^{4a}$ are as defined hereinabove, may be prepared according to Scheme 2.

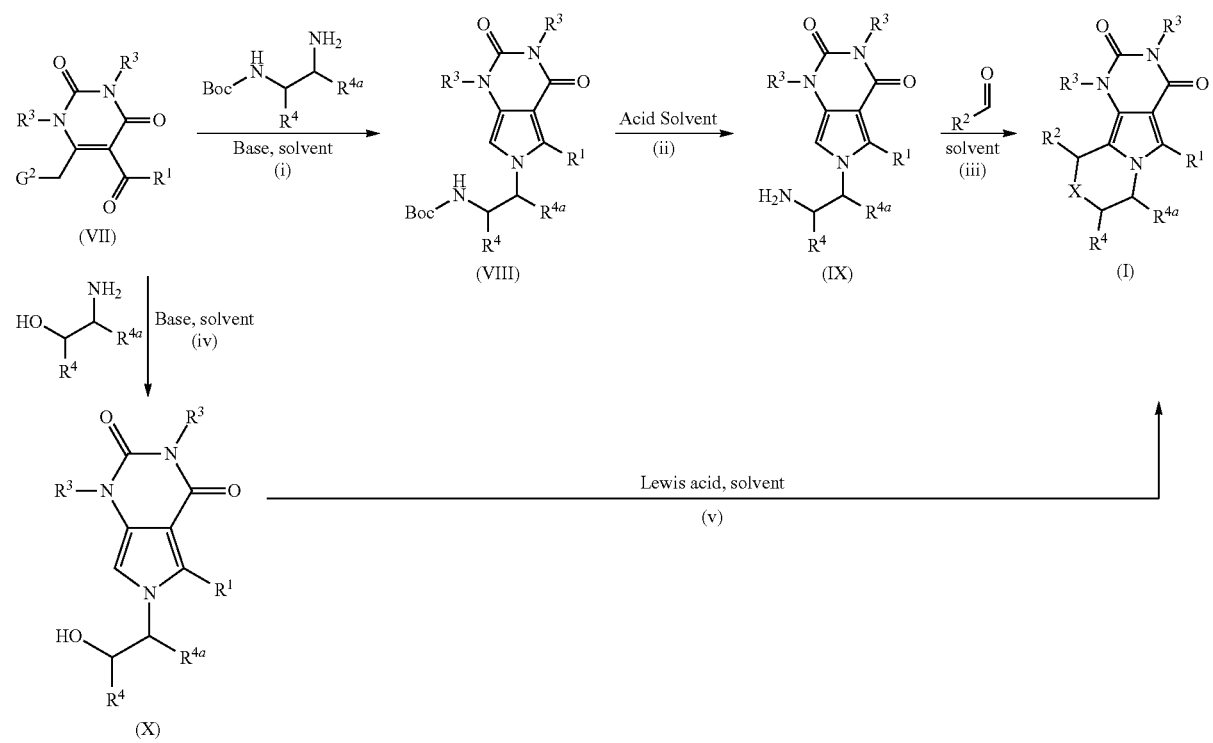

Scheme 2 wherein $G^2$ represents halide, preferably bromide.

Step 2(i) An intermediate of formula (VIII) may be prepared by reaction of an intermediate of formula (VII) with the required mono-protected diamine in the presence of a suitable base, such as triethylamine in ethanol.

Step 2(ii) Deprotection of an intermediate of formula (VIII) to provide an intermediate of formula (IX) may be carried out in the presence of a suitable acid, such as TFA.

Step 2(iii) A compound of formula (I) may be prepared from an intermediate of formula (IX) by reaction with the required aldehyde and the application of heat in an appropriate solvent such as ethanol, optionally in the presence of catalytic protic acid, such as TFA.

Step 2(iv) An intermediate of formula (X) may be prepared by reaction of an intermediate of formula (VII) with the required amino alcohol in the presence of a suitable base, such as triethylamine in ethanol.

Step 2(v) A compound of formula (I) may be prepared from an intermediate of formula (X) by reaction with the required aldehyde in the presence of a Lewis acid, such as bismuth triflate, in a suitable solvent.

An intermediate of formula (VII) may be prepared according to Scheme 3.

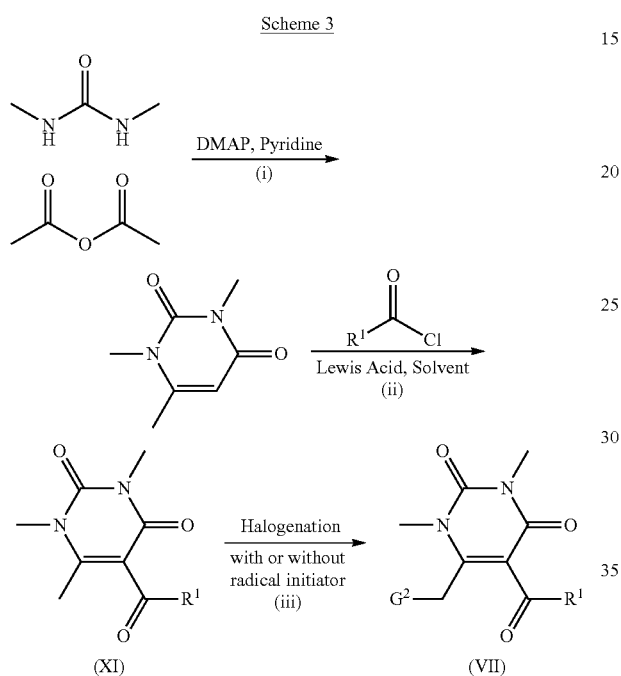

Steps 3(i) and (ii) Intermediates of formula (XI) may be prepared in a two-step process by reaction of acetic anhydride and dimethyl urea, followed by a Friedel-Crafts acylation using the required acyl chloride in the presence of a suitable Lewis acid, such as zinc chloride or aluminium trichloride.

Step 3(iii) An intermediate of formula (VII) may be prepared by halogenation of an intermediate of formula (XI) in the presence or absence of a radical initiator. Suitably, bromine in chloroform may be used.

Compounds of formula (I), wherein X, $R^1$, $R^2$ and $R^3$ are as defined hereinabove, may be prepared according to Scheme 4

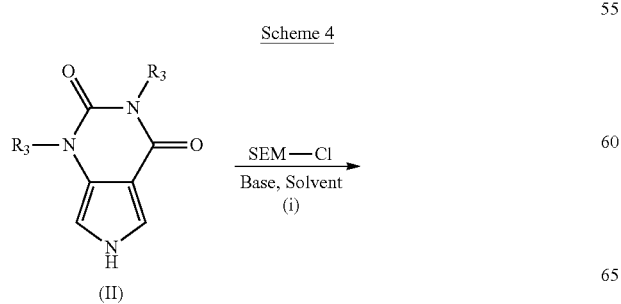

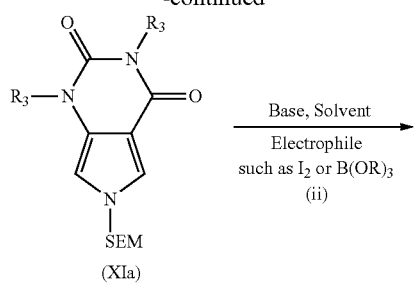

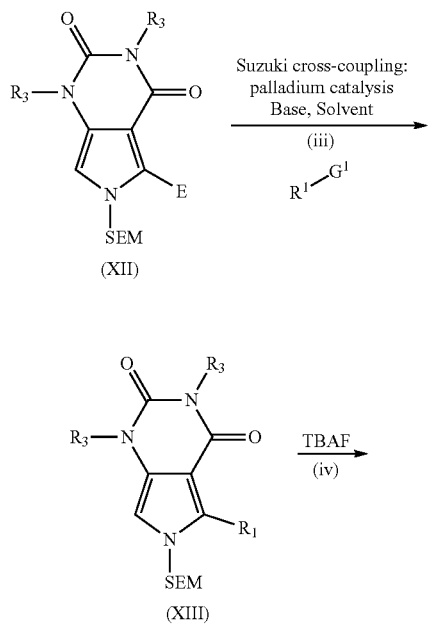

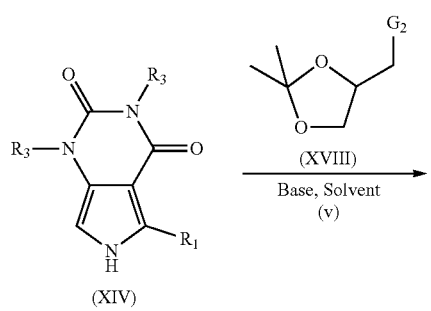

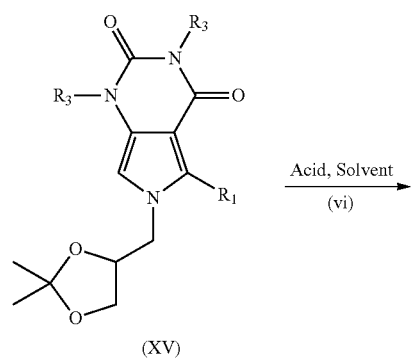

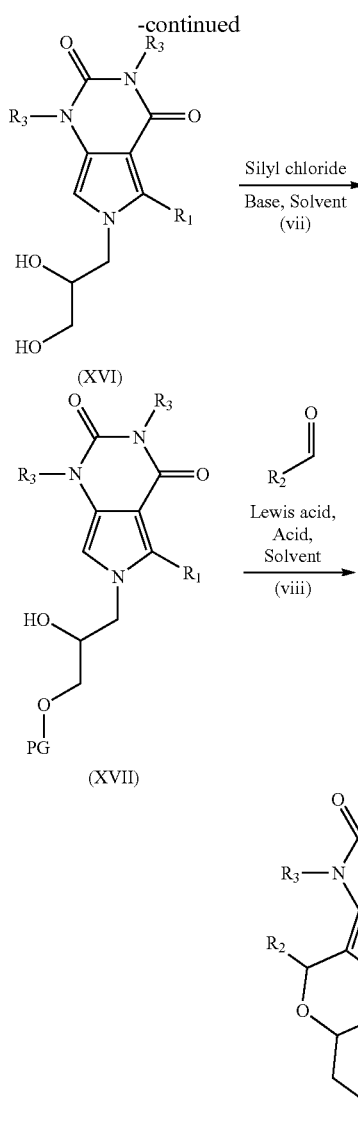

Step 4(v) An intermediate of formula (XV) may be prepared from an intermediate of formula (XIV) by reaction with a suitable electrophile such as Intermediate (XVIII) in the presence of a suitable base, such as sodium hydride in THF.

Step 4(vi) An intermediate of formula (XVI) may be prepared from an intermediate of formula (XV) by removal of the acetonide protecting group in the presence of an acid, such as HCl in diethyl ether Step 4(vii) An intermediate of formula (XVII) may be prepared from an intermediate of formula (XVI) by reaction with a suitable silyl chloride in the presence of a suitable base, such as tertbutyldimethylsilyl chloride in the presence of imidazole in DMF Step 4(viii) An compound of formula (I) may be prepared from an intermediate of formula (XVII) by reaction with the required aldehyde and the application of heat in a suitable solvent such as ethanol, in the presence of a protic acid, such as TFA, and a catalytic lewis acid, such as bismuth triflate.

An intermediate of formula (XVIII) may be prepared according to Scheme 5.

Scheme 5

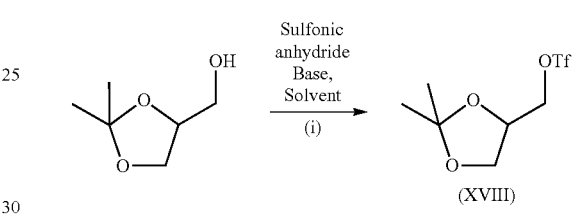

Step 5(i) An intermediate of formula (XVIII) may be prepared from the commercially available alcohol by reaction with a suitable sulfonic anhydride in the presence of a suitable base, such as trifluoromethanesulfonic anhydride in the presence of 2,6-lutidine in THF.

Compounds of formula (I), wherein X, $R^1$, $R^2$, $R^3$, $R^4$ and $R^{4a}$ are as defined hereinabove, may be prepared according to Scheme 6.

Scheme 6

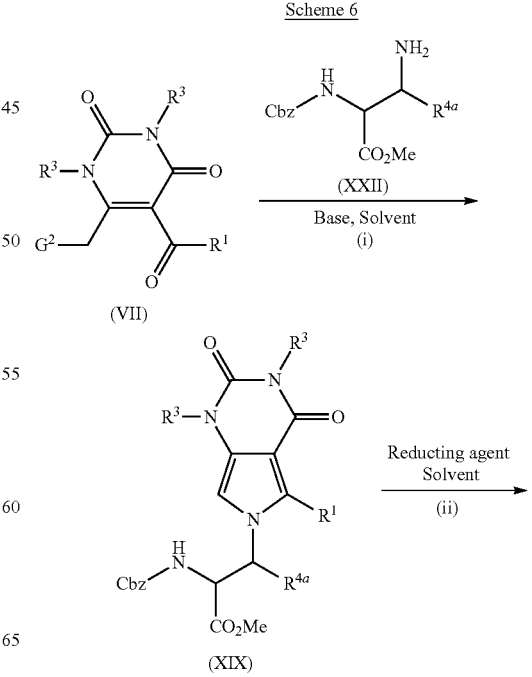

wherein $G^1$ represents halide or boronate ester, $G^2$ represents halide or triflate, and PG represents trialkylsilyl.

Step 4(i) An intermediate of formula (XIa) may be prepared by reaction of an intermediate of formula (II) with SEM-Cl in the presence of a suitable base, such as sodium hydride in THF Step 4(ii) An intermediate of formula (XII) may be prepared from an intermediate of formula (XI) by reaction with a suitable electrophile, such as $I_2$ or $B(OR)_3$, in the presence of a suitable base, such as LDA or BuLi. The skilled person will recognize that the C5-lithiated species may either be pre-formed or formed in-situ in the presence of the appropriate electrophile.

Step 4(iii) An intermediate of formula (XIII) may be prepared from an intermediate of formula (XII) via a Suzuki cross-coupling reaction with a compound of formula $R^1$-$G^1$, in the presence of a suitable palladium catalyst, such as tetrakis(triphenylphosphine)palladium (0) or 1,1"bis(di-t-butylphosphino)ferrocene palladium dichloride (Johnson Matthey PD-118).

Step 4(iv) An intermediate of formula (XIV) may be prepared from an intermediate of formula (XIII) by removal of the SEM protecting group in the presence of a reagent such as TBAF in THF.

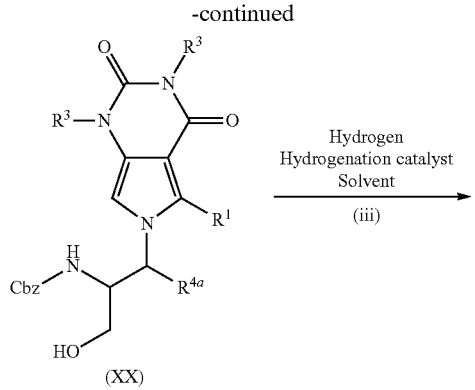

(XX)

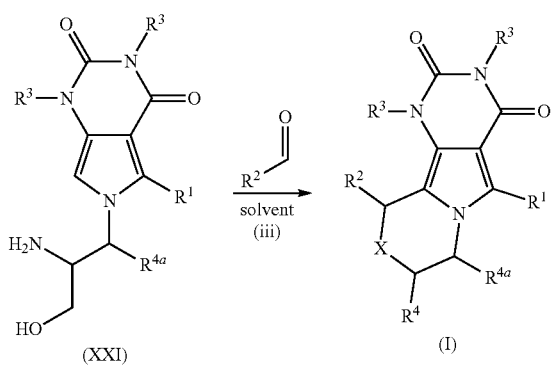

wherein $G^2$ represents halide, preferably bromide.

Step 6(i) An intermediate of formula (XIX) may be prepared by reaction of an intermediate of formula (VII) with an intermediate of formula (XXII) in the presence of a suitable base, such as triethylamine in ethanol.

Step 6(ii) An intermediate of formula (XX) may be prepared by treatment of an intermediate of formula (XIX) with a reducing agent, such as sodium borohydride-lithium chloride in ethanol Step 6(iii) An intermediate of formula (XXI) may be prepared from an intermediate of formula (XX) by removal of the Cbz-protecting group under conditions of catalytic hydrogenation, using a hydrogenation catalyst such as palladium on carbon in ethanol Step 6(iv) A compound of formula (I) may be prepared from an intermediate of formula (XXI) by reaction with the required aldehyde and the application of heat in an appropriate solvent such as ethanol An intermediate of formula (XXII) may be prepared according to Scheme 7.

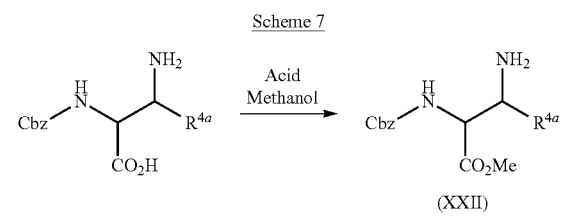

Step 7(i) An intermediate of formula (XXII) may be prepared from the commercially available amino acid by reaction with methanol in the presence of anhydrous acid, prepared by addition of acetyl chloride to methanol Compounds of formula (I), wherein specifically $X=\!\!-\!\!CH_2O\!\!-\!\!$ as defined above and $R^1$, $R^2$, $R^3$, $R^4$ and $R^{4a}$ are as defined hereinabove, may be prepared according to Scheme 8

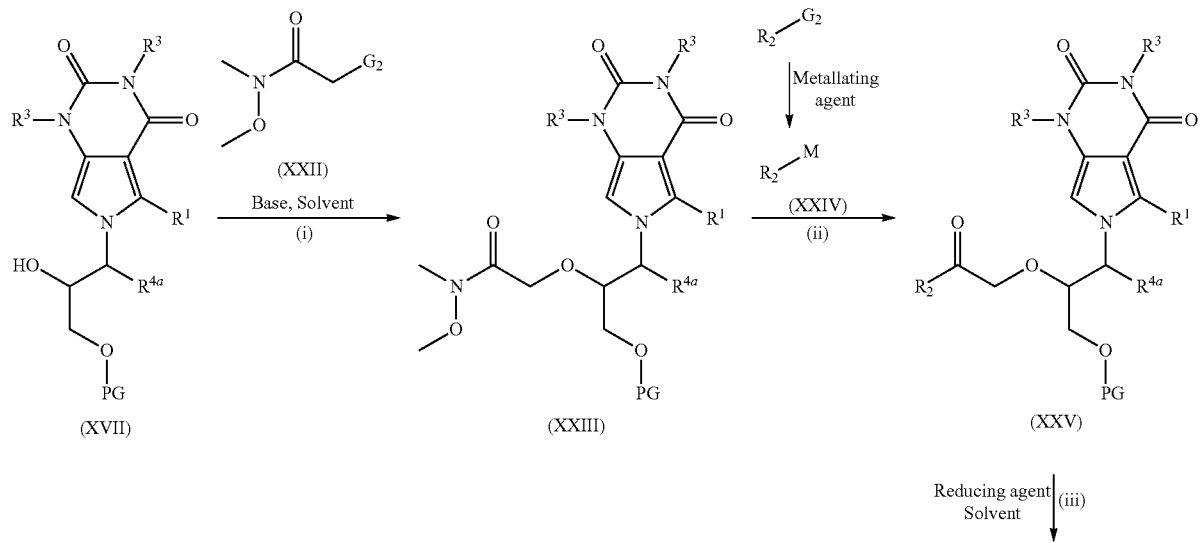

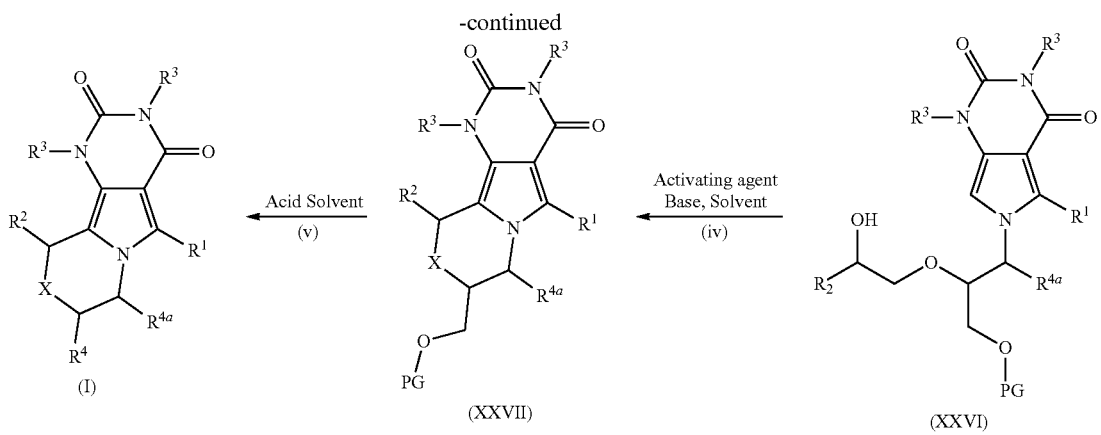

(I)    (XXVII)    (XXVI)

Where $G_2$ represents halide, preferably bromide or iodide, and PG represents a protecting group such as trialkylsilyl Step 8(i) An intermediate of formula (XXIII) may be prepared from a compound of formula (XVII) by reaction with an intermediate of formula (XXII) in the presence of a suitable base in a suitable solvent, such as potassium carbonate in acetone Step 8(ii) An intermediate of formula (XXV) may be prepared from an intermediate of formula (XXIII) by reaction with an intermediate of formula (XXIV) in a suitable solvent, such as THF. An intermediate of formula (XXIV) may be directly prepared from the appropriate halo compound and a suitable metallating agent, such as isopropylmagnesium chloride-lithium chloride Step 8(iii) An intermediate of formula (XXVI) may be prepared from an intermediate of formula (XXV) by treatment with a suitable reducing agent in a suitable solvent, such as sodium borohydride in methanol Step 8(iv) An intermediate of formula (XXVII) may be prepared from an intermediate of formula (XXVI) by treatment with a suitable activating agent in the presence of a suitable base in a suitable solvent, such as triflic anhydride in the presence of triethylamine in DCM Step 8(v) A compound of formula (I) may be prepared from an intermediate of formula (XXVII) by removal of the protecting group using a suitable acid in a suitable solvent, such a trifluoroacetic acid in methanol-water An intermediate of formula (XXII) may be prepared according to Scheme 9

Scheme 9

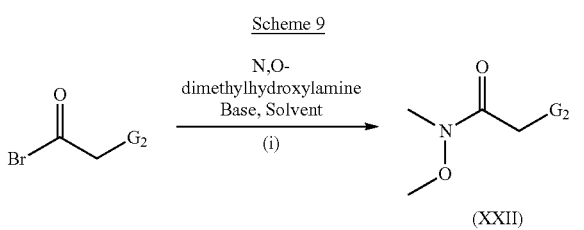

(XXII)

wherein $G_2$ is halide, preferably bromide

Step 9(i) An intermediate of formula (XXII) may be prepared from the commercially available acid halide by treatment with N,O-dimethylhydroxylamine in the presence of a suitable base in a suitable solvent, such as potassium carbonate in a biphasic DCM-water mixture Compounds of formula (I), wherein X=O and $R^1$, $R^2$, $R^3$ $R^4$, $R^{4a}$ and $Het^2$ are as defined hereinabove, may be prepared according to Scheme 10

Scheme 10

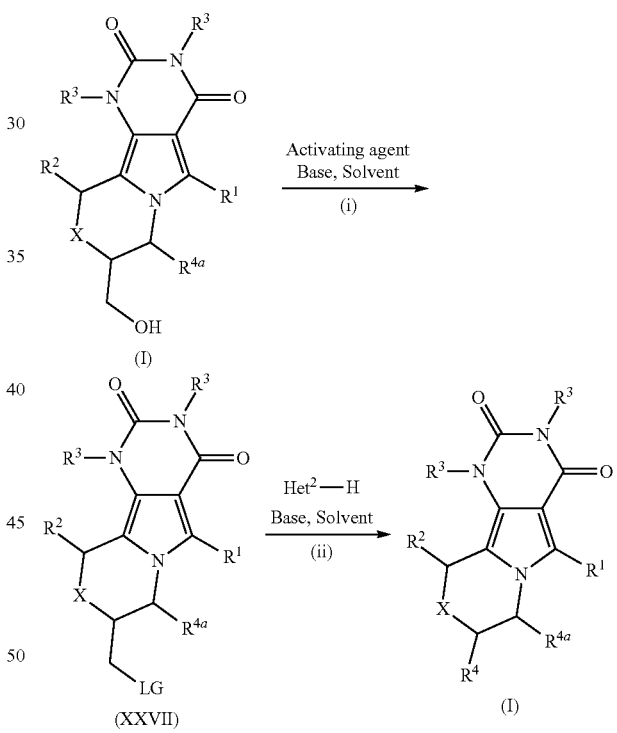

Wherein LG is a leaving group, such as methanesulfonyl.

Step 10(i) An intermediate of formula (XXVII) may be prepared from a compound of formula (I) by treatment with an appropriate activating agent in the presence of a suitable base in a suitable solvent, such as methanesulfonyl chloride in the presence of triethylamine in DCM.

Step 10(ii) A compound of formula (I) may be prepared from an intermediate of formula (XXVII) by reaction with a suitable heterocycle in the presence of a suitable base in a suitable solvent, such as cesium carbonate in DMF.

Compounds of formula (I), wherein X=O and $R^1$, $R^2$, $R^3$ $R^4$, $R^{4a}$ and $Het^2$ are as defined hereinabove, may be prepared according to Scheme 11

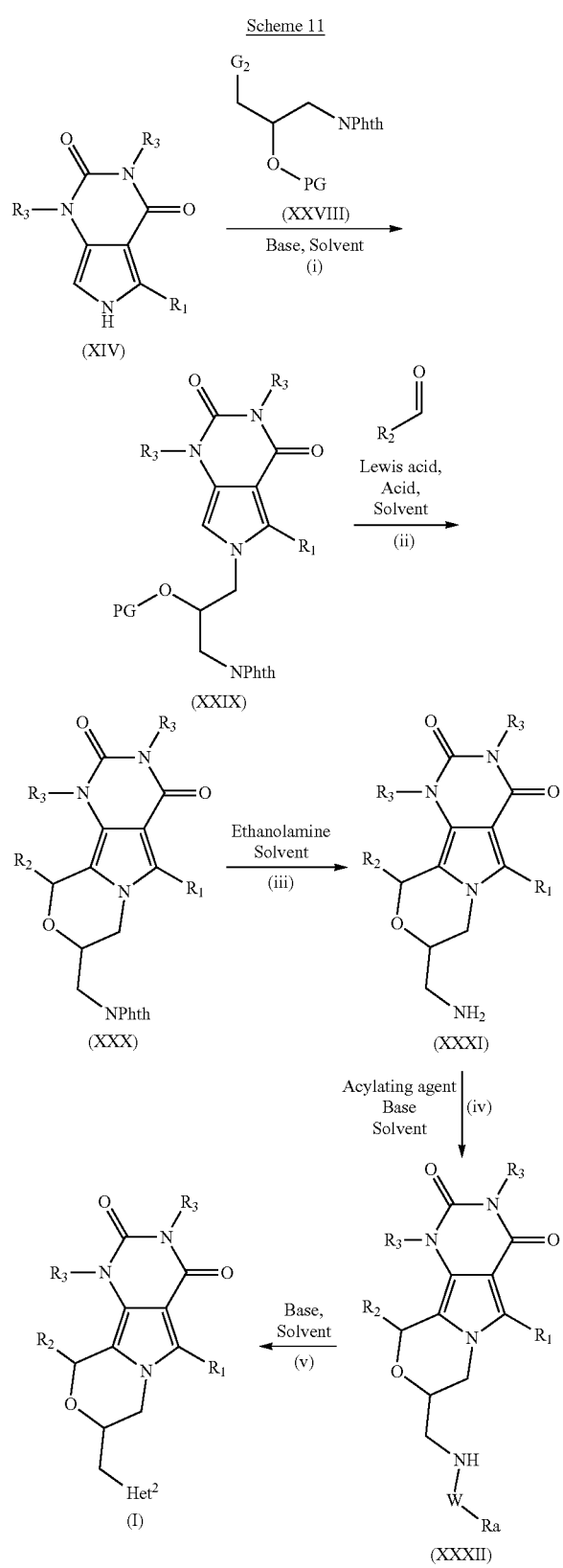

Step 11(i) An intermediate of formula (XXIX) may be prepared from an intermediate of formula (XIV) by reaction with an intermediate of formula (XXVIII) in the presence of a suitable base in a suitable solvent, such as cesium carbonate in dimethylacetamide Step 11(ii) may be carried out in a similar manner to Step 6(iv), with the addition of a suitable acid, such as TFA.

Step 11(iii) Deprotection of the N-phthalimide group may be carried out using ethanolamine and the application of heat Step 11(iv) An intermediate of formula (XXXII) may be prepared from an intermediate of formula (XXXI) by treatment with a suitable acylating agent in the presence of a suitable base in a suitable solvent, such as a haloalkyl chloride in the presence of DIPEA in DCM.

Step 11(v) A compound of formula (I) may be prepared from an intermediate of formula (XXXII) by treatment with a suitable base in a suitable solvent with application of heat, for example sodium hydride in THF.

An intermediate of formula (XXVIII) may be prepared according to Scheme 12

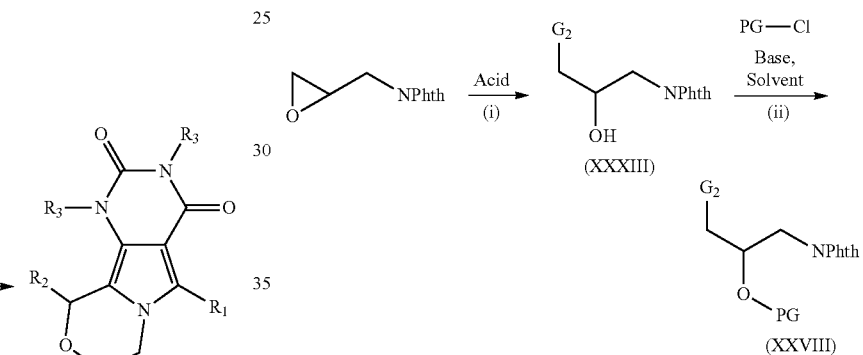

Wherein G2 is halide, preferably bromide and PG is a suitable protecting group such as trialkylsilyl.

Step 12(i) An intermediate of formula (XXXIII) may be prepared from the commercially available epoxide by treatment with a suitable acid, such as concentrated HBr.

Step 12(ii) An intermediate of formula (XXVIII) may be prepared from an intermediate of formula (XXXIII) by an analogous reaction to Step 4(vii)

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with Wherein G2 is halide, preferably bromide, PG is a protecting group such as trialkylsilyl, W is specifically C=O and $R_a$ is specifically halo(C1-C4)alkyl.

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The CFTR chloride channel is known to be associated with a number of diseases and conditions, including cystic fibrosis (CF) (Quinton, *Physiol. Rev.* 79:S3-S22 (1999); Boucher, *Eur. Respir. J* 23:146-58 (2004)), polycystic kidney disease (O'Sullivan et al., *Am. J Kidney Dis.* 32:976-983 (1998); Sullivan et al., *Physiol. Rev.* 78:1165-91 (1998); Strong et al., *J Clin. Invest.* 93:347-54 (1994); Mall et al., *Gastroenterology* 126:32-41 (2004); Hanaoka et al., *Am. J Physiol.* 270: C389-C399 (1996); Kunzelmann et al., *Physiol. Rev.* 82:245-289 (2002); Davidow et al., *Kidney Int.* 50:208-18 (1996); Li et al., *Kidney Int.* 66:1926-38 (2004); Al-Awqati, *J Clin. Invest.* 110:1599-1601 (2002); Thiagarajah et al., *Curr. Opin. Pharmacol.* 3:594-99 (2003)) and secretory diarrhea (Clarke et al., *Science* 257:1125-28 (1992); Gabriel et al., *Science* 266:107-109 (1994); Kunzelmann and Mall, *Physiol. Rev.* 82:245-89 (2002); Field, M. *J Clin. Invest.* 111:931-43 (2003); and Thiagarajah et al., *Gastroenterology* 126:511-519 (2003)).

The compounds of formula (I) in free form or in salt form, exhibit valuable pharmacological properties, e.g. CFTR modulating properties, e.g. as indicated in in vitro and in vivo tests as provided in the next sections, and are therefore indicated for therapy or for use as research chemicals, e.g. as tool compounds. The compounds of formula (I) and (Ia) may be useful in vivo in the development of models of cystic fibrosis.

Compounds of the invention may be useful in the treatment of an indication selected from polycystic kidney disease and diarrhea, including infectious secretory diarrhea, travelers diarrhea, diarrhea associated with HIV and diarrhea predominant irritable bowel syndrome (IBS).

Thus, as a further embodiment, the present invention provides the use of a compound of formula (I) or (Ia) in therapy. In a further embodiment, the therapy is selected from a disease which may be treated by inhibition of CFTR. In another embodiment, the disease is selected from the afore-mentioned list, suitably polycystic kidney disease and diarrhea, more suitably polycystic kidney disease, infectious secretory diarrhea, travellers diarrhea, diarrhea associated with HIV and diarrhea predominant irritable bowel syndrome (IBS).

In another embodiment, the invention provides a method of treating a disease which is treated by inhibition of CFTR comprising administration of a therapeutically acceptable amount of a compound of formula (I) or (Ia) In a further embodiment, the disease is selected from the afore-mentioned list, suitably polycystic kidney disease and diarrhea, more suitably polycystic kidney disease, infectious secretory diarrhea, travellers diarrhea, diarrhea associated with HIV and diarrhea predominant irritable bowel syndrome (IBS).

Thus, as a further embodiment, the present invention provides the use of a compound of formula (I) or (Ia) for the manufacture of a medicament. In a further embodiment, the medicament is for treatment of a disease which may be treated by inhibition of CFTR. In another embodiment, the disease is selected from the afore-mentioned list, suitably polycystic kidney disease and diarrhea, more suitably polycystic kidney disease, infectious secretory diarrhea, travelers diarrhea, diarrhea associated with HIV and diarrhea predominant irritable bowel syndrome (IBS).

Embodiment 23

A compound according to any one of previous Embodiments 1 to 20, or a pharmaceutically acceptable salt thereof, for use in the treatment of polycystic kidney disease and diarrhea, more suitably polycystic kidney disease, infectious secretory diarrhea, travelers diarrhea, diarrhea associated with HIV and diarrhea predominant irritable bowel syndrome (IBS).

The pharmaceutical composition or combination of the present invention can be in unit dosage of about 1-2000 mg of active ingredient(s) for a subject of about 50-70 kg, or about 1-1000 mg or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following methods.

IonWorks Quattro Assay:

CFTR activity can be quantified by electrophysiology methods, using the whole-cell configuration of the patch clamp technique (Hamill O, Marty A, Neher E, Sakmann B and Sigworth F. 'Improved patch-clamp techniques for high resolution current recording from cells and cell-free membrane patches.' Pflugers Archive 1981 391: 85-100). This assay directly measures the currents associated with chloride flow through CFTR channels whilst either maintaining or adjusting the transmembrane voltage. This assay can use either single glass micropipettes or parallel planar arrays to measure CFTR activity from native or recombinant cell systems. Currents measured using parallel planar arrays can be quantified using an appropriately equipped instrument such as the IonWorks Quattro (Molecular Devices Corporation, Sunnyvale, Calif.). The Quattro system can measure CFTR currents from either a single cell per recording well (HT configuration) or alternatively from a population of 64 cells per well (Population Patch Clamp PPC) (Finkel A, Wittel A, Yang N, Handran S, Hughes J, Costantin J. 'Population patch clamp improves data consistency and success rates in the measurement of ionic currents.' J Biomol Screen. 2006 August; 11(5):488-96).

Cell Culture:

Chinese hamster ovary (CHO) cells stably expressing WT-CFTR channels were used for the IonWorks Quattro experiments. Cells were maintained at 37° C. in 5% v/v $CO_2$ at 100% humidity in MEM alpha medium supplemented with 10% (v/v) FCS, 100 U/mL Penicillin/Streptomycin, and 100 µg/L methotrexate. For experiments, cells were grown in 225 $cm^2$ tissue culture flasks until almost confluent. Cells were removed from the flask using trypsin-EDTA and resuspended in extracellular recording solution for immediate experimentation.

CFTR Inhibitor Assay:

Cells, at a density of 1.5-2 million per mL, were placed on the Quattro system, added to the planar patch plate and seals allowed to establish for 5-10 mins. After assessing seal resistances (typically >50 MΩ), whole-cell access was obtained by perforation with 100 µg/mL amphotericin B. Baseline currents were measured by a pre-compound scan obtained by application of a voltage ramp from −100 to +100 mV. CFTR was activated by the addition of 10 µM forskolin to each of the 384 wells of the patch plate. After 5 min incubation the post-compound 1 currents were measured, again by application of a voltage ramp from −100 to +100 mV. Test compounds, diluted from 10 mM stocks in DMSO in extracellular solution were then added to the patch plate and were incubated for a further 10 min. The post-compound 2 currents were measured by the application of the same voltage ramp from −100 to +100 mV. The inhibition of CFTR was determined from the difference in current between the forskolin addition (post-compound 1) and the test compound (post-compound 2). This was determined at both −100 mV and +100 mV which represents the inward and outward current respectively.

Solutions:

Extracellular solution (ECS): 145 mM NaCl, 4 mM CsCl, 5 mM D-glucose, 10 mM TES, 1 mM $CaCl_2$, 1 mM $MgCl_2$, pH 7.4 NaOH Intracellular solution (ICS): 113 mM L-Aspartic acid, 113 mM CsOH, 27 mM CsCl, 1 mM NaCl, 1 mM $MgCl_2$, 1 mM EGTA, 10 mM TES. pH 7.2 with CsOH. Filter sterilized before use.

Using the Ion Works Quattro assay (as described in this application) compounds of the invention exhibit CFTR inhibitory efficacy in accordance with Table A:

TABLE A

Inhibitory Activity of Compounds of Formula (I)

| Example Number | CFTR IC50 (μM) Inward current |
|---|---|
| 1.1 | 4.64 |
| 1.2 | 1.58 |
| 1.3 | >30 |
| 1.7 | 5.42 |
| 1.9 | 6.31 |
| 1.10 | 6.37 |
| 1.12 | 10.78 |
| 1.14 | 11.53 |
| 1.17 | 18.11 |
| 1.23 | 29.94 |
| 1.26 | 1.90 |
| 2.4 | 4.98 |
| 2.6 | 7.62 |
| 2.9 | 0.59 |
| 3.1 | 0.70 |
| 3.2 | 0.64 |
| 3.6 | 8.26 |
| 4.1 | 4.23 |
| 4.2 | >30 |
| 4.3 | 3.16 |
| 5.1 | 3.24 |
| 6 | 0.05 |
| 6.1 | 0.24 |
| 7.0a | 0.09 |
| 7.1a | 0.61 |
| 8.0a | 0.07 |
| 8.1a | 0.12 |
| 9b | 8.06 |
| 11a | 0.31 |
| 12 | 0.60 |
| 12.1 | 5.07 |
| 12.2 | 0.24 |
| 12.4 | 0.54 |
| 12.5 | 0.62 |
| 13 | 3.53 |
| 14 | 1.96 |

The compounds of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by CFTR. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I).

In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or (Ia) for treating a disease or condition mediated by CFTR, wherein the medicament is prepared for administration with another therapeutic agent. The invention also provides the use of another therapeutic agent for treating a disease or condition mediated by CFTR, wherein the medicament is administered with a compound of formula (I).

The invention also provides a compound of formula (I) or (Ia) for use in a method of treating a disease or condition mediated by CFTR, wherein the compound of formula (I) or (Ia) is prepared for administration with another therapeutic agent. The invention also provides another therapeutic agent for use in a method of treating a disease or condition mediated by CFTR, wherein the other therapeutic agent is prepared for administration with a compound of formula (I) or (Ia). The invention also provides a compound of formula (I) or (Ia) for use in a method of treating a disease or condition mediated by CFTR, wherein the compound of formula (I) or (Ia) is administered with another therapeutic agent. The invention also provides another therapeutic agent for use in a method of treating a disease or condition mediated by CFTR, wherein the other therapeutic agent is administered with a compound of formula (I) or (Ia).

The invention also provides the use of a compound of formula (I) for treating a disease or condition mediated by CFTR, wherein the patient has previously (e.g. within 24 hours) been treated with another therapeutic agent. The invention also provides the use of another therapeutic agent for treating a disease or condition mediated by CFTR, wherein the patient has previously (e.g. within 24 hours) been treated with a compound of formula In one embodiment, the invention provides a combination comprising a therapeutically effective amount of a compound of formula (I) or (Ia) according to any preceding Embodiment, or a pharmaceutically acceptable salt thereof, and one or more therapeutically active co-agents is selected from an anti-diarrheal agent, including an oral rehydration agent; an antibiotic; and an antimotility agent such as loperamide.

Specific individual combinations which may provide particular treatment benefits include a combination of a compound of formula (I) or (Ia) according to any preceding Embodiment, or a pharmaceutically acceptable salt thereof, and loperamide.

EXAMPLES

General Conditions

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer, or Micromass Platform Mass Spectrometer or Thermo LTQ Mass Spectrometer; a Waters Acquity UPLC system with SQD Mass Spectrometer, a Waters FractionLynx HPLC system with 3100 Mass Spectrometer, a Waters UPC2 system with TQD Mass Spectrometer or a Waters Prep100 SFC-MS system with SQD2 Mass Spectrometer. [M+H]+ refers to protonated molecular ion of the chemical species. NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations

BOC tertiary butyl carboxy
br broad
CBA weak cation exchange (e.g Isolute® CBA columns from Biotage)
d doublet
dd doublet of doublets
ddd doublet of doublet of doublets
de diastereomeric excess
d.e. diastereomeric excess
deg C ° C.
DCM dichloromethane
DIPEA diisopropylethylamine
DMAP 4-dimethylaminopyridine
DMF N,N-dimethylformamide
DMSO dimethylsulfoxide
ee enantiomeric excess
e.e. enantiomeric excess
EtOAc ethyl acetate
EtOH ethanol
GC-MS gas chromatography and mass spectrometry
h hour(s)
HCl hydrochloric acid
HPLC high pressure liquid chromatography
Int. intermediate
IR Infrared spectroscopy
LCMS liquid chromatography and mass spectrometry
LC-MS liquid chromatography and mass spectrometry
MeOH methanol
2-Me-THF 2-methyltetrahydrofuran
MS mass spectrometry
m multiplet
mult multiplet
min minutes
mL milliliter(s)
m/z mass to charge ratio
NaOH sodium hydroxide
NBS N-bromosuccinimide
NMR nuclear magnetic resonance
O/N overnight
Pd-118 1,1"bis(di-t-butylphosphino)ferrocene palladium dichloride
ppm parts per million
PS polymer supported
PE-AX PE-anion exchange (e.g. Isolute® PE-AX columns from Biotage)
RT room temperature
Rt retention time
s singlet
SCX-2 strong cation exchange (e.g. Isolute® SCX-2 columns from Biotage)
SEM-Cl (2-(chloromethoxy)ethyl)trimethylsilane
SFC Supercritical fluid chromatography
t triplet
T3P® 2,4,6-Tripropyl-1,3,5,2,4,6-trioxatriphosphorinane-2,4,6-trioxide solution
TBAF Tetrabutylammonium fluoride solution
TEA triethylamine
TFA trifluoroacetic acid
THF tetrahydrofuran
UPLC ultra performance liquid chromatography Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:
LowpH_v002
  Column Phenomenex Gemini C18 50×4.6 mm, 3.0 μm
  Column Temperature 50° C.
  Eluents A: $H_2O$, B: MeOH, both containing 0.1% TFA
  Flow Rate 1.0 mL/min
  Gradient 5% to 95% B in 2.0 min, 0.2 min 95% B
2minLC_v003
  Column Waters BEH C18 50×2.1 mm, 1.7 μm
  Column Temperature 50° C.
  Eluents A: $H_2O$, B: acetonitrile, both containing 0.1% TFA
  Flow Rate 0.8 mL/min
  Gradient 0.20 min 5% B; 5% to 95% B in 1.30 min, 0.25 min 95% B
10minLC_v003
  Column Waters BEH C18 50×2.1 mm, 1.7 μm
  Column Temperature 50° C.
  Eluents A: $H_2O$, B: acetonitrile, both containing 0.1% TFA
  Flow Rate 0.8 mL/min
  Gradient 0.20 min 5% B; 5% to 95% B in 7.80 min, 1.00 min 95% B
2minLC_30_v003
  Column Waters BEH C18 50×2.1 mm, 1.7 μm
  Column Temperature 50° C.
  Eluents A: $H_2O$, B: acetonitrile, both containing 0.1% TFA
  Flow Rate 0.8 mL/min Gradient 0.25 min 30% B; 30% to 95% B in 1.00 min, 0.25 min 95% B 2minLowpH:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B 2minLowpHv01:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B 2minLowpH/03:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.8 min 5-98% B, 1.8-2.1 min 98% B, 2.1-2.3 min 98% B 2minLowpH30:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 30% B, 0.2-1.3 min 30-98% B, 1.3-1.55 min 98% B, 1.55-1.6 min 98-30% B 2minLowpH50:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 50% B, 0.2-1.3 min 50-98% B, 1.3-1.55 min 98% B, 1.55-1.6 min 98-50% B 2minLowpH80:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 80% B, 0.2-1.3 min 80-98% B, 1.3-1.55 min 98% B, 1.55-1.6 min 98-80% B 10minLowpH:
Column: Waters Acquity CSH 1.7 μm, 2.1×100 mm
Temperature: 50° C.
Mobile Phase: A: Water+0.1% Formic Acid B: Acetonitrile+0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B 2minHighpH:
Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 5% B, 0.2-1.3 min 5-98% B, 1.3-1.55 min 98% B, 1.55-1.6 min 98-5% B 2minHighpH30:
Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 30% B, 0.2-1.3 min 30-98% B, 1.3-1.55 min 98% B, 1.55-1.6 min 98-30% B 2minHighpH50:
Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 50% B, 0.2-1.3 min 50-98% B, 1.3-1.55 min 98% B, 1.55-1.6 min 98-50% B 2minHighpH80:
Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 80% B, 0.2-1.3 min 80-98% B, 1.3-1.55 min 98% B, 1.55-1.6 min 98-80% B 10minHighpH:
Column: Waters Acquity CSH 1.7 μm, 2.1×100 mm
Temperature: 50° C.
Mobile Phase: A: Water+0.1% Ammonia B: Acetonitrile+0.1% Ammonia
Flow rate: 0.7 mL/min
Gradient: 0.0 min 2% B, 0.5-8.0 min 2-98% B, 8.0-9.0 min 98% B, 9.0-9.1 min 98-2% B Preparation of Final Compounds Unless otherwise indicated, the chemical name refers to the racemic compound or to the diastereomeric mixture. The term 'Enantiomer 1' refers to the more active of the separated enantiomers and does not indicate the relative position of the eluted peak within the chromatogram (where separation is achieved by SFC under the specified conditions). The term 'Diastereomer 1' refers to the more active of the separated diastereomers and does not indicate the relative position of the eluted peak within the chromatogram (where separation is achieved by SFC under the specified conditions).

Example 1.1

1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione

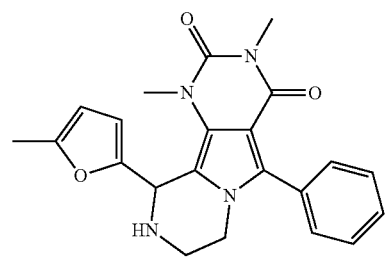

6-(2-Amino-ethyl)-1,3-dimethyl-5-phenyl-1,6-dihydro-pyrrolo[3,4-d]pyrimidine-2,4-dione (Intermediate A) (519 mg, 1.740 mmol) in EtOH (3 mL) was treated with 5-methylfuran-2-carbaldehyde (commercial) (0.173 mL, 1.740 mmol) and heated at 100° C. for 30 min using microwave irradiation. A further portion of 5-methylfuran-2-carbaldehyde (0.173 mL, 1.740 mmol) was added and heating continued at 100° C. for 10 min. The solvent was removed under reduced pressure and purification by chromatography on silica eluting with 40-80% EtOAc in iso-hexanes afforded the title compound as a yellow solid.

1H NMR (400 MHz, DMSO-d6) δ 7.45 (5H, s), 5.97 (1H, d), 5.89 (1H, d), 5.73 (1H, s), 3.77-3.74 (2H, m), 3.27 (3H, s), 3.14 (3H, s), 3.06 (1H, br s), 2.92-2.86 (2H, m), 2.26 (3H, s);

LC-MS Rt=0.85 min [M+H]+ 391 (Method 2min-LC_v003).

Chiral separation of the racemate by Supercritical Fluid Chromatography was carried out using the following conditions to afford the compounds listed hereinafter:

Mobile Phase: 40% MeOH/60% CO2
Column: Chiralpak AD-H, 250×10 mm, 5 um
Detection: UV @ 220 nm
Flow rate: 10 mL/min
Injection volume: 200 μl
Examples 1.2 and 1.3 are enantiomers.

Example 1.2

Enantiomer 1 Rt=5.06 min. (R)-1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione 1H NMR (400 MHz, CDCl3) δ 7.51-7.41 (5H, m), 5.88 (1H, d), 5.80 (1H, d), 5.77 (1H, s), 3.97-3.83 (2H, m), 3.42 (3H, s), 3.35 (3H, s), 3.18-3.07 (1H, m), 3.08-3.01 (1H, m), 2.32 (3H, s);

LC-MS Rt=0.86 min [M+H]+ 391 (Method 2min-LC_v003).

Chiral purity >99% ee

Example 1.3

Enantiomer 2 Rt=3.26 min. (S)-1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione

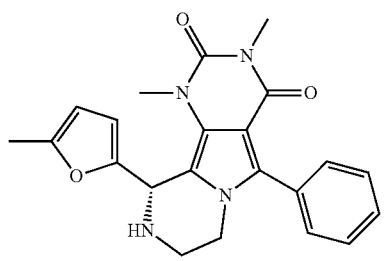 [SMILES: Cc1ccc([C@H]2NCCn3c(-c4ccccc4)c4c(=O)n(C)c(=O)n(C)c4c32)o1]

1H NMR (400 MHz, CDCl3) δ 7.51-7.41 (5H, m), 5.88 (1H, d), 5.80 (1H, d), 5.76 (1H, s), 3.96-3.83 (2H, m), 3.42 (3H, s), 3.35 (3H, s), 3.18-3.07 (1H, m), 3.07-3.00 (1H, m), 2.32 (3H, s);

LC-MS Rt=0.85 min MS m/z 391 [M+H] (Method 2min-LC_v003).

Chiral purity 95% ee

X-Ray Crystallography

Absolute stereochemistry of enantiomers was confirmed by X-ray crystallography of (S)-1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione (Ex 1.3).

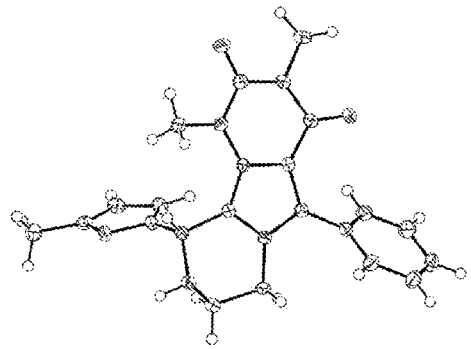

Crystal Data and Structure

| | |
|---|---|
| Empirical formula | C22H22N4O3 |
| Formula weight | 390.44 |
| Temperature | 100(2) K |
| Wavelength | 1.54178 Å |
| Crystal system | Orthorhombic |
| Space group | P212121 |
| Unit cell dimensions | a = 10.053(3) Å   α = 10 |
| | b = 11.832(3) Å   β = 11 |
| | c = 15.998(4) Å   γ = 15 |
| Volume | 1902.9(9) Å$^3$ |
| Z | 4 |
| Density (calculated) | 1.363 g/cm$^3$ |
| Absorption coefficient | 0.756 mm$^{-1}$ |
| F(000) | 824 |
| Crystal size | 0.40 × 0.33 × 0.03 mm$^3$ |
| Theta range for data collection | 4.65 to 66.69° |
| Index ranges | −11 <= h <= 11, |
| | −14 <= k <= 14, |
| | −19 <= l <= 19 |
| Reflections collected | 38080 |
| Independent reflections | 3361 [R(int) = 0.0382] |
| Completeness to theta = 66.69° | 99.7% |
| Absorption correction | Semi-empirical from equivalents |
| Max. and min. transmission | 0.9777 and 0.7519 |
| Refinement method | Full-matrix least-squares on F$^2$ |
| Data/restraints/parameters | 3361/0/265 |
| Goodness-of-fit on F$^2$ | 1.079 |
| Final R indices [I > 2sigma(I)] | R1 = 0.0248, wR2 = 0.0640 |
| R indices (all data) | R1 = 0.0253, wR2 = 0.0647 |
| Absolute structure parameter | 0.01(14) |
| Largest diff. peak and hole | 0.147 and −0.175 e · Å$^{-3}$ |

The compounds of the following tabulated examples (Table 1) were prepared by a similar method to that of Example 1.1 from Intermediate A, Intermediate Aa, Intermediate Ab, Intermediate Be or Intermediate Bf (as appropriate) and a commercially available aldehyde.

TABLE 1

| Ex | Structure | Name | LCMS/NMR |
|---|---|---|---|
| 1.4 | 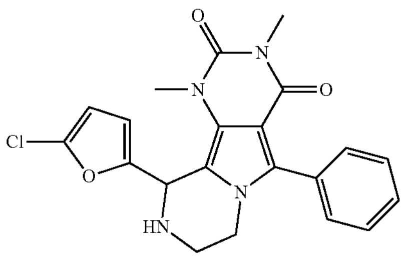 [SMILES: Cn1c(=O)c2c(-c3ccccc3)n3c(c2n(C)c1=O)C(c1ccc(Cl)o1)NCC3] | 10-(5-chlorofuran-2-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.86 min; 393 [M + H]+; 2minLC_v003;1H NMR: (400 MHz, CDCl3) δ 7.49-7.44 (5H, m), 6.12 (1H, d), 5.96 (1H, d), 5.81 (1H, s), 3.96-3.86 (2H, m), 3.44 (3H, s), 3.36 (3H, s), 3.11-3.08 (2H, m). |
| 1.5 | 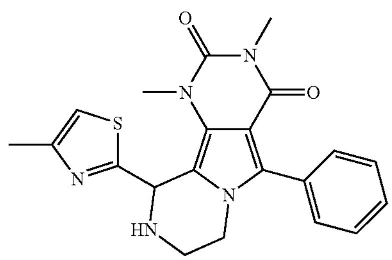 [SMILES: Cc1csc(C2NCCn3c(-c4ccccc4)c4c(=O)n(C)c(=O)n(C)c4c32)n1] | 1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione | LCMS: Rt 0.85 min; 408 [M + H]+; 2minLC_v003; 1H NMR: (400 MHz, CDCl3) δ 7.55-7.45 (5H, m), 6.88 (1H, s), 6.01 (1H, s), 3.99-3.88 (2H, m), 3.43 (3H, s), 3.36 (3H, s), 3.18-3.06 (2H, m), 2.48 (3H, s). |
| 1.6 | 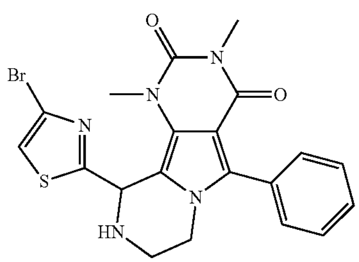 [SMILES: Cn1c(=O)c2c(-c3ccccc3)n3c(c2n(C)c1=O)C(c1nc(Br)cs1)NCC3] | 10-(4-Bromothiazol-2-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.87 min; 473 [M + H]+; 2minLC_v003; 1H NMR: (400 MHz, CDCl3) δ 7.51-7.44 (5H, m), 7.24 (1H, s), 6.00 (1H, s), 3.99-3.86 (2H, m), 3.46 (3H, s), 3.36 (3H, s), 3.11-3.06 (2H, m), 2.86 (1H, bs). |
| 1.7 | 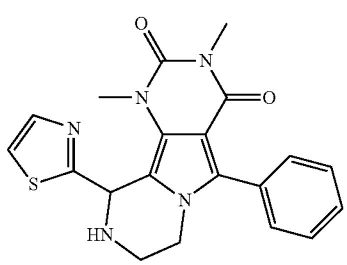 [SMILES: Cn1c(=O)c2c(-c3ccccc3)n3c(c2n(C)c1=O)C(c1nccs1)NCC3] | 1,3-Dimethyl-5-phenyl-10-(thiazol-2-yl)-7,8,9,10-tetrahydropyrazino[1',2':1,2]pyrrolo[3,4-d]pyrimidine-2,4(1H,3H)-dione | LCMS: Rt 0.80 min; 394 [M + H]+; 2minLC_v003; 1H NMR: (400 MHz, CDCl3) δ 7.83 (1H, d), 7.50-7.45 (5H, m), 7.35 (1H, d), 6.03 (1H, s), 3.97-3.86 (2H, m), 3.45 (3H, s), 3.36 (3H, s), 3.12-3.09 (2H, m), 2.73 (1H, br s). |
| 1.8 | 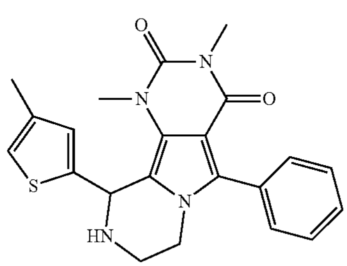 [SMILES: Cc1csc(C2NCCn3c(-c4ccccc4)c4c(=O)n(C)c(=O)n(C)c4c32)c1] | 1,3-Dimethyl-10-(4-methylthiophen-2-yl)-5-phenyl-7,8,9,10-tetrahydropyrazino[1'2':1,2]pyrrolo[3,4-d]pyrimidine-2,4(1H,3H)-dione | LCMS: Rt 0.75 min; 407 [M + H]+; 2minLowpH; 1H NMR: (400 MHz, CDCl3) δ 7.54-7.45 (5H, m), 6.88 (1H, s), 6.48 (1H, s), 5.92 (1H, s), 3.96-3.92 (1H, m), 3.85-3.71 (1H, m), 3.45 (3H, s), 3.37 (3H, s), 3.26-3.19 (1H, m), 3.07-3.04 (1H, m), 1.21 (3H, s). |

TABLE 1-continued

| Ex | Structure | Name | LCMS/NMR |
|---|---|---|---|
| 1.9 | 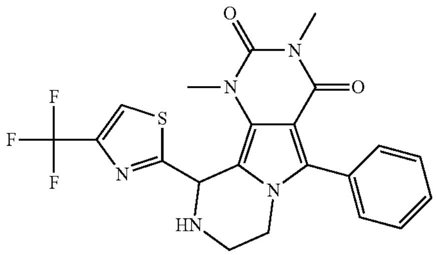 [SMILES: Cn1c(=O)c2c(-c3ccccc3)n3c(c2n(C)c1=O)C(c1nc(C(F)(F)F)cs1)NCC3] | 1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione | LCMS: Rt 0.94 min; 462 [M + H]+; 2minLC_v003; 1H NMR: (400 MHz, DMSO-d6) δ 8.49 (1H, s); 7.49-7.39 (5H, m); 6.11 (1H, d); 3.86-3.71 (3H, m); 3.48 (3H, s); 3.18 (3H, s); 3.15-3.07 (1H, m); 3.01-2.89 (1H, m). |
| 1.10 | 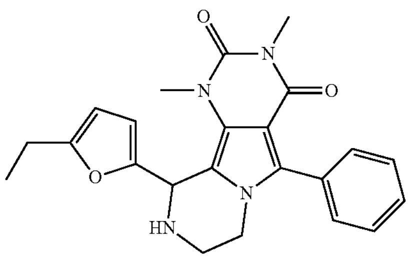 [SMILES: CCc1ccc(C2NCCn3c(-c4ccccc4)c4c(=O)n(C)c(=O)n(C)c4c32)o1] | 10-(5-Ethylfuran-2-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.89 min; 404 [M + H]+; 2minLC_v003; 1H NMR: (400 MHz, CDCl3) δ 7.50-7.44 (5H, m), 5.89 (1H, d), 5.81 (1H, d), 5.76 (1H, s), 3.93-3.83 (2H, m), 3.42 (3H, s), 3.35 (3H, s), 3.14-3.01 (2H, m), 2.67 (2H, q), 1.25 (3H, t). |
| 1.11 | 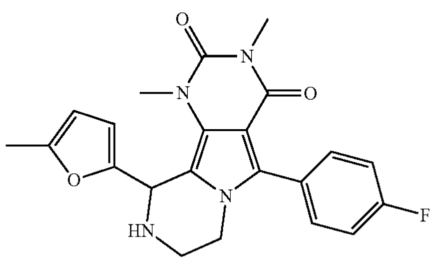 [SMILES: Cc1ccc(C2NCCn3c(-c4ccc(F)cc4)c4c(=O)n(C)c(=O)n(C)c4c32)o1] | 5-(4-Fluorophenyl)-1,3-dimethyl-10-(5-methylfuran-2-yl)-7,8,9,10-tetrahydropyrazino[1',2':1,2]pyrrolo[3,4-d]pyrimidine-2,4(1H,3H)-dione | LC-MS: Rt 0.87 min; 409 [M + H]+; 2minLC_v003. 1H NMR: (400 MHz, CDCl3) δ 7.44 (2H, dd), 7.18 (2H, t), 5.89 (1H, d), 5.81 (1H, d), 5.78 (1H, s), 3.91-3.87 (2H, m), 3.42 (3H, s), 3.35 (3H, s), 3.17-3.05 (2H, m), 2.32 (3H, s). |
| 1.12 | 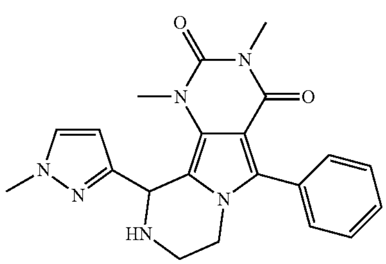 [SMILES: Cn1ccc(C2NCCn3c(-c4ccccc4)c4c(=O)n(C)c(=O)n(C)c4c32)n1] | 1,3-Dimethyl-10-(1-methyl-1H-pyrazol-3-yl)-5-phenyl-7,8,9,10-tetrahydropyrazino[1',2':1,2]pyrrolo[3,4-d]pyrimidine-2,4(1H,3H)-dione | LC-MS: Rt 0.76 min; 391 [M + H]+; 2minLC_v003; 1H NMR: (400 MHz, CDCl3) δ 7.48-7.43 (5H, m), 7.29 (1H, d), 5.89 (1H, d), 5.86 (1H, s), 3.99-3.91 (2H, m), 3.92 (3H, s), 3.37 (3H, s), 3.34 (3H, s), 3.19-3.13 (1H, m), 3.03 (1H, dt). |
| 1.13 | 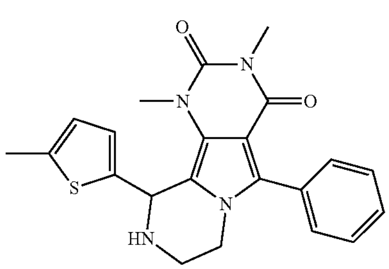 [SMILES: Cc1ccc(C2NCCn3c(-c4ccccc4)c4c(=O)n(C)c(=O)n(C)c4c32)s1] | 1,3-Dimethyl-10-(5-methylthiophen-2-yl)-5-phenyl-7,8,9,10-tetrahydropyrazino[1',2':1,2]pyrrolo[3,4-d]pyrimidine-2,4(1H,3H)-dione | LC-MS: Rt 0.87 min; 407 [M + H]+; 2minLC_v003; |

TABLE 1-continued

| Ex | Structure | Name | LCMS/NMR |
|---|---|---|---|
| 1.14 | 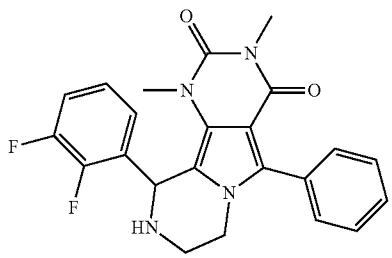 [SMILES: Cn1c(=O)c2c(-c3ccccc3)n3c(c2n(C)c1=O)C(c1cccc(F)c1F)NCC3] | 10-(2,3-Difluorophenyl)-1,3-dimethyl-5-phenyl-7,8,9,10-tetrahydropyrazino[1',2':1,2]pyrrolo[3,4-d]pyrimidine-2,4(1H,3H)-dione | LC-MS: Rt 0.87 min; 423 [M + H]+; 2minLC_v003; 1H NMR: (400 MHz, CDCl3) δ 7.55-7.45 (5H, m), 7.17 (1H, q), 7.03 (1H, m), 6.51 (1H, m), 6.18 (1H, s), 4.0-3.6 (2H, m), 3.33 (3H, s), 3.26 (3H, s), 3.04 (2H, s), 2.2 (1H, bs). |
| 1.15 | 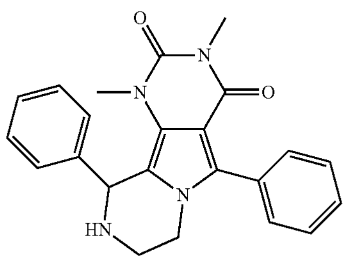 [SMILES: Cn1c(=O)c2c(-c3ccccc3)n3c(c2n(C)c1=O)C(c1ccccc1)NCC3] | 1,3-Dimethyl-5,10-diphenyl-7,8,9,10-tetrahydropyrazino[1',2':1,2]pyrrolo[3,4-d]pyrimidine-2,4(1H,3H)-dione | LC-MS: Rt 0.87 min; 387 [M + H]+; 2minLC_v003; 1H NMR: (400 MHz, DMSO-d6) δ 7.52-7.42 (5H, m), 7.35 (2H, t), 7.27 (1H, t), 7.17 (2H, d), 5.79 (1H, s), 3.85-3.74 (2H, m), 3.13 (3H, s), 3.12 (3H, s), 2.87-2.83 (1H, m), 2.78-2.72 (1H, m). |
| 1.16 | 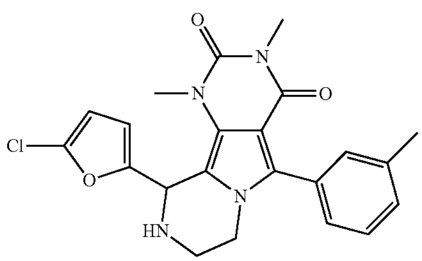 [SMILES: Cc1cccc(-c2c3c(=O)n(C)c(=O)n(C)c3c3n2CCNC3c2ccc(Cl)o2)c1] | 10-(5-Chlorofuran-2-yl)-1,3-dimethyl-5-(m-tolyl)-7,8,9,10-tetrahydropyrazino[1',2':1,2]pyrrolo[3,4-d]pyrimidine-2,4(1H,3H)-dione | LCMS: Rt 3.33 min; [M + H]+ 425; 10minLowpH 1H NMR: (400 MHz, DMSO-d6) δ 7.35 (1H, t), 7.30-7.20 (3H, m), 6.39 (1H, d), 6.07 (1H, d), 5.80 (1H, s), 3.83-3.63 (2H, m), 3.29 (3H, s), 3.15 (3H, s), 2.98-2.90 (1H, m), 2.8-2.77 (1H, m), 2.36 (3H, s). |
| 1.17 | 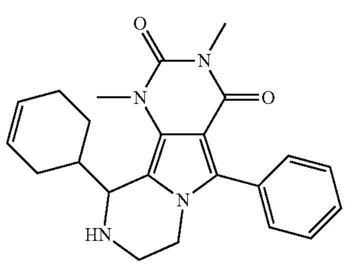 [SMILES: Cn1c(=O)c2c(-c3ccccc3)n3c(c2n(C)c1=O)C(C1CC=CCC1)NCC3] | 10-(Cyclohex-3-en-1-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.88 min; 390 [M + H]+; 2minLC_plates_v002; |
| 1.18 | 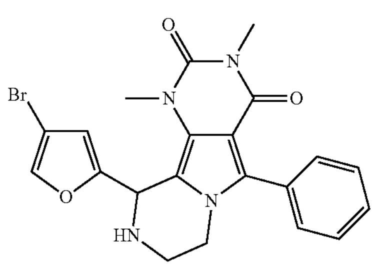 [SMILES: Cn1c(=O)c2c(-c3ccccc3)n3c(c2n(C)c1=O)C(c1cc(Br)co1)NCC3] | 10-(4-Bromofuran-2-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.88 min; 457 [M + H]+; 2minLC_v003; 1H NMR: (400 MHz, CDCl3) δ 7.51-7.43 (6H, m), 6.06 (1H, s), 5.82 (1H, s), 3.96-3.86 (2H, m), 3.42 (3H, s), 3.36 (3H, s), 3.09-3.06 (2H, m). |

TABLE 1-continued

| Ex | Structure | Name | LCMS/NMR |
|---|---|---|---|
| 1.19 | 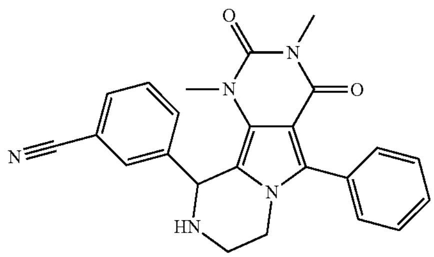 [SMILES: Cn1c(=O)c2c(-c3ccccc3)n3c(c2n(C)c1=O)C(c1cccc(C#N)c1)NCC3] | 3-(1,3-Dimethyl-2,4-dioxo-5-phenyl-1,2,3,4,7,8,9,10-octahydropyrazino[1',2':1,2]pyrrolo[3,4-d]pyrimidine-2,4(1H,3H)-dione | LCMS: Rt 0.83 min; 411 [M + H]+; 2minLC_plates_v002; |
| 1.20 | 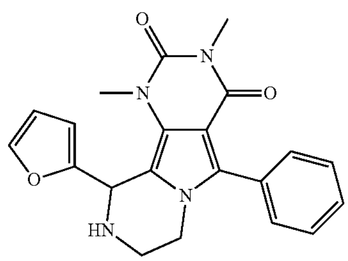 [SMILES: Cn1c(=O)c2c(-c3ccccc3)n3c(c2n(C)c1=O)C(c1ccco1)NCC3] | 10-(furan-2-yl)-1,3-dimethyl-5-phenyl-7,8,9,10-tetrahydropyrazino[1',2':1,2]pyrrolo[3,4-d]pyrimidin-10-yl)benzonitrile | LCMS: Rt 0.82 min; 377 [M + H]+; 2minLC_v003; 1H NMR: (400 MHz, DMSO-d6) δ 7.64 (1H, s), 7.47-7.42 (5H, m), 6.39 (1H, dd), 6.02 (1H, d), 5.80 (1H, s), 3.78-3.75 (2H, m), 3.25 (3H, s), 3.14 (3H, s), 3.12 (1H, br s), 2.96-2.87 (2H, m). |
| 1.21 | 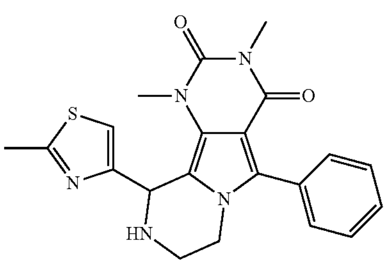 [SMILES: Cc1nc(C2NCCn3c(-c4ccccc4)c4c(=O)n(C)c(=O)n(C)c4c32)cs1] | 1,3-Dimethyl-10-(2-methylthiazol-4-yl)-5-phenyl-7,8,9,10-tetrahydropyrazino[1',2':1,2]pyrrolo[3,4-d]pyrimidine-2,4(1H,3H)-dione | LCMS: Rt 0.81 min; 408 [M + H]+; 2minLC_v003; 1H NMR: (400 MHz, CDCl3) δ 7.55-7.45 (5H, m), 6.61 (1H, s), 5.95 (1H, s), 3.99-3.90 (2H, m), 3.40 (3H, s), 3.37 (3H, s), 3.1 (1H, m), 2.95 (1H, m), 2.75 (3H, s). |
| 1.22 | 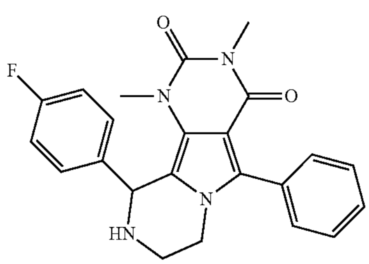 [SMILES: Cn1c(=O)c2c(-c3ccccc3)n3c(c2n(C)c1=O)C(c1ccc(F)cc1)NCC3] | 10-(4-Fluorophenyl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.9 min; 405 [M + H]+; 2minLC_v003; 1H NMR: (400 MHz, DMSO-d6) δ 7.51-7.42 (5H, m), 7.22-7.14 (4H, m), 5.79 (1H, s), 3.84-3.72 (2H, m), 3.13 (6H, s), 2.86-2.83 (1H, m), 2.75-2.69 (1H, m). |
| 1.23 | 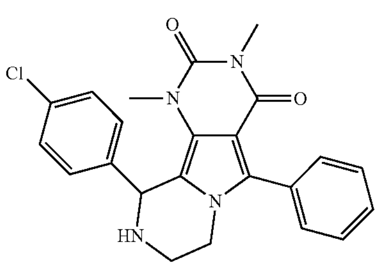 [SMILES: Cn1c(=O)c2c(-c3ccccc3)n3c(c2n(C)c1=O)C(c1ccc(Cl)cc1)NCC3] | 10-(4-Chlorophenyl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.92 min; 421 [M + H]+; 2minLC_v003; 1H NMR: (400 MHz, CDCl3) δ 7.52-7.45 (5H, m), 7.35 (2H, d), 7.12 (2H, d), 5.77 (1H, s), 3.95 (1H, dt), 3.86 (1H, dt), 3.35 (3H, s), 3.26 (3H, s), 3.00 (2H, dd). |

TABLE 1-continued

| Ex | Structure | Name | LCMS/NMR |
|---|---|---|---|
| 1.24 | 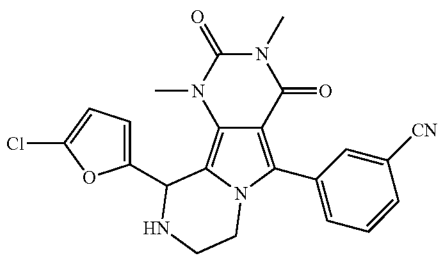 [SMILES: Cn1c(=O)c2c(-c3cccc(C#N)c3)n3c(c2n(C)c1=O)C(c1ccc(Cl)o1)NCC3] | 3-(10-(5-Chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile | LC-MS: Rt 0.78 mins [M + H]+ 436.0 (Method 2minLowpH) 1H NMR: (400 MHz, CDCl3) δ 7.75 (2H, obs t), 7.73 (1H, t), 7.62 (1H, t), 6.12 (1H, d), 5.94 (1H, dd), 5.79 (1H, s), 3.96-3.85 (2H, m), 3.44 (3H, s), 3.36 (3H, s), 3.11 (H, d), 3.09 (1H, d), 2.39 (1H, br s) |
| 1.25 | 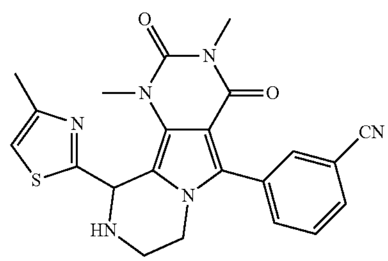 [SMILES: Cc1csc(C2NCCn3c(-c4cccc(C#N)c4)c4c(=O)n(C)c(=O)n(C)c4c32)n1] | 3-(1,3-Dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile | LC-MS: Rt 0.82 mins [M + H]+ 433.2 (Method 2minLowpH) 1H NMR: (400 MHz, CDCl3) δ 7.75 (2H, obs t), 7.78-7.23 (3H, m), 7.61 (1H, t), 6.89 (1H, s), 6.05 (1H, s), 5.79 (1H, s), 4.01-3.91 (2H, m), 3.44 (3H, s), 3.36 (3H, s), 3.25-3.11 (2H, m), 2.48 (3H, s) |
| 1.26 | 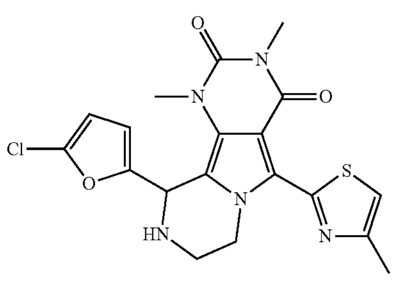 [SMILES: Cc1csc(-c2c3c(=O)n(C)c(=O)n(C)c3c3n2CCNC3c2ccc(Cl)o2)n1] | 10-(5-Chlorofuran-2-yl)-1,3-dimethyl-5-(4-methylthiazol-2-yl)-7,8,9,10-tetrahydropyrazino[1',2':1,2]pyrrolo[3,4-d]pyrimidine-2,4(1H,3H)-dione | LC-MS: Rt 0.83 mins [M + H]+ 433.4 (Method 2minLowpHv01) 1H NMR: (400 MHz, CDCl3) δ 7.08 (1H, d), 6.09 (1H, d), 5.93 (1H, dd), 5.79 (1H, s), 4.76 (1H, dt), 4.09 (1H, m), 3.43 (3H, s), 3.41 (3H, s), 3.13 (2H, dd), 2.52 (3H, obs d), 2.09 (1H, br s) |

The compounds of the following tabulated examples (Table 2) were prepared by a similar method to that of Example 1.1 from 6-(2-amino-ethyl)-1,3-dimethyl-5-phenyl-1,6-dihydro-pyrrolo[3,4-d]pyrimidine-2,4-dione (Intermediate A) or 3-(6-(2-aminoethyl)-1,3-dimethyl-2,4-dioxo-2,3,4,6-tetrahydro-1H-pyrrolo[3,4-d]pyrimidin-5-yl)benzonitrile (Intermediate Be) and a commercially available aldehyde. The resulting racemate was separated by SFC chromatographic resolution to yield single enantiomers.

TABLE 2

| Ex. | Structure Name | LCMS NMR SFC |
|---|---|---|
| 2.1 | 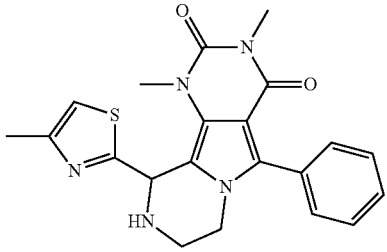<br>Enantiomer 1 of 1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione | LCMS: Rt 0.82 min; [M + H]+ 408; 2minLC_v003<br>1H NMR: (400 MHz, CDCl3) δ 7.50-7.43 (5H, m), 6.85 (1H, s), 5.99 (1H, s), 3.99-3.86 (2H, m), 3.42 (3H, s), 3.35 (3H, s), 3.17-3.04 (2H, m), 2.47 (3H, s).<br>SFC: Column: Chiralpak AD-H, 250 × 10 mm, 5 um (2 columns coupled together); Mobile phase: 35% 2-propanol + 0.1% DEA/65% CO2<br>Flow: 10 mL/min<br>Detection: UV @ 220 nm; Rt 5.13 min; >99.9% ee |
| 2.2 | 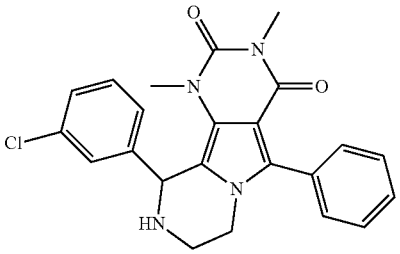<br>Enantiomer 1 of 10-(3-chlorophenyl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.90 min; [M + H]+ 421; 2minLC_v003<br>1H NMR: (400 MHz, CDCl3) δ 7.41-7.38 (5H, m), 7.22 (2H, d), 7.12 (1H, s), 6.95-6.92 (1H, m), 5.67 (1H, s), 3.88 (1H, dt), 3.80-3.73 (1H, m), 3.26 (3H, s), 3.18 (3H, s), 2.92-2.90 (2H, m).<br>SFC: Column: Chiralcel AD-H, 250 × 10 mm, 5 um. Mobile phase: 40% MeOH + 0.1% v/v DEA/60% $CO_2$.<br>Flow: 10 mL/min.<br>Detection: UV @ 220 nm; Rt 7.22 min; 98.5% ee |
| 2.3 | 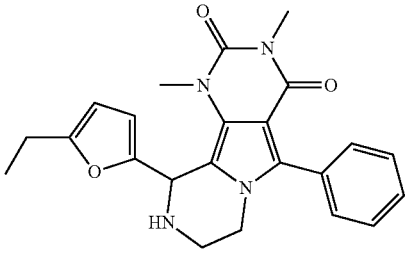<br>Enantiomer 1 of 10-(5-Ethylfuran-2-yl)-1,3-dimethyl-5-phenyl-7,8,9,10-tetrahydropyrazino[1',2':1,2]pyrrolo[3,4-d]pyrimidine-2,4-(1H,3H)-dione | LCMS: Rt 0.90 min; [M + H]+ 405; 2minLC_v003<br>1H NMR: (400 MHz, CDCl3) δ 7.39-7.34 (5H, m), 5.80 (1H, d), 5.72 (1H, d), 5.67 (1H, s), 3.85-3.74 (2H, m), 3.32 (3H, s), 3.26 (3H, s), 3.05-3.91 (2H, m), 2.58 (2H, q), 1.16 (3H, t).<br>SFC: Column: Chiralpak AD-H, 250 × 10 mm, 5 um.<br>Mobile phase: 30% MeOH/70% $CO_2$.<br>Flow: 10 mL/min.<br>Detection: UV @ 220 nm Rt 8.99 min; 97.2% ee |
| 2.4 | 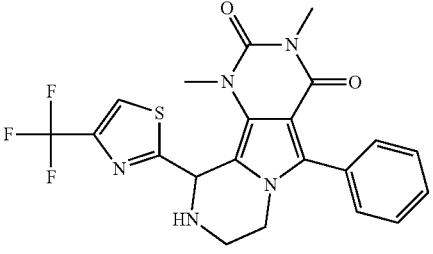<br>Enantiomer 1 of 1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione | LCMS: Rt 2.67 min; [M + H]+ 462; 10minLC_v003<br>1H NMR: (400 MHz, DMSO-d6) δ 8.49 (1H, s), 7.49-7.39 (5H, m), 6.11 (1H, d), 3.86-3.71 (3H, m), 3.48 (3H, s), 3.18 (3H, s), 3.15-3.07 (1H, m), 3.01-2.89 (1H, m).<br>SFC: Column: Chiralcel OJ-H 250 × 10 mm, 5 um<br>Mobile phase: 40% 2-propanol + 0.1% v/v DEA/60% $CO_2$<br>Flow: 10 mL/min<br>Detection: UV @ 220 nm; Rt 5.37 min; 99.8% ee |

TABLE 2-continued

| Ex. | Structure Name | LCMS NMR SFC |
|---|---|---|
| 2.5 | 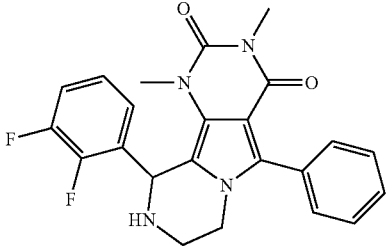<br>Enantiomer 1 of 10-(2,3-Difluorophenyl)-1,3-dimethyl-5-phenyl-7,8,9,10-tetrahydropyrazino[1',2':1,2]pyrrolo[3,4-d]pyrimidin-2,4(1H,3H)-dione | LCMS: Rt 0.85 min; [M + H]+ 423; 2minLC_v003<br>1H NMR: (400 MHz, CDCl3) δ 7.51-7.45 (5H, m), 7.20-7.14 (1H, m), 7.06-7.01 (1H, m), 6.51 (1H, t), 6.18 (1H, s), 4.03-3.88 (2H, m), 3.34 (3H, s), 3.27 (3H, s), 3.05-3.02 (2H, m), 2.26 (3H, bs).<br>SFC: Column: Chiralcel OD-H 250 × 10 mm, 5 um<br>Mobile phase: 35% Isopropanol/65% CO2<br>Flow: 10 mL/min<br>Detection: UV @ 220 nm; Rt 9.81 min; 98.2% ee |
| 2.6 | 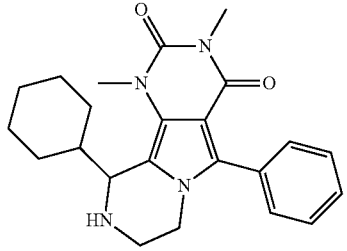<br>Enantiomer 1 of 10-Cyclohexyl-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.93 min; [M + H]+ 393; 2minLC_v003<br>1H NMR: (400 MHz, acetone) δ 7.52 (2H, d), 7.47-7.40 (3H, m), 4.56 (1H, d), 4.07-4.00 (1H, m), 3.74 (1H, dt), 3.55 (3H, s), 3.28 (1H, dt), 3.23 (3H, s), 2.99-2.93 (1H, m), 1.78-1.17 (11H, m).<br>SFC: Column: Chiralcel OD-H 250 × 10 mm, 5 um.<br>Mobile phase: 35% MeOH/65% CO2.<br>Flow: 10 mL/min.<br>Detection: UV @ 220 nm Rt 5.59 min; >99.9% ee |
| 2.7 | 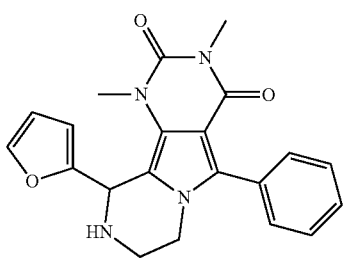<br>Enantiomer 1 of 10-(Furan-2-yl)-1,3-dimethyl-5-phenyl-7,8,9,10-tetrahydropyrazino[1',2':1,2]pyrrolo[3,4-d]pyrimidine-2,4(1H,3H)-dione | LCMS: Rt 0.82 min; [M + H]+ 377; 2minLC_v003<br>1H NMR: (400 MHz, CDCl3) δ 7.52-7.42 (6H, m), 6.33 (1H, dd), 5.97 (1H, d), 5.83 (1H, s), 3.97-3.85 (2H, m), 3.40 (3H, s), 3.36 (3H, s), 3.13-3.02 (2H, m).<br>SFC: Column: Chiralpak AD-H, 250 × 10 mm, 5 um.<br>Mobile phase: 30% MeOH/70% CO2.<br>Flow: 10 mL/min.<br>Detection: UV @ 220 nm; Rt 9.36 min; 98.1% ee |
| 2.8 | 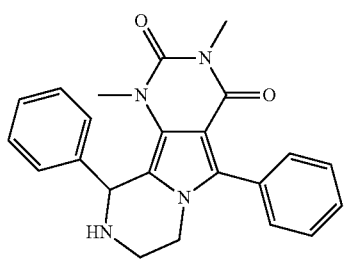<br>Enantiomer 1 of 1,3-Dimethyl-5,10-diphenyl-7,8,9,10-tetrahydropyrazino[1',2':1,2]pyrrolo[3,4-d]pyrimidine-2,4(1H,3H)-dione | LCMS: Rt 0.86 min; [M + H]+ 387; 2minLC_v003<br>1H NMR: (400 MHz, CDCl3) δ 7.42-7.34 (5H, m), 7.31-7.22 (3H, m), 7.08 (2H, d), 5.72 (1H, s), 3.91-3.77 (2H, m), 3.26 (3H, s), 3.16 (3H, s), 3.02-2.87 (2H, m).<br>SFC: Column: IC 4.6 × 100 mm.<br>Mobile Phase: 50% MeOH/50% CO2 + 0.2% DEA.<br>Detection: Diode array. Flow rate: 10 mL/min; Rt 6.38 min; >99.9% ee |

TABLE 2-continued

| Ex. | Structure Name | LCMS NMR SFC |
|---|---|---|
| 2.9 | 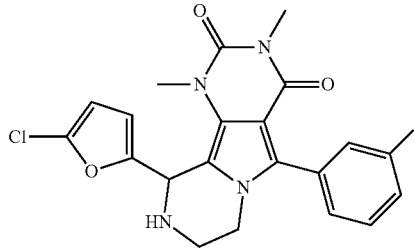Enantiomer 1 of 3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile | LC-MS: Rt 0.81 mins [M + H]+ 436.1<br>Method 2minLowpHv01<br>1H NMR: (400 MHz, CDCl3) δ 7.76-7.71 (3H, m), 7.61 (1H, t), 6.12 (1H, d), 5.94 (1H. dd), 5.78 (1H, s), 3.96-3.85 (2H, m), 3.45 (3H, s), 3.35 (3H, s), 3.09 (2H, dd), 2.40 (1H, br s).<br>SFC: Column: Chiralpak IA, 250 × 10 mm, 5 um @ 35degC<br>Mobile phase: 40% Methanol + 0.1% v/v DEA/60% CO2<br>Flow: 10 ml/min<br>Detection: UV @ 220 nm<br>SFC Rt = 7.88 mins Chiral purity >99% e.e. |
| 2.10 | 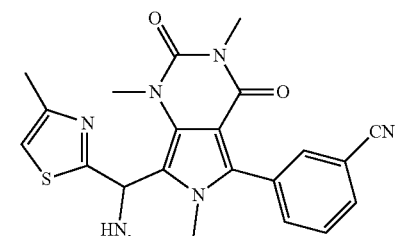Enantiomer 1 of 3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile | LC-MS: Rt 0.81 mins [M + H]+ 433.5<br>Method 2minLowpHv01<br>1H NMR: (400 MHz, CDCl3) δ 7.78-7.71 (3H, m), 7.61 (1H, t), 6.87 (1H, d), 5.99 (1H. s), 3.95-3.87 (2H, m), 3.43 (3H, s), 3.36 (3H, s), 3.21-3.07 (2H, m), 2.47 (3H, d).<br>SFC: Column: Chiralcel OJ-H 250 × 10 mm, 5 um<br>Mobile phase: 50% MeOH + 0.1% DEA/50% CO2<br>Flow: 10 ml/min<br>Detection: UV @ 220 nm<br>SFC Rt 2.63 mins Chiral purity 97% e.e. |

Example 3.1

10-(5-Chlorofuran-2-yl)-5-(3-chlorophenyl)-1,3-dimethyl-7,8,9,10-tetrahydropyrazino[1',2':1,2]pyrrolo[3,4-d]pyrimidine-2,4(1H,3H)-dione

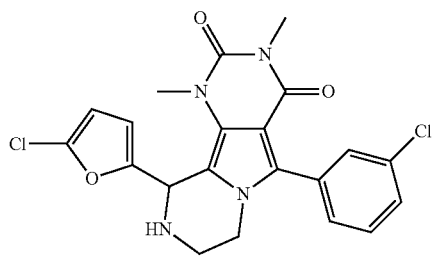 [SMILES: Cn1c(=O)c2c(-c3cccc(Cl)c3)n3c(c2n(C)c1=O)C(c1ccc(Cl)o1)NCC3]

6-(2-Amino-ethyl)-5-(3-chloro-phenyl)-1,3-dimethyl-1,6-dihydro-pyrrolo[3,4-d]pyrimidine-2,4-dione (Intermediate B) (150 mg, 0.451 mmol) and 5-chlorofuran-2-carbaldehyde (commercially available, 58.8 mg, 0.451 mmol) were suspended in ethanol (1.2 ml). The mixture was heated at 50° C. under microwave irradiation for 1 hour. TFA (4 drops) was added to the reaction mixture and heating continued at 60° C. for a further 30 mins under microwave irradiation. The reaction mixture was diluted with ethanol (0.5 mL) and purified using mass directed HPLC. The product containing fractions were combined and evaporated under reduced pressure to afford a white solid which was dried under vacuum at 50° C. for 16 h to afford the title compound as a pale tan solid;

LC-MS: Rt 0.86 mins; MS m/z 445/447/449 [M+H]+; (Method 2minLowpH).

1H NMR (400 MHz, CDCl₃) δ 7.46-7.40 (3H, m), 7.38-7.34 (1H, m), 6.12 (1H, d), 5.93 (1H, dd), 5.78 (1H, d), 3.94-3.84 (2H, m), 3.43 (3H, s), 3.36 (3H, s), 3.08 (2H, q), 2.31 (1H, br s)

The following tabulated compounds (Table 3) were prepared analogously to Example 3.1 from the appropriate starting compound (Intermediate B, Ba, Bb, Bc or Bd) and commercially available aldehyde.

TABLE 3

| Ex | Structure | Name | LCMS/NMR |
|---|---|---|---|
| 3.2 | 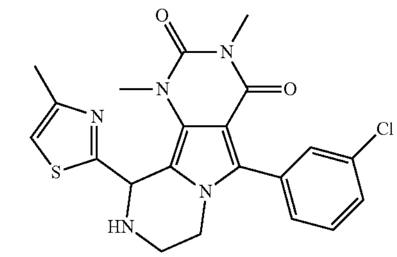 [SMILES: Cc1csc(C2NCCn3c(-c4cccc(Cl)c4)c4c(=O)n(C)c(=O)n(C)c4c32)n1] | 5-(3-Chlorophenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione | LCMS: Rt 0.87 mins; 442/444 [M + H]$^+$; Method 2minLowpH; 1H NMR (400 MHz, CDCl$_3$) δ 7.46-7.42 (3H, m), 7.41-7.36 (1H, m), 6.87 (1H, d), 5.99 (1H, s), 3.99-3.86 (2H, m), 3.43 (3H, s), 3.37 (3H, s), 3.20-3.06 (2H, m), 2.81 (3H, d) |
| 3.3 | 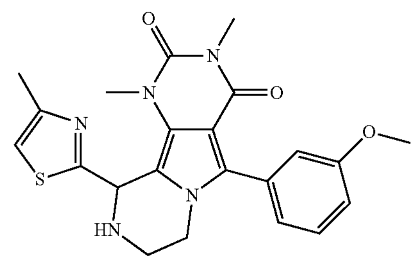 [SMILES: COc1cccc(-c2c3c(=O)n(C)c(=O)n(C)c3c3n2CCNC3c2nc(C)cs2)c1] | 5-(3-Methoxyphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione | LCMS: Rt 0.74 mins; 438.4 [M + H]$^+$; Method 2minLowpH_TFA; 1H NMR: (400 MHz, CDCl$_3$) δ 7.43-7.38 (1H, m), 7.04 (1H, dd), 7.02-6.98 (2H, m), 6.68 (1H, d), 6.00 (1H, s), 3.98 (1H, ddd), 3.95-3.88 (1H, m), 3.56 (3H, s), 3.43 (3H, s), 3.37 (3H, s), 3.19-3.04 (2H, m), 2.48 (3H, d). |
| 3.4 | 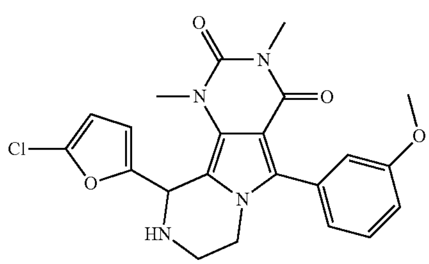 [SMILES: COc1cccc(-c2c3c(=O)n(C)c(=O)n(C)c3c3n2CCNC3c2ccc(Cl)o2)c1] | 10-(5-Chlorofuran-2-yl)-5-(3-methoxyphenyl)-1,3-dimethyl-7,8,9,10-tetrahydropyrazino[1',2':1,2]pyrrolo[3,4-d]pyrimidine-2,4(1H,3H)-dione | LCMS: Rt 0.75 mins; 441.4/443.4 [M + H]$^+$; Method 2minLowpH_TFA; 1H NMR: (400 MHz, CDCl$_3$) δ 7.40 (1H, t), 7.05-6.96 (3H, m), 6.11 (1H, d), 5.94 (1H, dd), 5.77 (1H, s), 3.97-3.87 (2H, m), 3.86 (3H, s), 3.43 (3H, s), 3.36 (3H, s), 3.06 (2H, dd). |
| 3.5 | 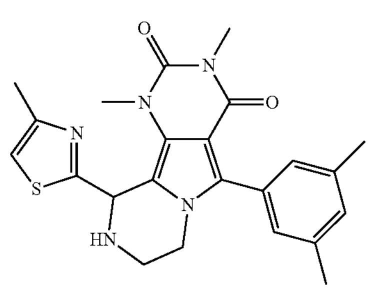 [SMILES: Cc1cc(C)cc(-c2c3c(=O)n(C)c(=O)n(C)c3c3n2CCNC3c2nc(C)cs2)c1] | 5-(3,5-Dimethylphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione | LCMS: Rt 0.81 mins; 436.5 [M + H]$^+$; Method 2minLowpH_TFA; 1H NMR: (400 MHz, CDCl$_3$) δ 7.08 (1H, s), 7.05 (2H, s), 6.86 (1H, s), 5.98 (1H, s), 3.94 (1H, ddd), 3.85 (1H, td), 3.42 (3H, s), 3.36 (3H, s), 3.13 (1H, td), 3.05 (1H, ddd), 2.48 (3H, s), 2.38 (6H, s). |

TABLE 3-continued

| Ex | Structure | Name | LCMS/NMR |
|---|---|---|---|
| 3.6 | 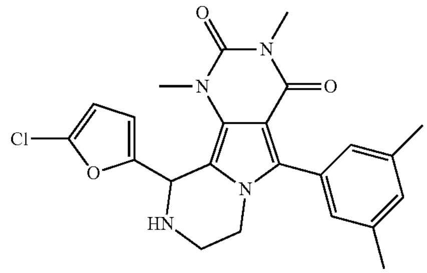 [SMILES: Cc1cc(C)cc(-c2c3c(=O)n(C)c(=O)n(C)c3c3n2CCNC3c2ccc(Cl)o2)c1] | 10-(5-Chlorofuran-2-yl)-5-(3,5-dimethylphenyl)-1,3-dimethyl-7,8,9,10-tetrahydropyrazino[1',2':1,2]pyrrolo[3,4-d]pyrimidine-2,4(1H,3H)-dione | LCMS: Rt 0.83 mins; 439.4/441.4 [M + H]+; Method 2minLowpH_TFA; [1] 1H NMR: (400 MHz, CDCl$_3$) δ 7.08 (1H, s), 7.03 (2H, s), 6.10 (1H, d), 5.92 (1H, dd), 5.76 (1H, s), 3.89 (1H, dt), 3.85-3.77 (1H, m), 3.43 (3H, s), 3.36 (3H, s), 3.08-3.03 (2H, m), 2.38 (6H, s). |
| 3.7 | 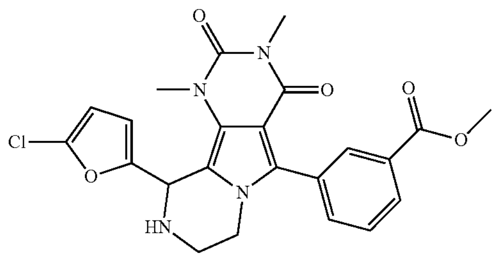 [SMILES: COC(=O)c1cccc(-c2c3c(=O)n(C)c(=O)n(C)c3c3n2CCNC3c2ccc(Cl)o2)c1] | Methyl 3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzoate | LCMS: Rt 0.79 min; 469/471 [M + H]+; Method 2minLowpH; 1H NMR: (400 MHz, CDCl$_3$) δ 8.16-8.10 (2H, m), 7.70 (1H, dt), 7.59 (1H, t), 6.13 (1H, d), 5.96 (1H, d), 5.80 (1H, s), 3.95 (3H, s), 3.92 (2H, t), 3.44 (3H, s), 3.36 (3H, s), 3.13-3.07 (2H, m). |
| 3.8 | 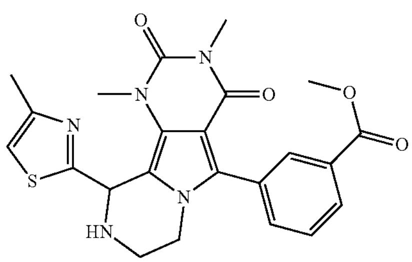 [SMILES: COC(=O)c1cccc(-c2c3c(=O)n(C)c(=O)n(C)c3c3n2CCNC3c2nc(C)cs2)c1] | Methyl 3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzoate | LCMS: Rt 0.80 mins; 466 [M + H]+; Method 2minLowpH; 1H NMR: (400 MHz, CDCl$_3$) δ 8.16-8.11 (2H, m), 7.71 (1H, dt), 7.59 (1H, t), 6.78 (1H, d), 6.01 (1H, s), 3.97-3.92 (5H, m), 3.44 (3H, s), 3.36 (3H, s), 3.21-3.00 (2H, m), 2.49 (3H, d) |
| 3.9 | 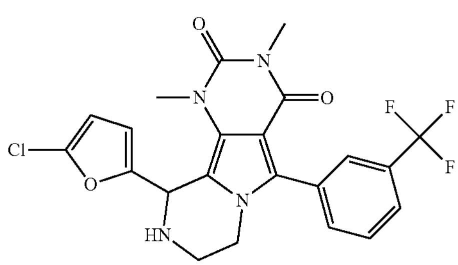 [SMILES: Cn1c(=O)c2c(-c3cccc(C(F)(F)F)c3)n3c(c2n(C)c1=O)C(c1ccc(Cl)o1)NCC3] | 10-(5-Chlorofuran-2-yl)-1,3-dimethyl-5-(3-(trifluoromethyl)phenyl)-7,8,9,10-tetrahydropyrazino[1',2':1,2]pyrrolo[3,4-d]pyrimidine-2,4(1H,3H)-dione | LCMS: Rt 0.91 mins; 479.4/481.3 [M + H]+; Method 2minLowpH; 1H NMR: (400 MHz, CDCl3) d 7.65-7.58 (3H, m), 7.54 (1H, t), 6.02 (1H, d), 5.86 (1H, dd), 5.71 (1H, s), 3.88-3.77 (2H, m), 3.35 (3H, s), 3.27 (3H, s), 3.04-2.99 (2H, m), 2.35 (1H, br s). |

Example 4.1

1,3-Dimethyl-10-(5-methylfuran-2-yl)-5-phenyl-7,8-dihydro-1H-pyrimido[4',5':3,4]pyrrolo[2,1-c][1,4]oxazine-2,4(3H,10H)-dione

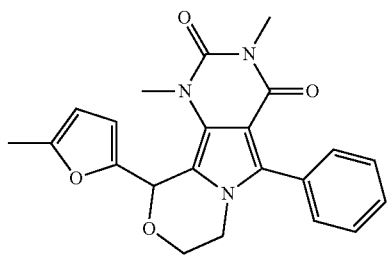

6-(2-Hydroxyethyl)-1,3-dimethyl-5-phenyl-1H-pyrrolo[3,4-d]pyrimidine-2,4(3H,6H)-dione (Int C) (244 mg, 0.815 mmol), bismuth triflate (50.9 mg, 0.082 mmol, 10 mol %) and EtOH (2.4 mL) were treated with 5-methylfuran-2-carbaldehyde (commercially available, 0.089 mL, 0.082 mmol). The mixture was heated to 100° C. for 10 min using microwave irradiation. A further portion of 5-methylfuran-2-carbaldehyde (25 µL) was added to the reaction mixture and heating continued at 100° C. for 5 min. A solid formed on cooling, which was collected by reduced pressure filtration and washed with EtOH followed by diethyl ether, affording the title compound.

1H NMR (400 MHz, CDCl$_3$) δ 7.49-7.45 (5H, m), 6.39 (1H, s), 6.01 (1H, d), 5.94 (1H, d), 4.03-3.87 (4H, m), 3.35 (3H, s), 3.32 (3H, s), 2.35 (3H, 5);

LC-MS Rt=1.13 min [M+H]+ 392 (Method 2min-LC_v003).

Chiral separation of the racemate by Supercritical Fluid Chromatography was carried out using the following conditions to afford the compounds listed hereinafter:

Mobile Phase: 50% MeOH/50% CO2
Column: Chiralcel OD-H 250×10 mm, 5 um
Detection: UV @ 220 nm
Flow rate: 10 mL/min
Sample concentration: 250 mg in 12 mL THF
Injection volume: 200 µl
Examples 4.2 and 4.3 are enantiomers.

Example 4.2

Enantiomer 2 Rt=2.97 min. of 1,3-dimethyl-10-(5-methylfuran-2-yl)-5-phenyl-7,8-dihydro-1H-pyrimido[4',5':3,4]pyrrolo[2,1-c][1,4]oxazine-2,4(3H,10H)-dione $^1$H NMR (400 MHz, CDCl$_3$) δ 7.49-7.45 (5H, m), 6.39 (1H, s), 6.01 (1H, d), 5.95 (1H, d), 4.03-3.88 (4H, m), 3.36 (3H, s), 3.33 (3H, s), 2.35 (3H, s);
LC-MS Rt=1.12 min MS m/z 392 [M+H] (Method 2min-LC_v003).
Chiral purity >99% ee

Example 4.3

Enantiomer 1 Rt=4.21 min of 1,3-dimethyl-10-(5-methylfuran-2-yl)-5-phenyl-7,8-dihydro-1H-pyrimido[4',5':3,4]pyrrolo[2,1-c][1,4]oxazine-2,4(3H,10H)-dione Second eluted peak Rt=4.21 min.
$^1$H NMR (400 MHz, CDCl$_3$) δ 7.49-7.35 (5H, m), 6.30 (1H, s), 5.92 (1H, d), 5.86 (1H, d), 4.94-3.78 (4H, m), 3.27 (3H, s), 3.24 (3H, s), 2.26 (3H, s); LC-MS Rt=1.13 min, MS m/z 392 [M+H] (Method 2minLC_v003).
Chiral purity >99.9% ee The compounds of the following tabulated examples (Table 4) were prepared by a similar method to that of Example 4.1 from the appropriate alcohol (preparation described hereinafter) and commercially available aldehyde.

TABLE 4

| Ex | Structure | Name | LCMS NMR |
|---|---|---|---|
| 4.4 | 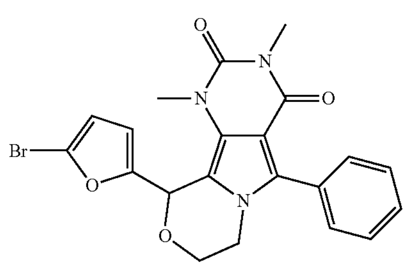 | 10-(5-Bromofuran-2-yl)-1,3-dimethyl-5-phenyl-7,8-dihydro-1H-pyrimido[4',5':3,4]pyrrolo[2,1-c][1,4]oxazine-2,4(3H,10H)-dione | LCMS: Rt: 4.99 min 456 [M + H]+; 10minLowpH 1HNMR: (400 MHz, CDCl3) δ 7.52-7.46 (5H, m), 6.41 (1H, s), 6.31 (1H, d), 6.12 (1H, dd), 4.02-3.91 (4H, m), 3.36 (3H, s), 3.34 (3H, s). |
| 4.5 | 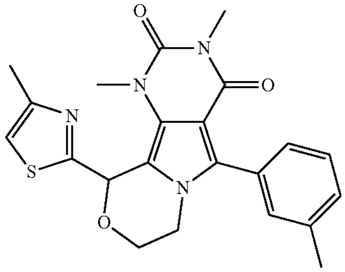 [SMILES: Cc1cccc(-c2c3c(=O)n(C)c(=O)n(C)c3c3n2CCOC3c2nc(C)cs2)c1] | 1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione | LCMS: Rt 1.12 min; [M + H]+ 423; 2minLowpH 1HNMR: (400 MHz, DMSO-d6/CDCl3) δ 7.32-7.19 (4H, m), 7.11 (1H, s), 6.68 (1H, s), 3.99-3.88 (4H, m), 3.31 (3H, s), 3.18 (3H, s), 2.36 (6H, s). |

TABLE 4-continued

| Ex | Structure | Name | LCMS NMR |
|---|---|---|---|
| 4.6 | ![structure] | 10-(3-Chlorophenyl)-1,3-dimethyl-5-(m-tolyl)-7,8-dihydro-1H-pyrimido[4',5':3,4]pyrrolo[2,1-c][1,4]oxazine-2,4(3H,10H)-dione | LCMS: Rt 1.27 min; [M + H]+ 436; 2minLC_v003 1HNMR: (400 MHz, DMSO-d6/CDCl3) δ 7.37-7.19 (7H, m), 7.11 (1H, m), 6.48 (1H, s), 3.90-3.89 (2H, m), 3.81-3.68 (2H, m), 3.18 (3H, s), 3.10 (3H, s), 2.37 (3H, s). |

Example 4.7

1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione

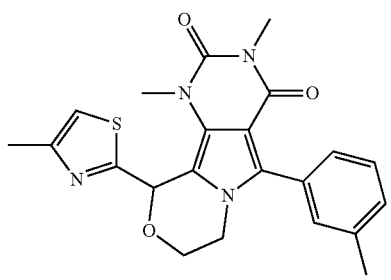 [SMILES: Cc1cccc(-c2c3c(=O)n(C)c(=O)n(C)c3c3n2CCOC3c2nc(C)cs2)c1]

The title compound was prepared analogously to Example 4.1 from the appropriate alcohol (preparation described hereinafter) and commercially available aldehyde. The racemate was separated by chiral SFC to afford the enantiomers;

Example 4.7.1

Enantiomer 1 of 1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione SFC Conditions:

Column: Chiralpak IB 250×10 mm, 5 um.

Mobile phase: 25% EtOH/75% $CO_2$.

Flow: 10 mL/min.

Column temperature: 35° C.

Detection: UV @ 220 nm. System: Berger Minigram SFC2

SFC Retention Time: Rt 9.46 min;

LCMS Rt 1.03 min; [M+H]+ 423; Method 2minLC_v003

1H NMR (400 MHz, CDCl3) δ 7.41-7.37 (1H, m), 7.29 (3H, m), 6.97 (1H, s), 6.65 (1H, s), 4.12-3.94 (4H, m), 3.38 (3H, s), 3.36 (3H, s), 2.50 (3H, s), 2.44 (3H, s)

>99.9% ee

Example 5.0

(7R)-1,3,7-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione

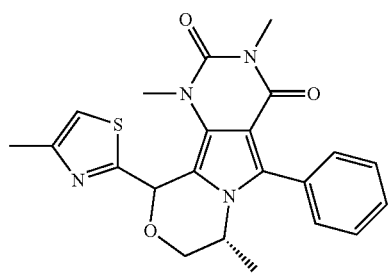 [SMILES: Cc1csc(C2OC[C@@H](C)n3c(-c4ccccc4)c4c(=O)n(C)c(=O)n(C)c4c32)n1]

6-((R)-2-Hydroxy-1-methyl-ethyl)-1,3-dimethyl-5-phenyl-1,6-dihydro-pyrrolo[3,4-d]pyrimidine-2,4-dione (Intermediate D) (195 mg, 0.622 mmol), bismuth triflate (38.8 mg, 0.062 mmol, 10 mol %) and 4-methylthiazole-2-carbaldehyde (commercial) (79 mg, 0.622 mmol) were combined in EtOH (2 mL) and the mixture heated at 120° C. under microwave irradiation for 3.5 hours. The reaction mixture was evaporated under reduced pressure. Purification of the residue by chromatography on silica, eluting with EtOAc/hexane afforded a mixture of diastereomeric compounds. Further purification by Supercritical Fluid Chromatography was carried out using the following conditions to afford Example 5.1

Mobile Phase: 40% MeOH/60% CO2
Column: CHIRALPAK AD 250×10 mm
Detection: UV @ 220-299 nm
Flow rate: 10 mL/min
Injection volume: 200 μl

Example 5.1

Diastereomer 1 of (7R)-1,3,7-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione SFC Retention Time=3.0 min 1H NMR (400 MHz, CDCl3) δ 7.44-7.37 (5H, m); 6.87 (1H, s); 6.56 (1H, s); 4.08-4.00 (1H, m); 3.82 (1H, dd, J 3.3 12.7); 3.54 (1H, dd, J 3.3 12.7); 3.29 (3H, s); 3.27 (3H, s); 2.39 (3H, s); 1.19 (3H, d, J 6.6).

LC-MS Rt=1.05 min MS m/z 423[M+H] (Method 2min-LowpH).

Chiral purity >99% de

Example 6.0

(8R,10R)-10-(5-Chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione

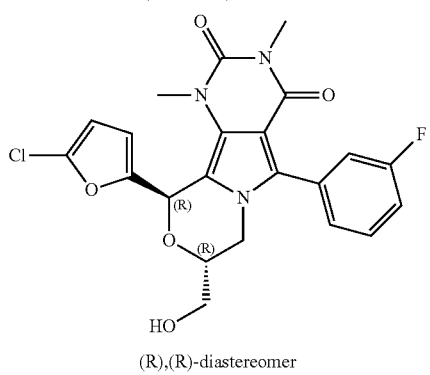

(R),(R)-diastereomer

Step 1: (R)-6-((2,2-Dimethyl-1,3-dioxolan-4-yl)methyl)-5-(3-fluorophenyl)-1,3-dimethyl-1H-pyrrolo[3,4-d]pyrimidine-2,4(3H,6H)-dione Sodium hydride (60% in mineral oil) (234 mg, 5.86 mmol) was added portionwise to a solution of 5-(3-fluorophenyl)-1,3-dimethyl-1H-pyrrolo[3,4-d]pyrimidine-2,4(3H,6H)-dione (Intermediate Gb) (1000 mg, 3.66 mmol) and dibenzo-18-crown-6 (132 mg, 0.366 mmol) in DMF (28.1 mL) at 0° C. The solution was warmed to room temperature and stirred for 20 minutes, then re-cooled to 0° C. (S)-(2,2-dimethyl-1,3-dioxolan-4-yl)methyltrifluoro methane sulfonate (Intermediate Ea) (1547 mg, 5.86 mmol) was added dropwise over 5 minutes. The mixture was warmed to room temperature and stirred for 3 hours. The reaction was quenched with saturated $NH_4Cl(aq)$ (10 mL) and extracted with DCM (3×30 mL). The combined organic extracts were dried over magnesium sulfate and evaporated under vacuum to afford the title compound as a red/brown amorphous solid.

LC-MS Rt 1.20 mins [M+H]+ 388.3 (Method 2minlowpHv03)

Step 2: (R)-6-(2,3-Dihydroxypropyl)-5-(3-fluorophenyl)-1,3-dimethyl-1H-pyrrolo[3,4-d]pyrimidine-2,4(3H,6H)-dione HCl (2 M in diethyl ether) (92 ml, 185 mmol) was added dropwise to a solution of (R)-6-((2,2-dimethyl-1,3-dioxolan-4-yl)methyl)-5-(3-fluorophenyl)-1,3-dimethyl-1H-pyrrolo[3,4-d]pyrimidine-2,4(3H,6H)-dione (step 1) (7.15 g, 18.46 mmol) and water (6.65 g, 369 mmol) in acetonitrile (35.1 mL). The mixture was stirred at room temperature for 30 minutes. Evaporation of the reaction mixture under vacuum afforded the title compound.

LCMS: Rt 0.85 mins [M+H]+ 348.3 (Method 2minlowpHV03).

Step 3: (8R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione A mixture of (R)-6-(2,3-dihydroxypropyl)-5-(3-fluorophenyl)-1,3-dimethyl-1H-pyrrolo[3,4-d]pyrimidine-2,4(3H,6H)-dione (step 2) (806 mg, 2.320 mmol), bismuth triflate (305 mg, 0.464 mmol) and 5-chlorofuran-2-carbaldehyde (commercial) (333 mg, 2.55 mmol) in ethanol (13.6 mL) was heated under microwave irradiation at 100° C. for 25 mins. The mixture was evaporated under vacuum. The residue was partitioned between 0.1 M HCl (50 mL) and DCM (100 mL) and extracted with DCM (3×100 mL). The combined organic extracts were dried over magnesium sulfate and evaporated under vacuum. Purification by chromatography on silica, eluting with 0-60% EtOAc/hexane afforded the title compound as a mixture of diastereomers.

LCMS Rt 1.19 mins [M+H]+ 460.4 (Method 2minlowpHv03)

Step 4: (8R,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione Separation of the diastereomeric mixture of (8R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione by SFC under the following conditions afforded the title compound.

Column: Chiralcel OD-H 250×10 mm, 5 μm
Mobile phase: 40% isopropanol/60% CO2
Flow rate: 100 mL/min
Detection: UV @ 220 nm
Rt=2.90 mins $^1$H NMR (400 MHz, CDCl$_3$): δ 7.50-7.45 (1H, m), 7.30-7.23 (2H, m), 7.21-7.15 (1H, m), 6.47 (1H, s), 6.16 (1H, d), 6.12 (1H, d), 4.08-3.98 (1H, d), 3.86-3.78 (3H, m), 3.72-3.66 (1H, m), 3.37 (6H, s)

LCMS Rt 1.19 mins [M+H]+ 460.4 (Method 2minlowpHv03)

Chiral purity >99% d.e.

The title compound may also be prepared from (2,2-dimethyl-1,3-dioxolan-4-yl)methyl trifluoromethanesulfonate (Intermediate Eb) in place of (S)-(2,2-dimethyl-1,3-dioxolan-4-yl)methyl trifluoromethanesulfonate (Intermediate Ea) and resolving the final mixture of diastereomers by SFC.

Example 6.1

3-((8R,10R)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8R,10S)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile

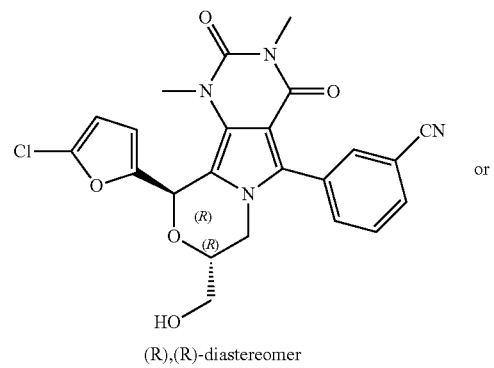

(R),(R)-diastereomer or

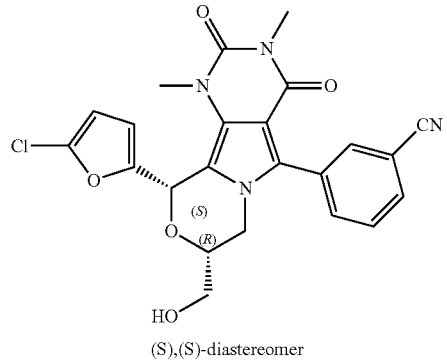

(S),(S)-diastereomer

The title compound was prepared by an analogous method to Example 6.0 replacing 5-(3-fluorophenyl)-1,3-dimethyl-1H-pyrrolo[3,4-d]pyrimidine-2,4(3H,6H)-dione (Intermediate Gb) (step 1) with 3-(1,3-Dimethyl-2,4-dioxo-2,3,4,6-tetrahydro-1H-pyrrolo[3,4-d]pyrimidin-5-yl)benzonitrile (Intermediate Ga) and purifying the final mixture of diastereomers by SFC under the following conditions:

Separation conditions;
Column: Chiralpak AD-H 250×10 mm, 5 μm
Mobile phase: 25% methanol/75% CO2
Flow rate: 10 mL/min
Detection: UV @ 220 nm
Rt=8.01 mins
1H NMR (400 MHz, DMSO-d6): δ 8.04 (1H, s), 7.95-7.91 (1H, m), 7.90-7.86 (1H, m), 7.71-7.67 (1H, m), 6.69 (1H, s), 6.50 (1H, d), 6.35 (1H, d), 4.92 (1H, t), 3.94-3.83 (3H, m), 3.55-3.42 (2H, m), 3.25 (3H, s), 3.17 (3H, s).
LCMS Rt 1.14 mins [M+H]+ 467.4 (Method 2min-lowpH03)
Chiral purity >99% d.e.

Example 7.0a and Example 7.0b (8S,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione or (8S,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione or (8R,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione or (8R,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione

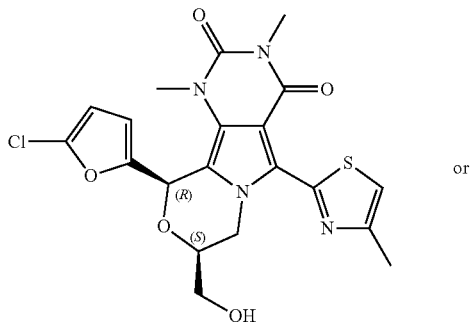

(8S,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione or

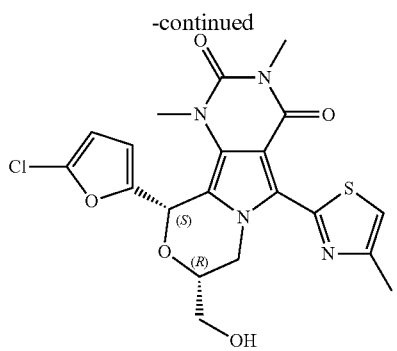

(8R,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione

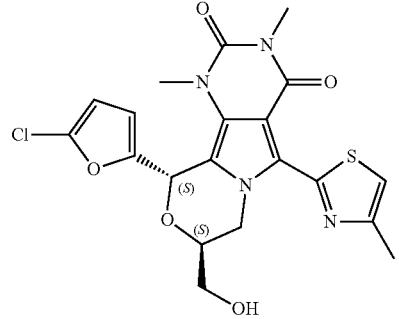

(8S,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione or

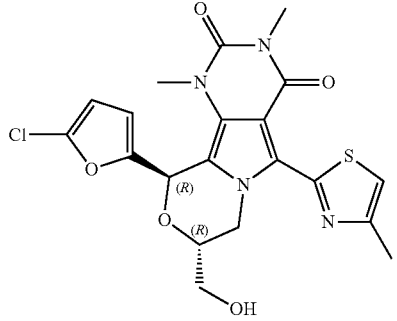

(8R,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Step 1

6-((2,2-Dimethyl-1,3-dioxolan-4-yl)methyl)-1,3-dimethyl-5-(4-methylthiazol-2-yl)-1H-pyrrolo[3,4-d]pyrimidine-2,4(3H,6H)-dione Sodium hydride (60% in mineral oil, 0.417 g, 10.42 mmol) was added to a solution of 1,3-dimethyl-5-(4-methylthiazol-2-yl)-1H-pyrrolo[3,4-d]pyrimidine-2,4(3H,6H)-dione (Intermediate Gc) (1.8 g, 6.51 mmol) and dibenzo-18-crown-6 (0.235 g, 0.651 mmol) in DMF (65.1 mL) at 0° C. The mixture was warmed to room temperature and stirred for 20 minutes, then re-cooled to 0° C. (2,2-Dimethyl-1,3-dioxolan-4-yl)methyl trifluoro methanesulfonate (Intermediate Eb) (3.44 g, 9.77 mmol) was then added dropwise. The mixture was stirred at 0° C. for 30 minutes and at room temperature for 16 hours. The reaction was quenched with water (50 mL) and extracted with DCM (3×50 mL). The combined organic extracts were dried over magnesium sulfate and evaporated under vacuum. Purification by chromatography on silica, eluting with EtOAc/hexane mixture afforded the title compound.

LC-MS Rt 1.15 mins [M+H]+ 392.3 (Method 2minlowpHv03)

Step 2: 6-(2,3-Dihydroxypropyl)-1,3-dimethyl-5-(4-methylthiazol-2-yl)-1H-pyrrolo[3,4-d]pyrimidine-2,4 (3H,6H)-dione 2M HCl in Et$_2$O (5.36 ml, 10.71 mmol) was added dropwise to a solution of 6-((2,2-dimethyl-1,3-dioxolan-4-yl)methyl)-1,3-dimethyl-5-(4-methylthiazol-2-yl)-1H-pyrrolo[3,4-d]pyrimidine-2,4(3H,6H)-dione (470 mg, 1.071 mmol) in acetonitrile (10.7 ml) and water (386 mg, 21.43 mmol). The mixture was stirred at room temperature for 1 hour, then evaporated under vacuum to afford the title compound.

LC-MS Rt 0.84 mins [M+H]+ 351.3 (Method 2minLowpHv03)

Step 3: 10-(5-Chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4 (3H,10H)-dione A mixture of 6-(2,3-dihydroxypropyl)-1,3-dimethyl-5-(4-methylthiazol-2-yl)-1H-pyrrolo[3,4-d]pyrimidine-2,4(3H, 6H)-dione (450 mg, 1.284 mmol), 5-chlorofuran-2-carbaldehyde (184 mg, 1.413 mmol) and bismuth triflate (169 mg, 0.257 mmol) in ethanol (9.584 ml) was stirred at room temperature for 2.5 hours. TFA (310 μl) was added and the mixture heated under microwave radiation at 80° C. for 20 mins, then further heated under microwave radiation at 80° C. for 10 hours. The reaction was then concentrated to half-volume under vacuum, a further portion of bismuth triflate (169 mg, 0.257 mmol) and powdered molecular sieves (200 mg) were added and the mixture heated under microwave radiation at 80° C. for 10 hours. The mixture was evaporated under vacuum and the residue partitioned between EtOAc (100 ml) and saturated K$_2$CO$_3$(aq) (100 ml) The phases were separated and the aqueous phase was extracted with EtOAc (3×100 ml). The combined organic extracts were dried over sodium sulfate and evaporated under vacuum. Purification by chromatography on silica, eluting with 40-50% EtOAc/hexane afforded the title compound as a mixture of diastereomers.

LC-MS Rt 1.11 mins [M+H]+ 463.2 (Method 2minLowpHv03)

Step 4: Separation of diasteromeric mixture of 10-(5-Chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Separation of the diastereomeric mixture of 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione was carried out by SFC under the following conditions to afforded the following compounds:

Column: CHIRALPAK IC 250×10 mm 5 μm @ 33.8° C.
Gradient: isocratic 50% MeOH/50% scCO2
Flow: 10 ml/min
Detection: UV @ 220-260 nm Example 7.0a Diasteromer 1 of 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Rt=6.81 mins
1H NMR (400 MHz, DMSO-d6) δ 7.49 (1H, s), 6.72 (1H, s), 6.49 (1H, d), 6.38 (1H, d), 4.96 (1H, t), 4.66 (1H, d), 3.97-3.82 (2H, m), 3.60-3.47 (2H, m), 3.24 (3H, s), 3.22 (3H s), 2.45 (3H, s)

LC-MS Rt 1.17 mins [M+H]+ 463.2 (Method 2minLowpHv03)
Chiral purity >99% d.e.

Example 7.0b Diasteromer 2 of 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Rt=8.95 mins
1H NMR (400 MHz, DMSO-d6) δ 0.49 (1H, s), 6.72 (1H, s), 6.49 (1H, d), 6.38 (1H, d), 4.96 (1H, t), 4.66 (1H, d), 3.97-3.82 (2H, m), 3.60-3.47 (2H, m), 3.24 (3H, s), 3.22 (3H s), 2.45 (3H, s)

LC-MS Rt 1.12 mins [M+H]+ 463.1 (Method 2minLowpHv03)
Chiral purity >99% d.e.

The following examples were prepared in a similar manner to Examples 7.0a and 7.0b from the appropriate starting material in place of 1,3-dimethyl-5-(4-methylthiazol-2-yl)-1H-pyrrolo[3,4-d]pyrimidine-2,4(3H,6H)-dione and the appropriate commerically available aldehyde in the relevant steps. Purification of the diastereomeric mixtures was carried out by SFC under the listed conditions to afford the title compounds.

Example 7.1a and Example 7.1b (8S,10S)-10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione or (8S,10R)-10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione or (8R,10S)-10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione or (8R,10R)-10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione

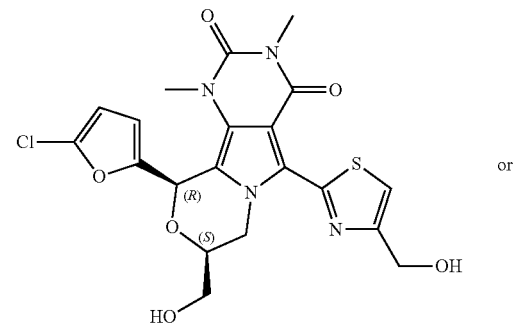

(8S,10R)-10-(5-chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione -continued

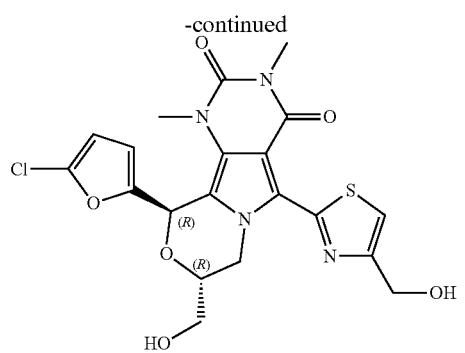

(8R,10R)-10-(5-chlorofuran-2-yl)-8-(hydroxymethyl)-
5-(4-hydroxymethyl)thiazol-2-yl)-1,
3-dimethyl-7,8-dihydro-1H-
pyrimido[4',5':3,4]pyrrolo[2,1-c][1,4]oxazine-
2,4(3H,10H)-dione

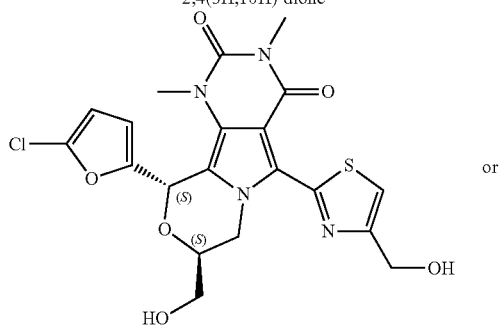

(8S,10S)-10-(5-chlorofuran-2-yl)-8-(hydroxymethyl)-
5-(4-(hydroxymethyl)thiazol-2-yl)-1,3-
dimethyl-7,8-dihydro-1H-pyrimido[4',5':3,4]pyrrolo
[2,1-c][1,4]oxazine-2,4(3H,10H)-dione or

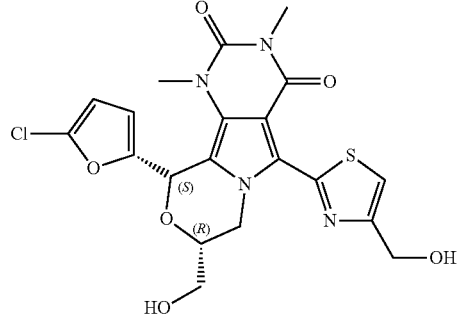

(8R,10S)-10-(5-chlorofuran-2-yl)-8-
(hydroxymethyl)-5-(4-hydroxymethyl)thiazol-2-yl)-
1,3-dimethyl-7,8-dihydro-1H-pyrimido
[4',5':3,4]pyrrolo[2,1-c][1,4]oxazine-2,4(3H,10H)-dione The individual diastereomer were purified as indicated below;

Example 7.1a

Diastereomer 1 of 10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione Column: Phenomenex LUX C4 250×10 mm, 5 um @ 35 deg C
Mobile phase: 50% Methanol/50% CO2
Flow: 10 ml/min
Detection: UV @ 220 nm
Rt=6.41 mins 1H NMR (400 MHz, DMSO-d6) δ 7.64 (1H, s), 6.72 (1H, s), 6.49 (1H, d), 6.39 (1H d), 5.39 (1H, t), 4.96 (1H, t), 4.65 (3H, d), 3.96-3.82 (2H, m), 3.59-3.47 (2H, m), 3.24 (3H, s), 3.22 (3H, s).
LC-MS Rt 1.00 mins [M+H]$^+$ 479.3 (Method 2minLowpHv03)
Chiral purity >99% d.e.

Example 7.1 b

Diastereomer 2 of 10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione Column: Chiralpak ID 250×10 mm, 5 um @ 35 deg C
Mobile phase: 50% Methanol/50% CO2
Flow: 10 ml/min
Detection: UV @ 220 nm
Rt=3.56 mins 1H NMR (400 MHz, DMSO-d6) δ 7.63 (1H, s), 6.56 (1H, s), 6.50 (2H, q), 5.38 (1H, t), 5.03 (1H, t), 4.65 (2H, d), 4.43 (1H, dd), 4.08 (1H, dd), 3.93 (1H, m), 3.64-3.53 (2H, m), 3.21 (3H, s), 3.10 (3H, s)
LC-MS Rt 0.99 mins [M+H]$^+$ 497.2 (Method 2min-LowpH03)
Chiral purity >99% d.e

Example 7.2a and Example 7.2b (8S,10S)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8R,10S)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8S,10R)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8R,10R)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione

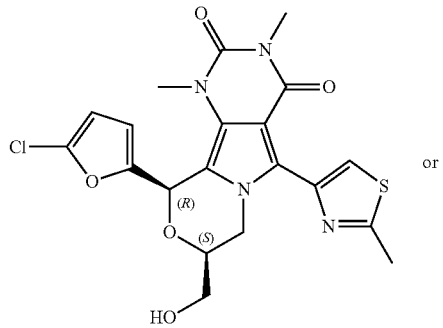

(8S,10R)-10-(5-chlorofuran-2-yl)-8-
(hydroxymethyl)-1,3-dimethyl-5-(2-
methylthiazol-4-yl)-
7,8-dihydro-1H-pyrimido[4',5':3,4]pyrrolo[2,1-
c][1,4]oxazine-2,4(3H,10H)-dione or

77
-continued

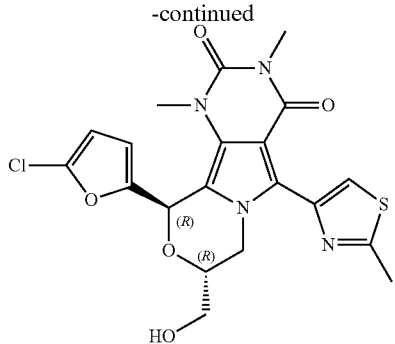

(8R,10R)-10-(5-chlorofuran-2-yl)-8-(hydroxymethyl)-
1,3-dimethyl-5-(2-methylthiazol-4-yl)-
7,8-dihydro-1H-pyrimido[4',5':3,4]pyrrolo[2,1-c]
[1,4]oxazine-2,4(3H,10H)-dione

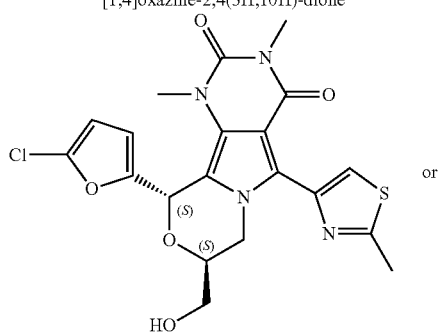

(8S,10S)-10-(5-chlorofuran-2-yl)-8-
(hydroxymethyl)-1,3-dimethyl-5-(2-methylthiazol-
4-yl)-7,8-dihydro-1H-
pyrimido[4',5':3,4]pyrrolo[2,1-c][1,4]
oxazine-2,4(3H,10H)-dione

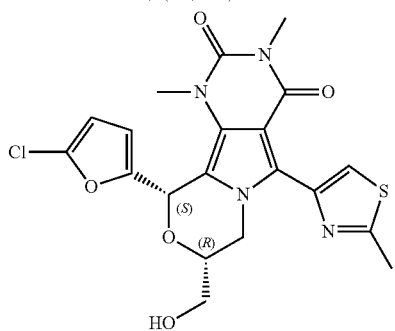

(8R,10S)-10-(5-chlorofuran-2-yl)-8-
(hydroxymethyl)-1,3-dimethyl-5-(2-methylthiazol-
4-yl)-7,8-dihydro-1H-pyrimido[4',5':3,4]pyrrolo
[2,1-c][1,4]oxazine-2,4(3H,10H)-dione Separation of the diastereomeric mixture was carried out by SFC under the following conditions to afforded the following compounds:
Column: Chiralpak AD-H, 250×10 mm, 5 um @ 35 deg C
Mobile phase: 50% Methanol/50% CO2
Flow: 10 ml/min
Detection: UV @ 220 nm

Example 7.2a

Diastereomer 1 of 10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione Rt=3.87 mins
1H NMR (400 MHz, CDCl3): δ 7.88 (1H, s), 6.37 (1H, s), 6.08-6.02 (2H, m), 4.57-4.48 (1H, m), 4.06-3.95 (2H, m), 3.74-3.60 (2H, m), 3.31 (6H, s), 2.60 (3H, s).

78

LC-MS Rt 1.10 mins [M+H]+ 463.2 (Method 2min-lowpH03)

Chiral purity >99% d.e.

Example 7.2b

Diastereomer 2 of 10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione Rt=2.42 mins
1H NMR (400 MHz, CDCl3): δ 8.18 (1H, s), 6.37 (1H, s), 6.23-6.17 (2H, m), 4.43-4.27 (2H, m), 4.10-4.03 (1H, m), 3.95-3.76 (2H, m), 3.40 (3H, s), 3.26 (3H, s), 2.83 (3H, s).

LC-MS Rt 1.09 mins [M+H]+ 463.3 (Method 2min-lowpH03)

Chiral purity >99% d.e.

Example 7.3a (8S,10S)-10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8R,10S)-10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8S,10R)-10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione or (8R,10R)-10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione

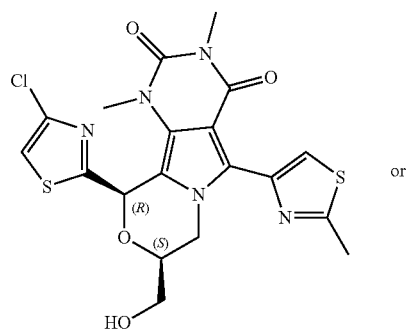

(8S,10R)-10-(4-chlorothiazol-2-yl)-8-
(hydroxymethyl)-1,3-dimethyl-5-(2-
methylthiazol-4-yl)-
7,8-dihydro-1H-pyrimido[4',5':3,4]pyrrolo[2,1-c]
[1,4]oxazine-2,4(3H,10H)-dione

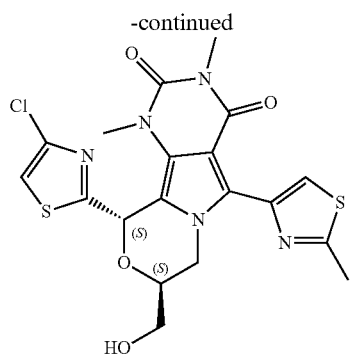

(8S,10S)-10-(4-chlorothiazol-2-yl)-8-
(hydroxymethyl)-1,3-dimethyl-5-(2-
methylthiazol-4-yl)-
7,8-dihydro-1H-pyrimido[4',5':3,4]pyrrolo[2,1-c]
[1,4]oxazine-2,4(3H,10H)-dione

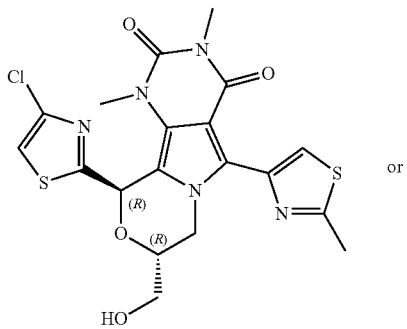

or (8R,10R)-10-(4-chlorothiazol-2-yl)-8-
(hydroxymethyl)-1,3-dimethyl-5-(2-
methylthiazol-4-yl)-
7,8-dihydro-1H-pyrimido[4',5':3,4]pyrrolo[2,1-c]
[1,4]oxazine-2,4(3H,10H)-dione

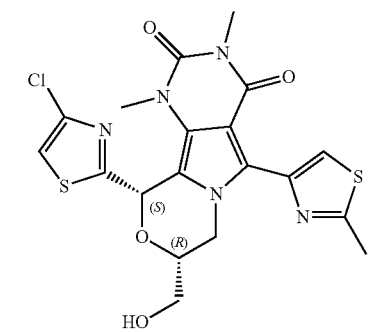

(8R,10S)-10-(4-chlorothiazol-2-yl)-8-
(hydroxymethyl)-1,3-dimethyl-5-(2-
methylthiazol-4-yl)-
7,8-dihydro-1H-pyrimido[4',5':3,4]pyrrolo[2,1-c]
[1,4]oxazine-2,4(3H,10H)-dione Separation of the diastereomeric mixture was carried out by SFC under the following conditions to afforded the title compound:

Separation conditions;

Column: Chiralpak AD-H 250×10 mm, 5 um @ 35 deg C

Mobile phase: 50% Methanol/50% CO2

Flow: 10 ml/min

Detection: UV @ 220 nm

Diasteroisomer 1 of 10-(4-Chlorothiazol-2-yl)-8-
(hydroxymethyl)-1,3-dimethyl-5-(2-methylthiazol-4-
yl)-7,8-dihydro-1H-pyrimido[4',5':3,4]pyrrolo[2,1-c]
[1,4]oxazine-2,4(3H,10H)-dione Rt=2.82 mins
1H NMR (400 MHz, CDCl3). δ 8.28 (1H, s), 7.15 (1H, s), 6.69 (1H, s), 4.63 (1H, d), 4.33-4.25 (1H, m), 4.14 (1H, s), 3.99 (1H, dd), 3.85 (1H, dd), 3.58 (3H, s), 3.42 (3H, s), 2.81 (3H, s).
LC-MS Rt 1.07 mins [M+H]$^+$ 480.3 (Method 2min-lowpH03)
Chiral purity >99% d.e.

Example 8.0a (8R,10S)-5-(3-Chlorophenyl)-10-(4-chlorothiazol-2-
yl)-8-(hydroxymethyl)-1,3-dimethyl-7,8-dihydro-
1H-pyrimido[4',5':3,4]pyrrolo[2,1-c][1,4]oxazine-2,4
(3H,10H)-dione or (8R,10R)-5-(3-Chlorophenyl)-10-(4-chlorothiazol-2-
yl)-8-(hydroxymethyl)-1,3-dimethyl-7,8-dihydro-
1H-pyrimido[4',5':3,4]pyrrolo[2,1-c][1,4]oxazine-2,4
(3H,10H)-dione

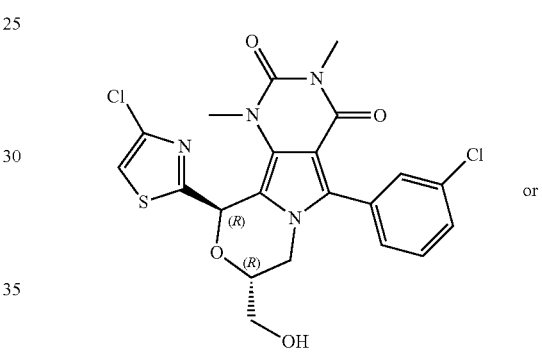

or (8R,10R)-5-(3-chlorophenyl)-10-(4-chlorothiazol-
2-yl)-8-(hydroxymethyl)-1,3-dimethyl-7,8-
dihydro-1H-pyrimido[4',5':3,4]pyrrolo
[2,1-c][1,4]oxazine-2,4(3H,10H)-dione

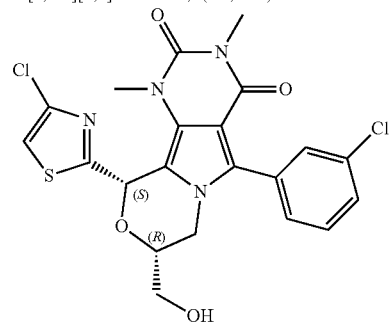

(8R,10S)-5-(3-chlorophenyl)-10-(4-chlorothiazol-
2-yl)-8-(hydroxymethyl)-1,3-dimethyl-7,8-
dihydro-1H-pyrimido[4',5':3,4]pyrrolo
[2,1-c][1,4]oxazine-2,4(3H,10H)-dione Step 1: 6-(Bromomethyl)-5-(3-chlorobenzoyl)-1,3-
dimethylpyrimidine-2,4(1H,3H)-dione The title compound was prepared analogously to 5-benzoyl-6-(bromomethyl)-1,3-dimethyl-1H-pyrimidine-2,4-dione (Intermediate A step 3) replacing benzoyl chloride with 3-chlorobenzoyl chloride in step 2.
LCMS Rt 1.23 mins [M+H]$^+$ 373.4 (Method 2minlowpHv03)

Step 2: (R)-5-(3-Chlorophenyl)-6-(2,3-dihydroxypropyl)-1,3-dimethyl-1H-pyrrolo[3,4-d]pyrimidine-2,4(3H,6H)-dione A mixture of 6-(bromomethyl)-5-(3-chlorobenzoyl)-1,3-dimethylpyrimidine-2,4(1H,3H)-dione (2 g, 5.38 mmol), (R)-3-aminopropane-1,2-diol (0.490 g, 5.38 mmol) and triethylamine (0.750 ml, 5.38 mmol) in EtOH (17.94 ml) was heated under microwave irradiation at 100° C. for 1 hour. The mixture was evaporated under vacuum and the residue partitioned between DCM (20 mL) and 1M HCl (20 mL). The phases were separated and the organic phase was washed with water (2×20 mL). The organic phase was passed through a hydrophobic frit and evaporate under vacuum to afford the title compound.

1H NMR (400 MHz, CDCl3) δ 7.44 (3H, m), 7.37 (1H, m), 6.58 (1H, br s), 4.02 (2H, t), 3.94 (1H, m), 3.61 (1H, dd), 3.43 (4H, m), 3.36 (3H, s)

LC-MS Rt 0.84 mins [M+H]+ 364.2 (Method 2minLowpHv01)

Step 3: (R)-6-(3-((tert-Butyldimethylsilyl)oxy)-2-hydroxypropyl)-5-(3-chlorophenyl)-1,3-dimethyl-1H-pyrrolo[3,4-d]pyrimidine-2,4(3H,6H)-dione A solution of (R)-5-(3-chlorophenyl)-6-(2,3-dihydroxypropyl)-1,3-dimethyl-1H-pyrrolo[3,4-d]pyrimidine-2,4 (3H,6H)-dione (1.39 g, 3.8 mmol), tert-butylchlorodimethylsilane (633 mg, 4.2 mmol), imidazole (520 mg, 7.6 mmol) and DMAP (47 mg, 0.38 mmol) in DMF (14 mL) was stirred at room temperature for 2 hours. A further portion of tert-butylchlorodimethylsilane (172 mg, 1.1 mmol) was added and the mixture stirred for a further 1 hour. The reaction mixture was diluted with EtOAc (70 mL) and washed with 0.5M HCl (3×35 mL) and brine (1×35 mL). The organic phase was dried over magnesium sulfate and evaporated under vacuum. Trituration with hexane afforded the title compound.

LC-MS Rt 1.41 mins [M+H]+ 478.4 (Method 2minLowpHv01)

Step 4: (8R)-5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione HCl in dioxane (0.654 ml, 2.61 mmol) was added to a suspension of (R)-6-(3-((tert-butyldimethylsilyl)oxy)-2-hydroxypropyl)-5-(3-chlorophenyl)-1,3-dimethyl-1H-pyrrolo[3,4-d]pyrimidine-2,4(3H,6H)-dione (250 mg, 0.523 mmol), 4-chlorothiazole-2-carbaldehyde (Intermediate H) (85 mg, 0.575 mmol) and bismuth triflate (103 mg, 0.157 mmol) in anhydrous ethanol (4 ml) and the mixture heated at 50° C. for 36 hours. Further portions of HCl in dioxane (0.654 ml, 2.61 mmol) were added as necessary to allow the reaction to run to completion. The mixture was cooled to room temperature and diluted with EtOAc (50 ml) and water (20 ml). The phases were separated and the aqueous phase extracted with EtOAc (3×30 ml). The combined organic extracts were washed with saturated NaHCO3(aq) (20 ml), water (20 ml) and brine (20 ml), dried over sodium sulfate and evaporated under vacuum. Purification by chromatography on silica, eluting with 10-70% EtOAc/hexane afforded the title compound as a mixture of diastereomers.

LC-MS Rt 1.19/1.23 mins [M+H]+ 493.1 (Method 2min-LowpHv03)

Step 5: (8R,10(R or S))-5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione The diastereomeric mixture of (8R)-5-(3-chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione was separated using SFC under the following conditions to afford the title compound.
Column: Chiralpak AD-H, 250×10 mm, 5 um @ 35 deg C
Mobile phase: 40% Methanol+0.1% v/v DEA/60% CO2
Flow: 10 ml/min
Detection: UV @ 220 nm

Example 8.0a

Diastereomer 1 of 5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4] oxazine-2,4(3H,10H)-dione Rt=3.68 mins
1H NMR (400 MHz, DMSO-d6) δ 7.91 (1H, s), 7.62 (1H, s), 7.56-7.48 (3H, s), 6.99 (1H, s), 4.97 (1H, t), 3.96-3.85 (3H, m), 3.53 (1H, m), 3.46 (1H, m), 3.30 (3H, s), 3.18 (3H, s)
LC-MS Rt 1.20 mins [M+H]+ 493.1 (Method 2minLowpHv03)
Chiral purity >99% d.e.

A second diastereomer of 5-(3-chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4 (3H,10H)-dione was also isolated;
Rt=5.77 mins The following example was prepared in similar fashion to Example 8.0a using the appropriate commerically available aldehyde in step 4.

Example 8.1a (8R,10R)-10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4 (3H,10H)-dione or (8R,10S)-10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4 (3H,10H)-dione

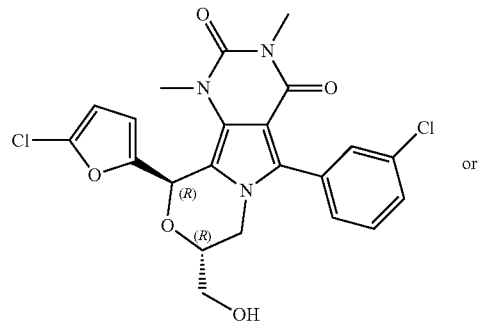

(8R,10R)-10-(5-chlorofuran-2-yl)-5-(3-chlorophenyl-8-(hydroxymethyl)-1,3-dimethyl-7,8-dihydro-1H-pyrimido[4',5':3,4]pyrrolo[2,1-c][1,4]oxazine-2,4(3H,10H)-dione

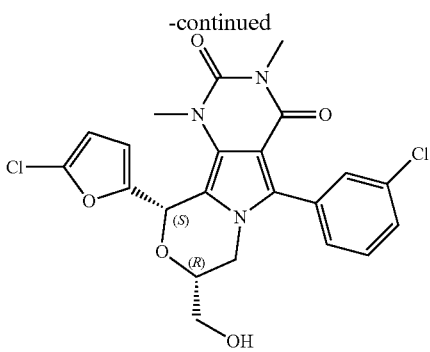

(8R,10S)-10-(5-chlorofuran-2-yl)-5-(3-chlorophenyl-8-(hydroxymethyl)-1,3-dimethyl-7,8-dihydro-1H-pyrimido[4',5':3,4]pyrrolo[2,1-c][1,4]oxazine-2,4(3H,10H)-dione Purification of the diastereomeric mixture by SFC under the following conditions yielded a single diastereomeric product.

Column: Phenomenex Lux-C2, 250×10 mm, 5 um @ 35 deg C
Mobile phase: 50% Methanol/50% CO2
Flow: 10 ml/min
Detection: UV @ 220 nm Diastereomer 1 of 10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione
Rt=10.53 mins
LC-MS Rt 1.25 mins [M+H]+ 476.3 (Method 2minlow-pHv03)
1H NMR (400 MHz, CDCl3) δ 7.45 (3H, m), 7.36 (1H, m), 6.47 (1H, s), 6.16 (1H, d), 6.12 (1H, d), 4.00 (1H, m), 3.94-3.77 (3H, s), 3.68 (1H, dd), 3.36 (6H, s)

Example 9a 3-((8S,10R)-10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8R,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8S,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile

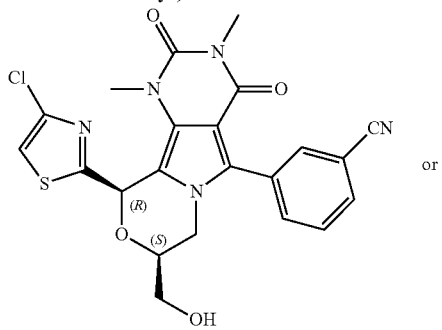

3-((8S,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or

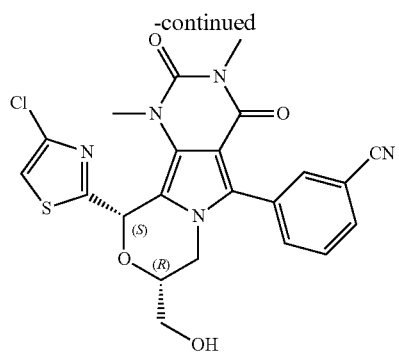

3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile

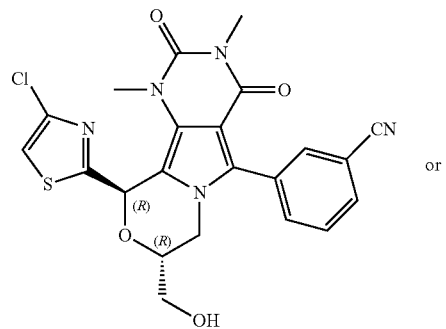

3-((8R,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or

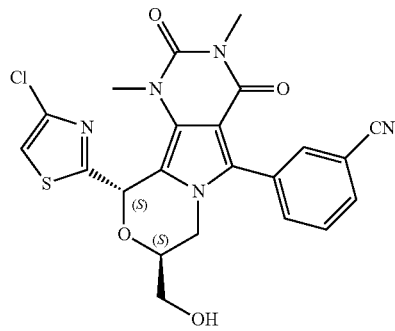

3-((8S,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile Step 1: 3-(6-(3-((tert-Butyldimethylsilyl)oxy)-2-hydroxypropyl)-1,3-dimethyl-2,4-dioxo-2,3,4,6-tetrahydro-1H-pyrrolo[3,4-d]pyrimidin-5-yl)benzonitrile The title compound was prepared by an analogous method to Example 8.0a step 3, using 3-(1,3-dimethyl-2,4-dioxo-2,3,4,6-tetrahydro-1H-pyrrolo[3,4-d]pyrimidin-5-yl)benzonitrile (Intermediate Ga) in place of 5-(3-fluorophenyl)-1,3-dimethyl-1H-pyrrolo[3,4-d]pyrimidine-2,4(3H,6H)-dione (Intermediate Gb) and racemic (2,2-dimethyl-1,3-dioxolan- 4-yl)methyl trifluoromethanesulfonate (Intermediate Eb) in place of (S)-(2,2-dimethyl-1,3-dioxolan-4-yl)methyl trifluoromethanesulfonate (Intermediate Ea) in step 1.

Step 2: 3-((8S,10R)-10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile and 3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile and 3-((8R,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile and 3-((8S,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile cis-isomers

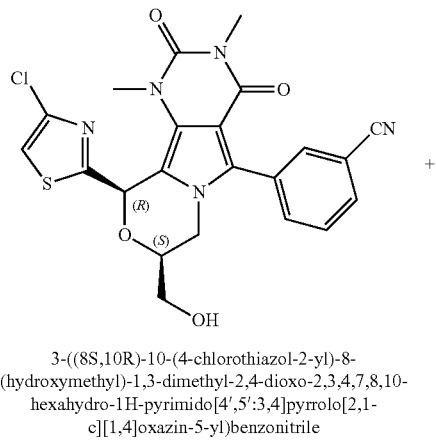

3-((8S,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile

+

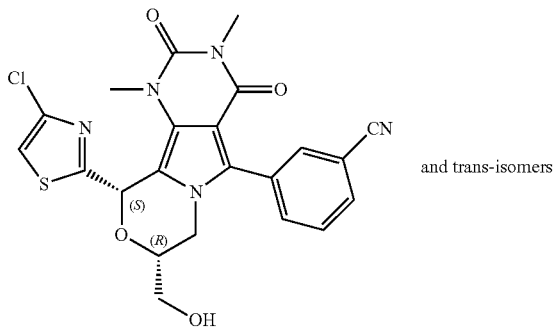

and trans-isomers 3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile -continued

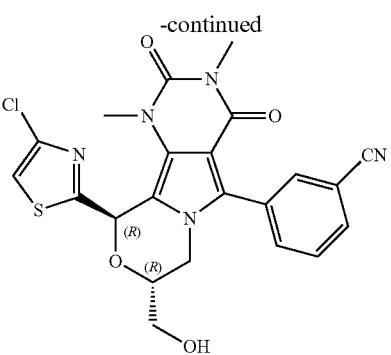

3-((8R,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile

+

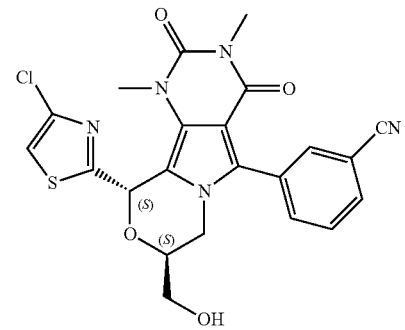

3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile HCl (4M in dioxane, 1067 µl, 4.27 mmol) was added to a solution of bismuth triflate (84 mg, 0.128 mmol), 4-chlorothiazole-2-carbaldehyde (Intermediate H) (69.3 mg, 0.469 mmol) and 3-(6-(3-((tert-butyldimethylsilyl)oxy)-2-hydroxypropyl)-1,3-dimethyl-2,4-dioxo-2,3,4,6-tetrahydro-1H-pyrrolo[3,4-d]pyrimidin-5-yl)benzonitrile (200 mg, 0.427 mmol) in ethanol (4268 µL). The mixture was stirred at room temperature for 2 hours and at 50° C. for 24 hours. The mixture was cooled to room temperature and diluted with DCM (10 mL) and 1M NaOH(aq) (10 mL). The phases were separated and the aqueous phase was extracted with DCM (3×10 mL). The combined organic extracts were dried over magnesium sulfate and evaporated under vacuum. Purification by mass-directed HPLC using the following conditions afforded two diastereomeric products.

Column: XSelect CSH Prep C18 column, 30×100 mm, 5 um.

Mobile phase: A=0.1% DEA in water, B=0.1% DEA in MeCN

Gradient:
0.0-0.5 min: 30% B 30 mL/min
0.5-1.0 min: 30% B 30-50 mL/min
1.0-7.2 min: 30-70% B, 7.2-7.3 min: 70-98% B, 7.3-9.4 min: 98% B
9.4-9.5 30% B 50 mL/min Diastereomer 1 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile First eluted peak.
LC-MS Rt 1.07 mins [M+H]+ 484.0 (Method 2minlowpHv03)

Diastereomer 2 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile Second eluted peak.
LC-MS Rt 1.10 mins [M+H]+ 484.2 (Method 2minlow-pHv03)

Step 3: 3-((8S,10R)-10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8R,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile or 3-((8S,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile The first eluted peak of step 2 was separated by SFC under the following conditions to afford one of the title enantiomeric products.
Column: Chiralcel OD-H 250×10 mm, 5 um @ 35 deg C
Mobile phase: 50% Methanol+0.1% v/v DEA/50% CO2
Flow: 10 ml/min
Detection: UV @ 220 nm Example 9a Diastereomer 1 of 3-(10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile Rt=3.75 mins
1H NMR (400 MHz, DMSO-d6): δ 8.04 (1H, s), 7.95-7.88 (3H, m), 7.71-7.68 (1H, m), 7.0 (1H, s), 4.97 (1H, t), 3.94-3.89 (3H, m), 3.57-3.44 (2H, m), 3.34-3.29 (6H, m).
Diethylamine present.
LC-MS Rt 1.06 mins [M+H]+ 484.1 (Method 2minlow-pHv03)
Chiral purity >99% d.e.
The second enantiomer was also isolated at Rt=4.93 mins.
The second eluted peak of Example 9a step 2 was separated by SFC under the following conditions to afford the title enantiomeric product.
Column: Chirapak AD-H 250×10 mm, 5 um @ 35 deg C
Mobile phase: 45% Methanol+0.1% v/v DEA/55% CO2
Flow: 10 ml/min
Detection: UV @ 220 nm Example 9b Diastereomer 2 of 3-(10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile Rt=2.90 mins.
1H NMR (400 MHz, DMSO-d6): δ 8.08 (1H, s), 7.95-7.90 (2H, m), 7.83 (1H, s), 7.72-7.67 (1H, m), 6.91 (1H, s), 5.06 (1H, t), 4.15-4.09 (1H, m), 3.95-3.89 (2H, m), 3.68-3.57 (2H, m), 3.50 (3H, s), 3.20 (3H, s).
LC-MS Rt 1.10 mins [M+H]+ 484.1 (Method 2minlow-pHv03)
Chiral purity >99% d.e.
Another diastereomer was also isolated at Rt=3.98 mins.
The following examples were prepared in a similar manner to example 6.0, using the appropriate starting material (Intermediate Gb) in place of 1,3-dimethyl-5-(4-methylthiazol-2-yl)-1H-pyrrolo[3,4-d]pyrimidine-2,4(3H,6H)-dione, and the appropriate commerically available aldehyde in the relevant steps. Purification of the diastereomeric mixtures was carried out by SFC under the listed conditions to afford the title compounds.

Examples 10a and 10b (8S,10S)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione or (8R,10R)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione or (8R,10S)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione or (8S,10R)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione

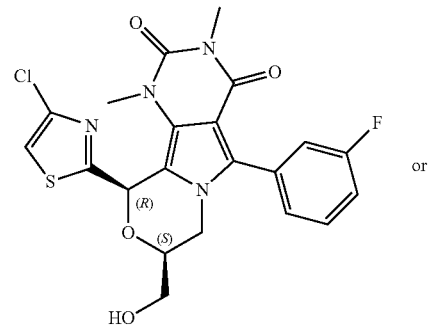

(8S,10R)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione -continued

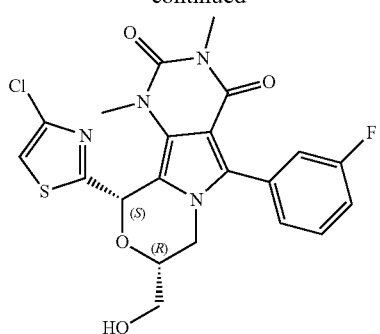

(8R,10S)-10-(4-chlorothiazol-2-yl)-5-
(3-fluorophenyl)-8-(hydroxymethyl)-
1,3-dimethyl-7,8-dihydro-1H-pyrimido[4',5':3,4]
pyrrolo[2,1-c][1,4]oxazine-2,4(3H,10H)-dione

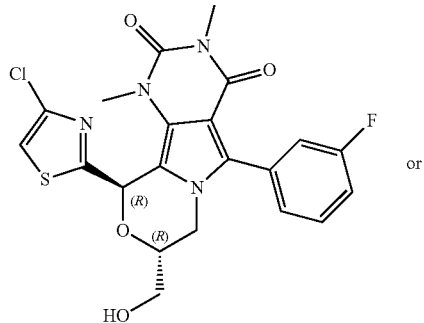

(8R,10R)-10-(4-chlorothiazol-2-yl)-5-
(3-fluorophenyl)-8-(hydroxymethyl)-
1,3-dimethyl-7,8-dihydro-1H-pyrimido[4',5':3,4]
pyrrolo[2,1-c][1,4]oxazine-2,4(3H,10H)-dione or

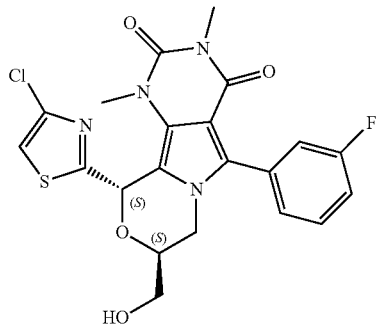

(8S,10S)-10-(4-chlorothiazol-2-yl)-5-
(3-fluorophenyl)-8-(hydroxymethyl)-
1,3-dimethyl-7,8-dihydro-1H-pyrimido[4',5':3,4]
pyrrolo[2,1-c][1,4]oxazine-2,4(3H,10H)-dione The title compounds were prepared by an analogous method to Example 9a and 9b from the appropriate starting compound (prepared analogously to Example 6 step 2 from Intermediate Eb and Intermediate Gb).

The first eluted diastereomer was separated by SFC under the following conditions to afford one of the title enantiomeric products Column: Chiralcel OD-H 250×10 mm, 5 um @ 35 deg C
Mobile phase: 45% Methanol/55% CO2
Flow: 10 ml/min
Detection: UV @ 220 nm Example 10a Diastereomer 1 of 10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione Rt=3.67 mins
1H NMR (400 MHz, CDCl3): δ 7.54-7.45 (1H, m), 7.31-7.16 (4H, m), 6.70 (1H, s), 4.13-4.05 (1H, m), 3.98-3.86 (2H, m), 3.84-3.67 (2H, m), 3.40 (3H, s), 3.36 (3H, s) 28 Mar. 2013
LC-MS Rt 2.54 mins [M+H]$^+$ 477.2 (5minhighpHv01)
Chiral purity >99% d.e.

The second eluted diastereomer was separated by SFC under the following conditions to afford one of the title enantiomeric products
Column: Chiralpak AD-H 250×10 mm, 5 um
Mobile phase: 45% Methanol/55% CO2
Flow: 10 ml/min
Detection: UV @ 220 nm Example 10b Diastereomer 2 of 10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione Rt=2.30 mins
1H NMR (400 MHz, CDCl3): δ 7.51-7.46 (1H, m), 7.31-7.16 (4H, m), 6.72 (1H, s), 4.18-4.10 (1H, m), 4.08-4.02 (1H, m), 3.97-3.92 (2H, m), 3.80-3.73 (1H, dd), 3.59 (3H, s), 3.39 (3H, s)
LC-MS Rt 1.15 mins [M+H]$^+$ 477.1 (Method 2min-lowpH03)
Chiral purity >99% d.e.

Example 11a (8R,10R)-10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione or (8S,10S)-10-(5-chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione

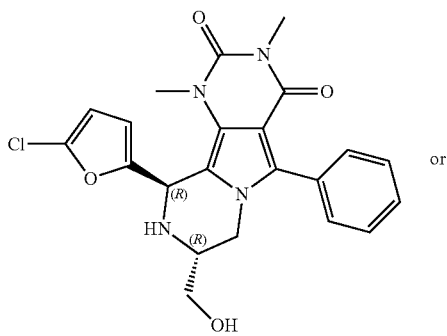

or

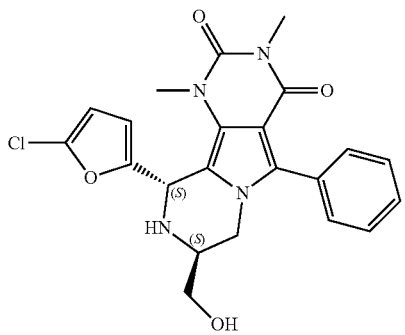

Step 1: Methyl 3-amino-2-(((benzyloxy)carbonyl)amino)propanoate

Acetyl chloride (0.627 ml, 8.81 mmol) was added dropwise to a suspension of commercially available Z-Dap-OH ((S)-3-amino-2-(((benzyloxy)carbonyl)amino)propanoic acid) (1 g, 4.20 mmol) in methanol (20 ml) at 0° C. The mixture was stirred at 0° C. for 4 hours and at room temperature for 16 hours. The solvent was evaporated under vacuum to afford the title compound.

1H NMR (400 MHz, DMSO-d6) δ 8.19 (3H, br s), 7.90 (1H, d), 7.43-7.28 (5H, m), 5.07 (2H, s), 4.43 (1H, m), 3.68 (3H, s), 3.22 (1H, dd), 3.06 (1H, dd)

LC-MS Rt 0.47 mins [M+H]+ 253.5 (Method 2minLow-pHv03)

Step 2: Methyl 2-(((benzyloxy)carbonyl)amino)-3-(1,3-dimethyl-2,4-dioxo-5-phenyl-3,4-dihydro-1H-pyrrolo[3,4-d]pyrimidin-6(2H)-yl)propanoate 5-Benzoyl-6-(bromomethyl)-1,3-dimethylpyrimidine-2,4(1H,3H)-dione (Intermediate A Step 3) (1.342 g, 3.98 mmol), (S)-methyl 3-amino-2-(((benzyloxy)carbonyl)amino)propanoate (1.207 g, 4.18 mmol) and triethylamine (1.665 ml, 11.94 mmol) were suspended in methanol (20 ml). The mixture was heated to reflux for 16 hours then cooled to room temperature and filtered. The residue was rinsed with methanol (20 ml) to afford the title compound.

1H NMR (400 MHz, DMSO-d6) δ 7.79 (1H, d), 7.49-7.36 (5H, m), 7.36-7.21 (5H, m), 6.88 (1H, s), 4.98 (1H, d), 4.88 (1H, d), 4.04-4.27 (3H, m), 4.17 (1H, dd), 3.55 (3H, s), 3.25 (3H, s), 3.15 (3H, s).

LC-MS Rt 1.20 mins [M+H]+ 491.3 (Method 2minLow-pHv03)

Step 3: Benzyl (1-(1,3-dimethyl-2,4-dioxo-5-phenyl-3,4-dihydro-1H-pyrrolo[3,4-d]pyrimidin-6(2H)-yl)-3-hydroxypropan-2-yl)carbamate and 1,3-dimethyl-6-((2-oxooxazolidin-4-yl)methyl)-5-phenyl-1H-pyrrolo[3,4-d]pyrimidine-2,4(3H,6H)-dione Sodium borohydride (0.234 g, 6.20 mmol) was added to a solution of methyl 2-(((benzyloxy)carbonyl)amino)-3-(1,3-dimethyl-2,4-dioxo-5-phenyl-3,4-dihydro-1H-pyrrolo[3,4-d]pyrimidin-6(2H)-yl)propanoate (1.52 g, 3.10 mmol) and lithium chloride (0.263 g, 6.20 mmol) in THF (79 ml) and EtOH (39.7 ml) at 0° C. The mixture was stirred at room temperature for 16 hours. The reaction was quenched with saturated NaHCO3(aq) (20 mL), diluted with water (50 ml) and extracted with DCM (3×150 ml). The combined organic extracts were diluted with MeOH (50 ml), dried over sodium sulfate, passed through a hydrophobic frit and evaporated under vacuum to afford the title compound and was a by-product. The resulting mixture was taken forward to the next step without further purification.

LC-MS Rt 1.05 mins [M+H]+ 463.6 (Method 2minLow-pHv03).

Step 4: 6-(2-Amino-3-hydroxypropyl)-1,3-dimethyl-5-phenyl-1H-pyrrolo[3,4-d]pyrimidine-2,4(3H,6H)-dione A mixture of benzyl (1-(1,3-dimethyl-2,4-dioxo-5-phenyl-3,4-dihydro-1H-pyrrolo[3,4-d]pyrimidin-6(2H)-yl)-3-hydroxypropan-2-yl)carbamate and 1,3-dimethyl-6-((2-oxooxazolidin-4-yl)methyl)-5-phenyl-1H-pyrrolo[3,4-d]pyrimidine-2,4(3H,6H)-dione (1.67 g) and 10% palladium on carbon (200 mg, 3.61 mmol) were suspended in ethanol (50 ml) and stirred under an atmosphere of hydrogen for 18 hours. The mixture was passed through pre-packed Celite® cartridge (10 g, filter material) and the residue washed with ethanol (20 ml). The combined filtrates were evaporated under vacuum. The residue was suspended in THF (18 ml) and water (5 ml). Lithium hydroxide (20 mg) was added and the mixture stirred at room temperature for 4 hours, then quenched with 2M HCl (aq). NaHCO3(aq) solution (20 ml) was added to achieve pH 6 and the mixture extracted with DCM (3×30 ml), passed through a hydrophobic frit and evaporated under vacuum to afford the title compound.

LC-MS Rt 0.54 mins [M+H]+ 328.9 (Method 2minLow-pHv03)

Step 5: (8R,10R)-10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione or (8S,10S)-10-(5-chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione 6-(2-Amino-3-hydroxypropyl)-1,3-dimethyl-5-phenyl-1H-pyrrolo[3,4-d]pyrimidine-2,4(3H,6H)-dione (200 mg, 0.609 mmol) and 5-chlorofuran-2-carbaldehyde (87 mg, 0.670 mmol) were suspended in ethanol (1.2 ml) and the mixture heated at 50° C. under microwave radiation for 15 mins, followed by a further 30 mins. The mixture was evaporated under vacuum. Purification was carried out by mass-directed HPLC using the following conditions to afford a mixture of diastereomers.

Column: XSelect CSH Prep C18 column, 30×100 mm, 5 um.

Mobile phase: A=0.1% DEA in water, B=0.1% DEA in MeCN

Elution gradient:
0.0-0.5 min: 30% B 30 mL/min
0.5-1.0 min: 30% B 30-50 mL/min
1.0-7.2 min: 30-70% B, 7.2-7.3 min: 70-98% B, 7.3-9.4 min: 98% B
9.4-9.5 30% B 50 mL/min The two diastereomers were separated by SFC chromatography using the following conditions to afford the title compound.

Column: Chiralpak IC, 250×10 mm, 5 um @ 35 deg C
Mobile phase: 50% Methanol/50% CO2
Flow: 10 ml/min
Detection: UV @ 220 nm

Example 11a

Diastereomer 1 of 10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione Rt=5.89 mins
1H NMR (400 MHz, DMSO-d6) δ 7.55-7.40 (5H, m), 6.39 (1H, d), 6.08 (1H, d), 5.87 (1H, s), 4.78 (1H, t), 3.84 (1H, dd), 3.50 (1H, t), 3.42 (1H, m), 3.35 (1H, q), 3.30 (3H, s), 3.15 (3H, s), 3.02-2.91 (2H, m).
LC-MS Rt 1.04 mins [M+H]+ 441.3 (Method 2minLowpHv03)
The second diastereomer was isolated at Rt=8.13 mins

Example 12

(8S,10S)-1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione or (8S,10R)-1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione

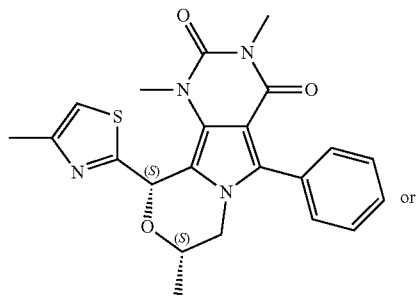

(8S,10S)-1,3,8-trimethyl-10-(4-methyl thiazol-2-yl)-5-phenyl-7,8-dihydro-1H-pyrimido [4',5':3,4]pyrrolo[2,1-c][1,4]oxazine-2-,4(3H,10H)-dione

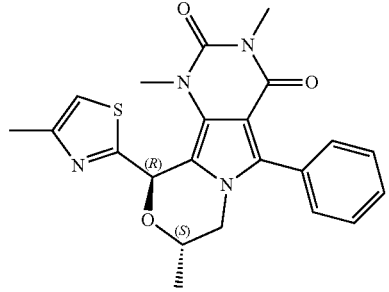

(8S,10R)-1,3,8-trimethyl-10-(4-methyl thiazol-2-yl)-5-phenyl-7,8-dihydro-1H-pyrimido [4',5':3,4]pyrrolo[2,1-c][1,4]oxazine-2-,4(3H,10H)-dione Step 1: (S)-6-(2-Hydroxypropyl)-1,3-dimethyl-5-phenyl-1H-pyrrolo[3,4-d]pyrimidine-2,4(3H,6H)-dione A mixture of 5-benzoyl-6-(bromomethyl)-1,3-dimethylpyrimidine-2,4(1H,3H)-dione (Intermediate A, Step 3) (200 mg 0.59 mmol), triethylamine (82 μl, 0.59 mmol) and (S)-1-aminopropan-2-ol (44.6 mg 0.59 mmol) in ethanol (2 ml) was heated under microwave radiation for 1 hour. The reaction mixture was filtered and the residue rinsed with ethanol to afford the title compound.
1H NMR (400 MHz, CDCl3) δ 7.51-7.43 (5H, m); 6.55 (1H, s); 4.07-3.83 (1H, m); 3.96-3.82 (3H, m); 3.42 (3H, s); 3.34 (3H, s); 1.11 (3H, d)
LC-MS Rt 0.82 mins [M+H]+ 314 Method 2minLC_v003

Step 2: 1,3,85-trimethyl-10(R or S)-(4-methylthiazol-2-yl)-5-phenyl-7,8-dihydro-1H-pyrimido[4',5':3,4]pyrrolo[2,1-c][1,4]oxazine-2,4(3H,10H)-dione A mixture of (S)-6-(2-hydroxypropyl)-1,3-dimethyl-5-phenyl-1H-pyrrolo[3,4-d]pyrimidine-2,4(3H,6H)-dione (160 mg 0.51 mmol), 4-methylthiazole-2-carbaldehyde (64.9 mg, 0.51 mmol) and bismuth triflate (31.9 mg, 0.051 mmol) in ethanol (2 ml) was heated under microwave radiation at 100° C. for 20 mins, then again at 100° C. for 40 mins. Further portions of 4-methylthiazole-2-carbaldehyde (64.9 mg, 0.51 mmol) and bismuth triflate (31.9 mg, 0.051 mmol) were added and the mixture was heated under microwave radiation at 100° C. for 40 mins. The mixture was evaporated under vacuum. Purification by chromatography on silica, eluting 0-50% EtOAc/hexane afforded the title compounds as a mixture of diastereomers.
LC-MS Rt 4.56 mins [M+H]+ 423 (Method 10minLC_v003)

Step 3: (8S,10S)-1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione or (8S,10R)-1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione The mixture of diastereomers was separated by SFC under the following conditions to afford the title compound as a single diastereomer.
Column: Chiralpak AD-H, 250×10 mm, 5 um @ 35 deg C
Mobile phase: 40% Methanol/60% CO2
Flow: 10 ml/min
Detection: UV @ 220 nm

Example 12

Diastereomer 1 of (8S)-1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione Rt 2.14 mins
1H NMR (400 MHz, CDCl3) δ 7.53-7.46 (5H, m), 6.97 (1H, s), 6.66 (1H, s), 4.18-4.09 (1H, m), 3.91 (1H, dd), 3.64 (1H, dd), 3.38 (3H, s), 3.37 (3H, s), 2.49 (3H, s), 1.28 (3H, d)
LC-MS Rt 1.04 mins [M+H]+ 423 (Method 2minLC_v003)
Diastereomeric purity >99% d.e.
The second diastereomer was isolated at Rt 2.14 mins The following examples was prepared by a similar method to that of Example 12 from the appropriate starting compounds (if necessary replacing benzoyl chloride with the appropriate substituted benzoyl chloride in the preparation of the starting bromide, using the appropriate commerically available aminoalcohol in step 1 and the appropriate commerically available aldehyde in step 3). Final purification of diastereomeric mixtures was carried out by SFC under the listed conditions to afford the title compounds.

Example 12.1

(8S,10R)-10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione or (8S,10S)-10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione

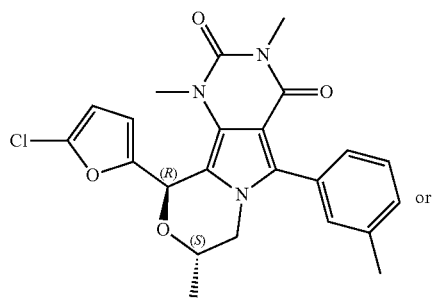

(8S,10R)-10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione or

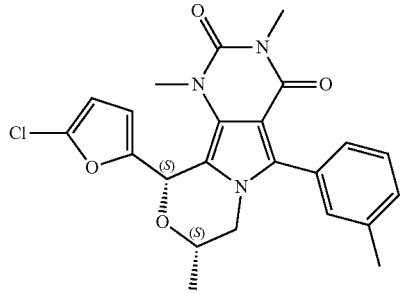

(8S,10S)-10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione The title compound was prepared from (S)-6-(2-hydroxypropyl)-1,3-dimethyl-5-m-tolyl-1H-pyrrolo[3,4-d]pyrimidine-2,4(3H,6H)-dione and 5-chlorofuran-2-carbaldehyde by an analogous method to Example 12. Purification was carried out by chromatography on silica eluting with 0-55% EtOAc in iso-hexane;

1H NMR (400 MHz, CDCl3) δ 7.40 (1H, t); 7.30-7.23 (4H, m); 6.40 (1H, s); 6.15 (1H, d); 6.08 (1H, d); 4.05-3.98 (1H, m); 3.85 (1H, dd); 3.57 (1H, dd); 3.35 (6H, s); 2.45 (3H, s); 1.27 (3H, d).

LC-MS Rt 1.34 mins [M+H]+ 440 (Method 2minLow-pHv01)

Example 12.2

(8S,10R)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione or (8R,10R)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione or (8S,10S)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione or (8R,10S)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione

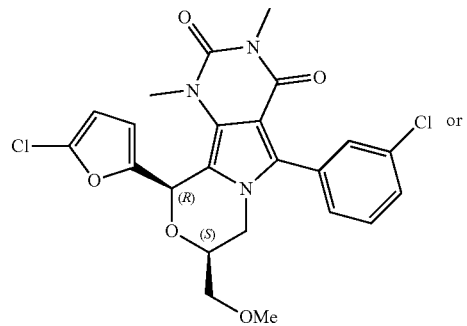

(8S,10R)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione

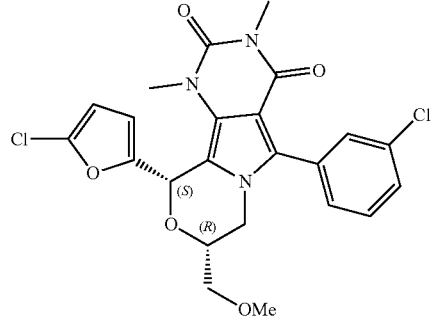

(8R,10S)-10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione

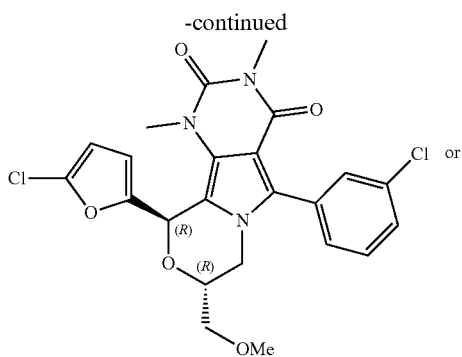

(8R,10R)-10-(5-chlorofuran-2-yl)-5-(3-chlorophenyl)-8-
(methoxymethyl)-1,3-dimethyl-7,8-
dihydro-1H-pyrimido[4',5':3,4]pyrrolo[2,1-c][1,4]
oxazine-2,4(3H,10H)-dione

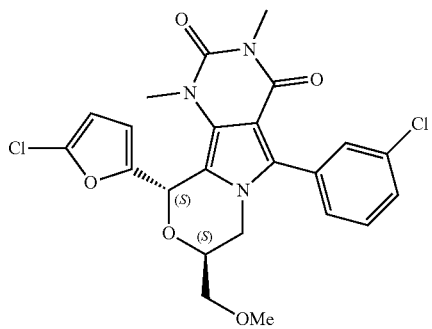

(8S,10S)-10-(5-chlorofuran-2-yl)-5-(3-chlorophenyl)-8-
(methoxymethyl)-1,3-dimethyl-7,8-
dihydro-1H-pyrimido[4',5':3,4]pyrrolo[2,1-c][1,4]
oxazine-2,4(3H,10H)-dione The diastereomeric mixture of 10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione was separated by SFC under the following conditions to afford the title compounds as single enantiomer.

Column: Chiralpak AD-H 250×10 mm, 5 um @ 35 deg C

Mobile phase: 35% Isopropanol/65% CO2

Flow: 10 ml/min

Detection: UV @ 220 nm

Example 12.2 Diastereomer 1 of 10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione Rt 3.57 mins LCMS Rt 1.43 mins [M+H]+ 490.1 (Method 2minLow-pHv03)

1H NMR (400 MHz, CDCl3): δ 7.47-7.43 (3H, m), 7.38-7.34 (1H, m), 6.45 (1H, s), 6.17 (1H, s), 6.11 (1H, s), 4.11-4.03 (1H, m), 3.92-3.86 (2H, m), 3.58-3.50 (2H, m), 3.39-3.33 (9H, m).

Chiral purity >99% d.e.

Example 12.3

(8S,10S)-10-(5-chlorofuran-2-yl)-1,3-dimethyl-5,8-diphenyl-7,8-dihydro-1H-pyrimido[4',5':3,4]pyrrolo[2,1-c][1,4]oxazine-2,4(3H,10H)-dione or (8S,10R)-10-(5-chlorofuran-2-yl)-1,3-dimethyl-5,8-diphenyl-7,8-dihydro-1H-pyrimido[4',5':3,4]pyrrolo[2,1-c][1,4]oxazine-2,4(3H,10H)-dione

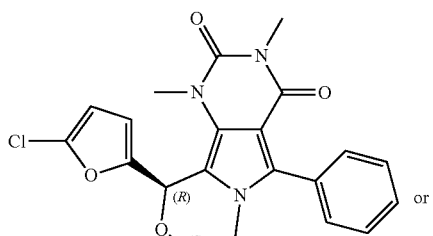

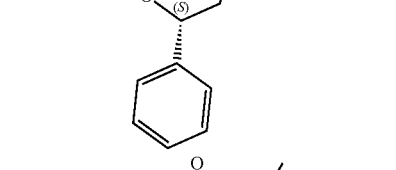

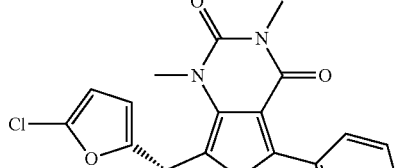

The title compound was prepared from (S)-6-(2-hydroxy-2-phenylethyl)-1,3-dimethyl-5-phenyl-1H-pyrrolo[3,4-d]pyrimidine-2,4(3H,6H)-dione and commercially available 5-chlorofuran-2-carbaldehyde. The resulting mixture of diastereomers was separated by SFC under the following conditions to afford the title compound as a single diastereomer;

Column: Chiralpak AS 250×10 mm

Mobile phase: 40% Methanol+0.1% v/v DEA/30% CO2

Flow: 10 ml/min

Example 12.3

Diastereomer 1 of 10-(5-chlorofuran-2-yl)-1,3-dimethyl-5,8-diphenyl-7,8-dihydro-1H-pyrimido[4',5':3,4]pyrrolo[2,1-c][1,4]oxazine-2,4(3H,10H)-dione Rt=2.92 mins 1H NMR (400 MHz, CDCl3) δ 7.48-7.44 (5H, m); 7.38-7.34 (5H, m); 6.62 (1H, s); 6.20 (1H, d); 6.18 (1H, d); 4.94 (1H, dd); 4.08 (1H, dd); 3.89 (1H, dd); 3.39 (3H, s); 3.38 (3H, s)

LC-MS Rt 1.43 mins [M+H]+ 488 Method 2minLow-pHv01

Diastereomeric purity >99% d.e.

Example 12.4

(8R,10R)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione or (8S,10S)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione or (8R,10S)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione or (8S,10R)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione

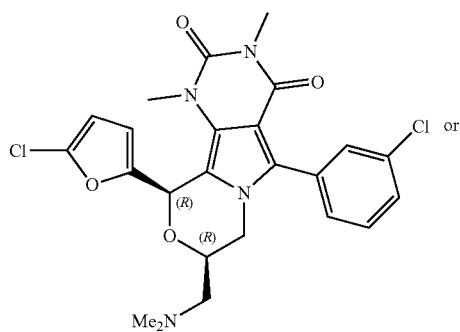

(8R,10R)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione

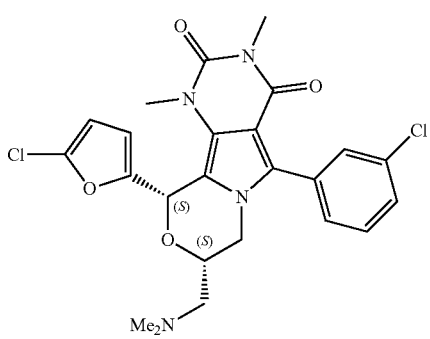

(8S,10S)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione

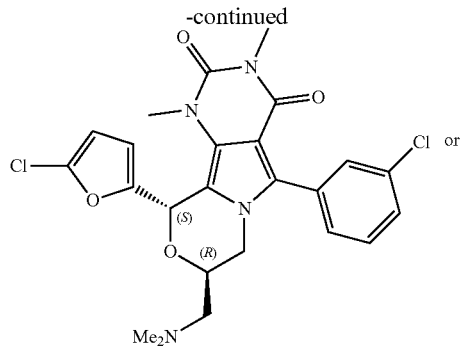

(8R,10S)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione

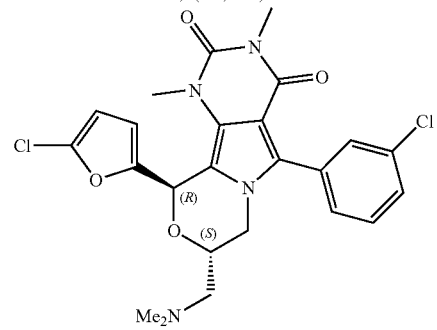

(8S,10R)-10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione The title compound was prepared from 5-(3-chlorophenyl)-6-(3-(dimethylamino)-2-hydroxypropyl)-1,3-dimethyl-1H-pyrrolo[3,4-d]pyrimidine-2,4(3H,6H)-dione and 5-chlorofuran-2-carbaldehyde analogously to Example 12, step 2. The first eluted diastereomer (by Agilent Prep. System (10-35%, low pH) was isolated and separated by SFC under the following conditions to yield the title compounds as single enantiomers.

Column: 2× Chiralpak AD-H, 250×10 mm, 5 um @ 35 deg C

Mobile phase: 35% Isopropanol+0.1% v/v DEA/65% CO2
Flow: 10 ml/min
Detection: UV @ 220 nm

Example 12.4

Diastereomer 1 of 10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione SFC Rt 3.03 mins
1H NMR (400 MHz, CDCl3): δ 7.48-7.42 (3H, m), 7.38-7.34 (1H, m), 6.46 (1H, s), 6.20-6.13 (2H, m), 3.93-3.87 (1H, m), 3.72-3.65 (1H, m), 3.38 (6H, s), 2.76-2.58 (1H, br s), 2.40-2.18 (6H, br s)
LC-MS Rt 3.29 mins [M+H]$^+$ 503.3 (Method 5minhighpHV01)
Chiral purity >99% d.e.
A second enantiomer was isolated at SFC Rt 2.47 mins

Example 12.5

10-(5-Chlorofuran-2-yl)-1,3,8,8-tetramethyl-5-phenyl-7,8-dihydro-1H-pyrimido[4',5':3,4]pyrrolo[2,1-c][1,4]oxazine-2,4(3H,10H)-dione

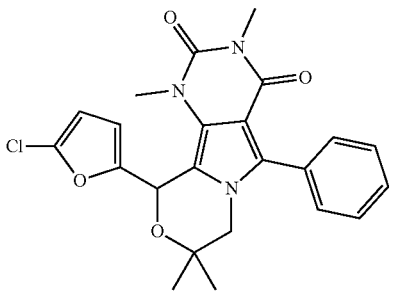 [SMILES: Cn1c(=O)c2c(-c3ccccc3)n3c(c2n(C)c1=O)C(c1ccc(Cl)o1)OC(C)(C)C3]

The title compound was prepared from 6-(2-hydroxy-2-methylpropyl)-1,3-dimethyl-5-phenyl-1H-pyrrolo[3,4-d]pyrimidine-2,4(3H,6H)-dione and commercially available 5-chlorofuran-2-carbaldehyde in toluene analogously to Example 12, step 2;

1H NMR (DMSO-d6, 400 MHz): δ 7.54-7.44 (5H, m), 6.48 (1H, d), 6.44-6.41 (2H, m), 4.0-3.95 (1H, m), 3.72-3.67 (1H, m), 3.23 (3H, s), 3.16 (3H, s), 1.23 (3H, s), 1.07 (3H, s).

LCMS Rt 1.29 mins [M+H]+ 440.2 (Method 2minlowpHv01)

Example 13

(S)-1'-(4-Chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione or (R)-1'-(4-Chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione

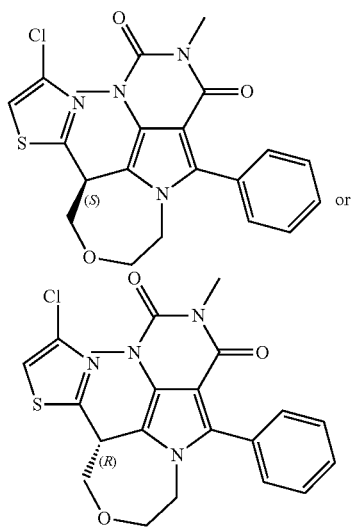

Step 1: 2-Bromo-N-methoxy-N-methylacetamide

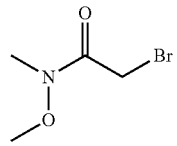

N,O-dimethylhydroxylamine hydrochloride (3 g, 30.8 mmol) and potassium carbonate (9.35 g, 67.7 mmol) were dissolved in Et$_2$O (50 mL) and water (50 mL) and the mixture cooled to 0° C. 2-Bromoacetyl bromide (2.95 mL, 33.8 mmol) was added dropwise and the mixture was stirred briefly at 0° C. and then warmed to room temperature and stirred for 40 mins. The reaction mixture was phase separated and the aqueous phase extracted with Et$_2$O. The combined organic phases were dried over sodium sulphate and evaporated under vacuum to afford the title compound as a colourless oil;

Step 2: 2-(2-(1,3-Dimethyl-2,4-dioxo-5-phenyl-3,4-dihydro-1H-pyrrolo[3,4-d]pyrimidin-6(2H)-yl)ethoxy)-N-methoxy-N-methylacetamide 6-(2-Hydroxyethyl)-1,3-dimethyl-5-phenyl-1H-pyrrolo[3,4-d]pyrimidine-2,4(3H,6H)-dione (700 mg, 2.339 mmol) was dissolved in THF (20 mL) and cooled to 0° C. Sodium hydride (281 mg, 7.02 mmol) was added and the mixture stirred at 0° C. for 15 mins. 2-Bromo-N-methoxy-N-methylacetamide (553 mg, 3.04 mmol) was added, the mixture warmed to room temp. and stirred for 20 mins. Further sodium hydride (281 mg, 7.02 mmol) and 2-bromo-N-methoxy-N-methylacetamide (553 mg, 3.04 mmol) were added and stirring continued for 45 mins. The reaction was quenched with water and extracted with chloroform (3×). The combined organic phases were passed through a hydrophobic frit and evaporated under vacuum. The residue was triturated with EtOAc/hexane and the solid collected by filtration to afford the title compound;

LC-MS: Rt 0.99 mins; MS 401.2 m/z [M+H] Method 2minLowpHv03

1H NMR (400 MHz, CDCl3) δ 7.47 (5H, mult), 6.72 (1H, br s), 4.26 (2H, s), 4.16 (2H, t), 3.81 (2H, t), 3.66 (3H, s), 3.45 (3H, s), 3.36 (3H, s), 3.20 (3H, s).

Step 3: 6-(2-(2-(4-Chlorothiazol-2-yl)-2-oxoethoxy)ethyl)-1,3-dimethyl-5-phenyl-1H-pyrrolo[3,4-d]pyrimidine-2,4(3H,6H)-dione 2-(2-(1,3-Dimethyl-2,4-dioxo-5-phenyl-3,4-dihydro-1H-pyrrolo[3,4-d]pyrimidin-6(2H)-yl)ethoxy)-N-methoxy-N-methylacetamide (800 mg, 1.998 mmol) and 2-bromo-4-chlorothiazole (Intermediate H, step 2) (397 mg, 1.998 mmol) were dissolved in THF and isopropylmagnesium chloride lithium chloride complex (4610 µl, 5.99 mmol) was added slowly. The mixture was stirred at room temp. for 20 minutes and the reaction was quenched with sat. NH4Cl (aq) and extracted with DCM (3×). The combined organic phases were passed through a hydrophobic frit and evaporated onto silica. The silica was deposited onto a 25 g silica cartridge and the system eluted with 50% EtOAc/hexane, 60% EtOAc/hexane, 75% EtOAc/hexane and 80% EtOAc/hexane. The product fractions were combined and evaporated. The resulting residue was triturated with Et$_2$O/hexane and filtered to afford the title compound;

LC-MS: Rt 1.24 mins; MS 459.1 m/z [M+H] Method 2minLowpHv03

1H NMR (400 MHz, CDCl3) δ 7.53 (1H, s), 7.48 (5H, mult), 6.69 (1H, br s), 4.91 (2H, s), 4.19 (2H, t), 3.85 (2H, t), 3.46 (3H, s), 3.36 (3H, s).

Step 4: 6-(2-(2-(4-Chlorothiazol-2-yl)-2-hydroxyethoxy)ethyl)-1,3-dimethyl-5-phenyl-1H-pyrrolo[3,4-d]pyrimidine-2,4(3H,6H)-dione 6-(2-(2-(4-Chlorothiazol-2-yl)-2-oxoethoxy)ethyl)-1,3-dimethyl-5-phenyl-1H-pyrrolo[3,4-d]pyrimidine-2,4(3H,6H)-dione (540 mg, 1.177 mmol) was dissolved in MeOH (20 mL) and sodium borohydride (134 mg, 3.53 mmol) was added. The mixture was stirred at room temp. for 25 minutes and the reaction was quenched with sat. NaHCO3(aq) and extracted with chloroform (3×). The combined organic extracts were passed through a hydrophobic frit and evaporated under vacuum to afford the title compound;
LC-MS: Rt 1.10 mins; MS 461.1 m/z [M+H] Method 2minLowpHv03
1H NMR (400 MHz, CDCl3) δ 7.52-7.40 (5H, mult), 7.08 (1H, s), 6.46 (1H, br s), 5.03 (1H, dd), 4.11 (2H, t), 3.86 (1H, dd), 3.80-3.65 (3H, mult), 3.43 (3H, s), 3.37 (3H, s).

Step 5: 11-(4-Chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione 6-(2-(2-(4-Chlorothiazol-2-yl)-2-hydroxyethoxy)ethyl)-1,3-dimethyl-5-phenyl-1H-pyrrolo[3,4-d]pyrimidine-2,4(3H,6H)-dione (300 mg, 0.651 mmol), and triethylamine (0.272 mL, 1.953 mmol) were dissolved in DCM (10 mL) and Tf$_2$O (0.165 mL, 0.976 mmol) was added in a single portion. The mixture was stirred at room temp. for 15 mins and further triethylamine (0.272 mL, 1.953 mmol) and Tf$_2$O (0.165 mL, 0.976 mmol) were added. After 45 mins, further triethylamine (0.272 mL, 1.953 mmol) and Tf$_2$O (0.165 mL, 0.976 mmol) were added. After stirring for a further 45 mins, the reaction was quenched with sat. NaHCO3(aq) and extracted with DCM (3×). The combined organic phases were passed through a hydrophobic frit and evaporated under vacuum. The residue was redissolved in DCM and evaporated onto silica. The silica was deposited onto a 10 g silica cartridge and the system gradient-eluted from 10-80% EtOAc/hexane. The product fractions were combined and evaporated. The resulting residue was triturated with DCM/Et$_2$O/hexane and the precipitate collected by filtration to afford the title compound as a pale yellow solid;
LC-MS: Rt 1.23 mins; MS 443.5 m/z [M+H] Method 2minLowpHv03.

Step 6: (S)-11-(4-chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione Racemic 11-(4-chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione was separated by SFC under the following conditions to afford the title compound as a single enantiomer SFC Chiralpak IB 250×10 mm, 5 um @ 35 deg C, 40% Methanol+0.1% v/v DEA/60% CO2, 10 ml/min, Detection: UV @ 220 nm Enantiomer 1 of 11-(4-chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione SFC Retention Time=5.61 mins, >99% e.e.
LC-MS: Rt 1.26 mins; MS 443.2 m/z [M+H] Method 2minLowpHv03

1H NMR (400 MHz, CDCl3) δ 7.55-7.31 (5H, mult), 7.12 (1H, s), 5.16 (1H, d), 4.98 (1H, dd), 4.23-4.07 (2H, mult), 4.07-3.92 (2H, mult), 3.65 (3H, s), 3.62 (1H, mult), 3.36 (3H, s)

The second enantiomer was isolated at SFC Retention Time=7.61 mins.

Example 14

3-((8S,11S)-1'-(4-Chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile or 3-((8R,11S)-1'-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile or 3-((8S,11R)-1'-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile or 3-((8R,11R)-1'-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile

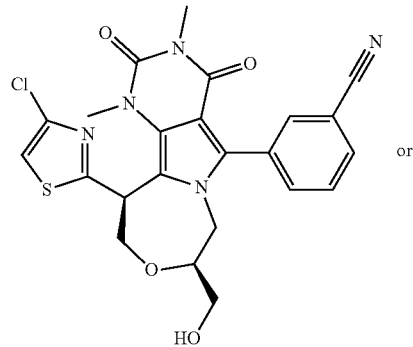

3-((8S,11S)-11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile or

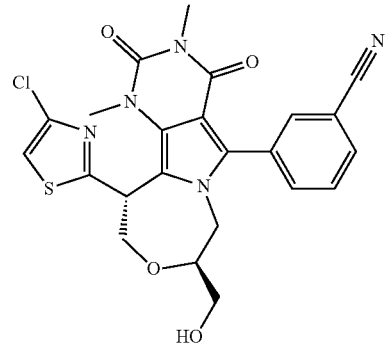

3-((8S,11R)-11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile

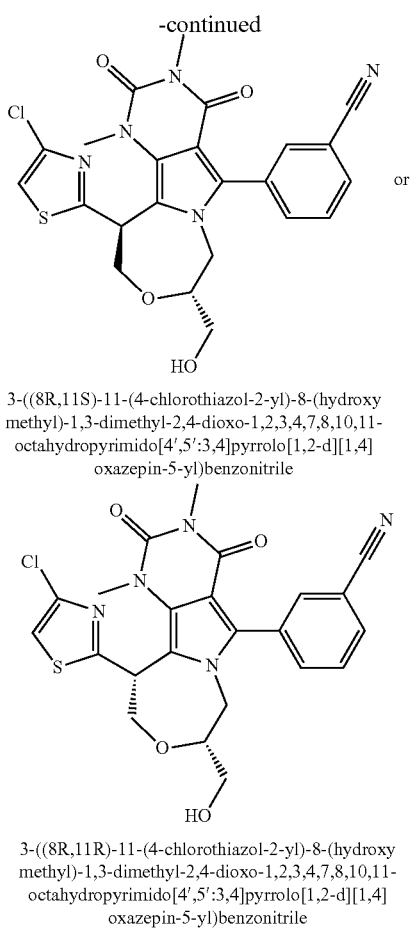

3-((8R,11S)-11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile 3-((8R,11R)-11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile Step 1: 2-((1-(((tert-Butyldimethylsilyl)oxy)-3-(5-(3-cyanophenyl)-1,3-dimethyl-2,4-dioxo-3,4-dihydro-1H-pyrrolo[3,4-d]pyrimidin-6(2H)-yl)propan-2-yl)oxy)-N-methoxy-N-methylacetamide To a stirred solution of 3-(6-(3-((tert-Butyldimethylsilyl)oxy)-2-hydroxypropyl)-1,3-dimethyl-2,4-dioxo-2,3,4,6-tetrahydro-1H-pyrrolo[3,4-d]pyrimidin-5-yl)benzonitrile (Example 9a, step 1) (280 mg, 0.597 mmol) in THF (5975 µL) was added sodium hydride (60% in mineral oil) (71.7 mg, 1.792 mmol) at 0° C. The resulting red solution was warmed to room temperature and stirred for 20 minutes, before being cooled to 0° C. 2-Bromo-N-methoxy-N-methylacetamide (Example 13, step 1) (141 mg, 0.777 mmol) was then added dropwise over 5 minutes. The reaction mixture was warmed to room temperature over 3 hours and then cooled to 0° C. and quenched with saturated aqueous ammonium chloride solution (5 mL). DCM (10 mL) was added to the biphasic solution. The aqueous phase was separated and extracted with DCM (3×10 mL); the combined organic extracts were dried (MgSO4) and concentrated under reduced pressure to afford a yellow oil. The oil was purified using Teledyne ISCO (12 g, SiO2) eluting with 0-65% EtOAc/hexanes to afford the title compound as an amorphous white solid.

LCMS; Rt 1.48 mins; MS m/z 570.7 [M+H]+; 2minlowpHVO3.

Step 2: 3-(6-(3-((tert-Butyldimethylsilyl)oxy)-2-(2-(4-chlorothiazol-2-yl)-2-oxoethoxy)propyl)-1,3-dimethyl-2,4-dioxo-2,3,4,6-tetrahydro-1H-pyrrolo[3,4-d]pyrimidin-5-yl)benzonitrile The title compound was prepared from 2-((1-(((tert-butyldimethylsilyl)oxy)-3-(5-(3-cyanophenyl)-1,3-dimethyl-2,4-dioxo-3,4-dihydro-1H-pyrrolo[3,4-d]pyrimidin-6(2H)-yl)propan-2-yl)oxy)-N-methoxy-N-methylacetamide and 2-bromo-4-chlorothiazole analogously to Example 13, step 3;

LCMS; Rt 1.65 mins; MS m/z 628.2 [M+H]+; 2minlowpHVO3.

Step 3: Mixture diastereomers of 3-(6-(3-((tert-butyldimethylsilyl)oxy)-2-(2-(4-chlorothiazol-2-yl)-2-hydroxyethoxy)propyl)-1,3-dimethyl-2,4-dioxo-2,3,4,6-tetrahydro-1H-pyrrolo[3,4-d]pyrimidin-5-yl)benzonitrile The title compound was prepared from 3-(6-(3-((tert-butyldimethylsilyl)oxy)-2-(2-(4-chlorothiazol-2-yl)-2-oxoethoxy)propyl)-1,3-dimethyl-2,4-dioxo-2,3,4,6-tetrahydro-1H-pyrrolo[3,4-d]pyrimidin-5-yl)benzonitrile analogously to Example 13, step 4; LCMS; Rt 1.55, 1.57 mins; MS m/z 630.6, 630.6 [M+H]+; 2minlowpHVO3. Approximately 1:1 mixture of diastereomers.

Step 4: Diastereomer Pair 1 and Pair 2 of 3-(11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile The title compound was prepared from 3-(6-(3-((tert-butyldimethylsilyl)oxy)-2-(2-(4-chlorothiazol-2-yl)-2-hydroxyethoxy)propyl)-1,3-dimethyl-2,4-dioxo-2,3,4,6-tetrahydro-1H-pyrrolo[3,4-d]pyrimidin-5-yl)benzonitrile analogously to Example 13, step 5;

The residue was purified using the Agilent Prep. System (20-50%, low pH) to afford the title pairs of diastereomers amorphous white solids.

First Eluted Peak:

Diastereomer Pair 1 of 3-(11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile LCMS; Rt 1.06 mins; MS m/z 498.2 [M+H]+; 2minlowpHVO3.

Second Eluted Peak:

Diastereomer Pair 2 of 3-(11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile LCMS; Rt 1.08 mins; MS m/z 498.5 [M+H]+; 2minlowpHVO3.

Step 5: Diasteromer 1 of 11-(4-Chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile was separated from Diastereomer Pair 2 by SFC under the following conditions: SFC Chiralpak ID 250×10 mm, 5 um @ 35 deg C, 40% Isopropanol/60% CO2, 10 ml/min, Detection: UV @ 220 nm Second Eluted Peak: SFC Retention Time=7.01 mins
LCMS; Rt 1.12 mins; MS m/z 498.3 [M+H]+; 2minlowpHVO3.
1H NMR (400 MHz, CDCl3): δ 7.71-7.50 (4H, m), 7.05 (1H, s), 5.09 (1H, d), 4.98-4.92 (1H, m), 4.08-4.03 (2H, m), 3.82-3.73 (1H, m), 3.70-3.63 (1H, m), 3.59 (3H, s), 3.57-3.42 (1H, m), 3.27 (3H, s).

Example 15

(8R,10R)-8-((1H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione

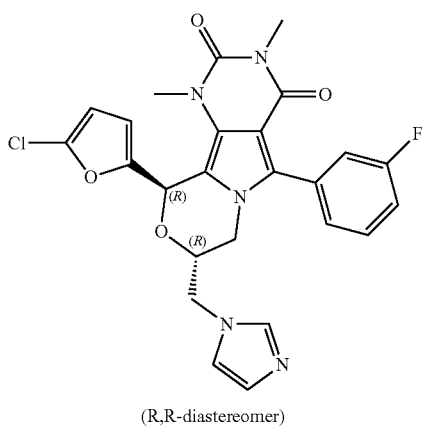

(R,R-diastereomer)

Step 1: ((8R)-10-(5-Chlorofuran-2-yl)-5-(3-fluorophenyl)-1,3-dimethyl-2,4-dioxo-2,3,4,7,8,10-hexahydro-1H-pyrimido[4',5':3,4]pyrrolo[2,1-c][1,4]oxazin-8-yl)methyl methanesulfonate Methanesulfonyl chloride (0.021 ml, 0.274 mmol) was added dropwise to a solution of (8R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione (Example 6, Step 3) (100 mg, 0.217 mmol), triethylamine (0.039 ml, 0.283 mmol) and DMAP (2.66 mg, 0.022 mmol) in DCM (2 mL). The mixture was stirred at 0° C. for 30 mins then diluted with DCM (20 ml) and quenched with water (20 mL). The phases were separated and the organic layer was dried over magnesium sulfate and evaporated under vacuum to afford the title compound.
LC-MS Rt 1.31 min [M+H]⁺ 538.5 (Method 2minLowpHv03)

Step 2: H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione A mixture of ((8R)-10-(5-chlorofuran-2-yl)-5-(3-fluorophenyl)-1,3-dimethyl-2,4-dioxo-2,3,4,7,8,10-hexahydro-1H-pyrimido[4',5':3,4]pyrrolo[2,1-c][1,4]oxazin-8-yl)methyl methanesulfonate (117 mg, 0.217 mmol), cesium carbonate (142 mg, 0.435 mmol) and imidazole (22.51 mg, 0.331 mmol) in acetonitrile (6 mL) was heated at 80° C. for 16 hours, then at 85° C. for 3.5 hours. Further portions of imidazole (22.51 mg, 0.331 mmol) and cesium carbonate (142 mg, 0.435 mmol) were added and the mixture heated for a further 2 hours. The mixture was cooled to room temperature, diluted with water (30 ml) and extracted with DCM (2×30 ml). The combined organic extracts were washed with brine (30 ml) passed through a hydrophobic frit and evaporated under vacuum. Purification by chromatography on silica, eluting with 0-100% EtOAc/hexane then with 0-10% MeOH/DCM, afforded the title compound as a mixture of diastereomers.

LC-MS Rt 0.85 min [M+H]⁺ 510.5 and Rt 0.89 min [M+H]⁺ 510.4 (Method 2minLowpHv03)

Step 3: (8R,10R)-8-((1H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione Separation of the diastereomeric mixture of (8R)-8-((1H-imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione by SFC under the following conditions afforded the title compound.

Column: Chiralpak AD-H 250×10 mm, 5 um @ 35° C.
Mobile phase: 30% Methanol+0.1% v/v DEA/70% CO2
Flow: 10 ml/min
Detection: UV @ 220 nm Diastereomer (8R,10R)-8-((1H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione Rt=5.98 mins
LC-MS Rt 0.84 min [M+H]⁺ 510.5 Method 2minLowpHv03
1H NMR (400 MHz, CDCl₃) δ 7.45 (m, 2H), 7.19 (dd, 2H), 7.13 (m, 1H), 7.05 (s, 1H), 6.94 (s, 1H), 6.47 (s, 1H), 6.11 (d, 1H), 6.06 (d, 1H), 4.12 (m, 3H), 3.88 (dd, 1H), 3.59 (dd, 1H), 3.35 (s, 3H), 3.34 (s, 3H)
Chiral purity >99% d.e.
The second diastereomer eluted at Rt=3.74 mins

Example 16

(8R,10R)-(5-Chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione or (8R,10S)-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione or (8S,10R)-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione or (8S,10S)-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione

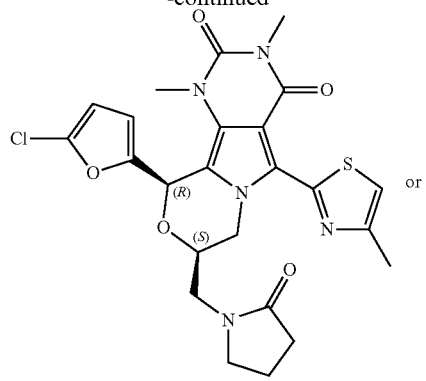

(R,S)-diastereomer

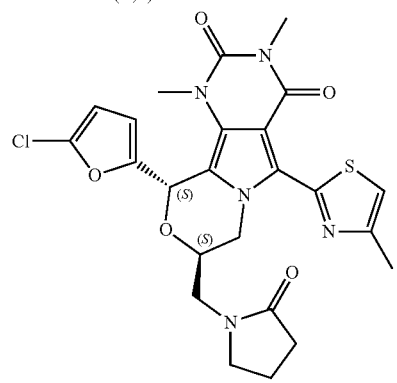

(S,S)-diastereomer

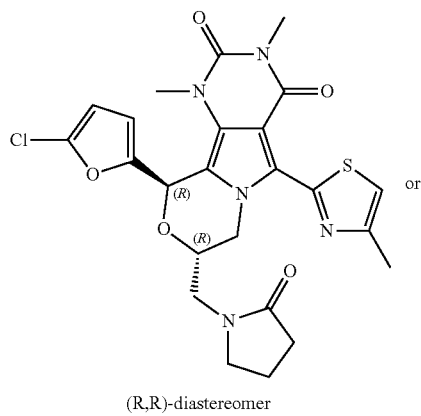

(R,R)-diastereomer

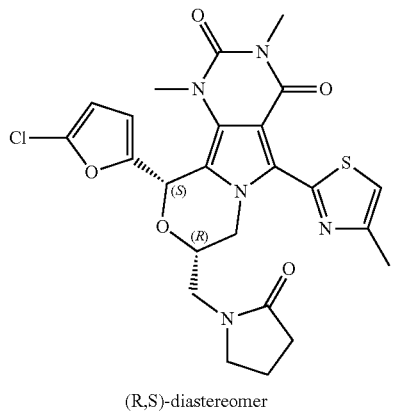

(R,S)-diastereomer

Step 1: 2-(3-Bromo-2-hydroxypropyl)isoindoline-1,3-dione

48% HBr (12.25 ml, 108 mmol) was added dropwise to a solution of 2,3-epoxypropylphthalimide (2 g, 9.84 mmol) in chloroform (25 ml) at 0° C. The mixture was stirred for 16 hours, then washed with brine (50 ml). The aqueous phase was extracted with DCM (2×40 ml) and the combined organic passed through a hydrophobic frit and evaporated under vacuum. Purification by chromatography on silica, eluting with 0-60% EtOAc/hexane, afforded the title compound.

LC-MS: Rt 0.95 min [M+H]$^+$ 284.1 (Method 2minLowpHv03)

Step 2: 2-(3-Bromo-2-((tert-butyldimethylsilyl)oxy)propyl)isoindoline-1,3-dione A solution of 2-(3-bromo-2-hydroxypropyl)isoindoline-1,3-dione (100 mg, 0.352 mmol) in DMF (0.5 mL) was added dropwise to a mixture of DMAP (43.0 mg, 0.352 mmol), imidazole (47.9 mg, 0.704 mmol) and tertbutyldimethylsilyl chloride (74.3 mg, 0.493 mmol) in DMF (1 mL). The mixture was stirred at room temperature for 18 hours. The mixture was diluted with EtOAc (20 ml) and washed with saturated NaHCO$_3$(aq) (20 ml) and brine (3×10 ml). The organic phase was dried over magnesium sulfate and evaporated under vacuum. Purification by chromatography on silica, eluting with 0-100% EtOAc/hexane, afforded the title compound.

LC-MS Rt 1.72 min [M+H]$^+$ 398.3 (Method 2minLowpHv03)

Step 3: 6-(2-((tert-Butyldimethylsilyl)oxy)-3-(1,3-dioxoisoindolin-2-yl)propyl)-1,3-dimethyl-5-(4-methylthiazol-2-yl)-1H-pyrrolo[3,4-d]pyrimidine-2,4(3H,6H)-dione Cesium carbonate (115 mg, 0.351 mmol) was added to a solution of 1,3-dimethyl-5-(4-methylthiazol-2-yl)-1H-pyrrolo[3,4-d]pyrimidine-2,4(3H,6H)-dione (Intermediate Gc) (53.4 mg, 0.176 mmol) and 2-(3-bromo-2-((tert-butyldimethylsilyl)oxy)propyl)isoindoline-1,3-dione (70 mg, 0.176 mmol) in N,N-dimethylacetamide (1273 µl). The mixture was heated at 50° C. for 18 hours, then cooled to room temperature and diluted with water (30 ml). The mixture was extracted with ethyl acetate (3×30 ml), the combined organic extracts were washed with brine (90 ml), dried over sodium sulfate and evaporated under vacuum. Purification by chromatography on silica, eluting with 0-100% EtOAc/hexane, afforded the title compound.
LC-MS Rt 1.68 min [M+H]+ 594.6 (Method 2minLowpHv03)

Step 4: 10-(5-Chlorofuran-2-yl)-8-((1,3-dioxoisoindolin-2-yl)methyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Trifluoroacetic acid (0.032 ml, 0.421 mmol) was added to a solution of 6-(2-((tert-butyldimethyl silyl)oxy)-3-(1,3-dioxoisoindolin-2-yl)propyl)-1,3-dimethyl-5-(4-methylthiazol-2-yl)-1H-pyrrolo[3,4-d]pyrimidine-2,4(3H,6H)-dione (50 mg, 0.084 mmol) in toluene (1 ml) and the mixture was stirred for 30 mins. Bismuth triflate (27.6 mg, 0.042 mmol) and 5-chlorofuran-2-carbaldehyde (16.49 mg, 0.126 mmol) were added and the mixture stirred at room temperature for 16 hours. The mixture was diluted with ethyl acetate (30 ml) and washed with water (30 ml), saturated NaHCO$_3$(aq) (50 ml) and brine (50 ml). The organic layer was dried over magnesium sulfate and evaporated under vacuum. Purification by chromatography on silica, eluting with 0-100% EtOAc/hexane, afforded the title compound.
LC-MS Rt 1.42 min [M+H]+ 592.5 (Method 2minLowpHv03)

Step 5: 8-(Aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione Ethanolamine (108 µl, 1.790 mmol) was added to a solution of 10-(5-chlorofuran-2-yl)-8-((1,3-dioxoisoindolin-2-yl)methyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione (106 mg, 0.179 mmol) in toluene (3087 µl). The mixture was stirred at 70° C. for 6.5 hours then at room temperature for 16 hours. The mixture was diluted with water (50 ml) and extracted with ethyl acetate (50 ml). The organic phase was washed with 1M NaOH(aq) (20 ml) passed through a hydrophobic frit and evaporated under vacuum to afford the title compound as a mixture of diastereomers.
LC-MS Rt 0.74 min [M+H]+ 462.4 and Rt 0.78 min [M+H]+ 462.4 (Method 2minLowpHv03)

Step 6: 4-Bromo-N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]oxazin-8-yl)methyl)butanamide 4-Bromobutyryl chloride (29.4 mg, 0.158 mmol) was added to a solution of 8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione (61 mg, 0.132 mmol) and triethylamine (0.022 mL, 0.158 mmol) in DCM (4 mL). The mixture was stirred at room temperature for 3.5 hours, then diluted with DCM (30 ml) and washed with saturated NaHCO$_3$(aq) (30 ml). The organic phase was passed through a hydrophobic frit and evaporated under vacuum to afford the title compound as a crude material which was used directly

Step 7: 10-(5-Chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione Sodium hydride (60% wt in mineral oil, 26.8 mg, 0.671 mmol) was added to a solution of 4-bromo-N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]oxazin-8-yl)methyl)butanamide (82 mg, 0.134 mmol) in THF (6711 µl). The mixture was heated at reflux for 1 hour, then cooled to room temperature and quenched with water (30 ml). The mixture was extracted with ethyl acetate (2×30 ml). The combined organic extracts were washed with brine, passed through a hydrophobic frit and evaporated under vacuum to afford the title compound as a mixture of diastereomers.
LC-MS Rt 1.20 min [M+H]+ 530.4 (Method 2minLowpHv03)

Step 8: 10-(5-Chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione Purification of racemic 10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione by SFC under the following conditions afforded the title compound as crude materials.
Column: Chiralcel OD-H 250×10 mm, 5 um at 35° C.
Mobile phase: 40% Isopropanol+0.1% v/v DEA/60% CO2
Flow: 10 ml/min
Column temperature: 35 deg C.
Detection: UV @ 220 nm

Example 16

Diastereomer 1 of (5-Chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione SFC Rt=5.18 mins
Final purification of this diastereomer by mass-directed HPLC under the following conditions afforded the title compound.
Column: XSelect CSH Prep C18 column, 30×100 mm, 5 um.
Mobile phase: A=0.1% FA in water, B=0.1% FA in MeCN Gradient:

0.0-0.5 min: 30% B 30 mL/min 0.5-1.0 min: 30% B 30-50 mL/min 1.0-7.2 min: 30-70% B, 7.2-7.3 min: 70-98% B, 7.3-9.4 min: 98% B 9.4-9.5 min: 30% B 50 mL/min 1H NMR (CDCl3, 400 MHz) δ 7.10 (s, 1H), 6.44 (s, 1H), 6.15 (d, 1H), 6.09 (d, 1H), 4.87 (dd, 1H), 4.07 (m, 1H), 3.92 (dd, 1H), 3.65 (dd, 2H), 3.46 (m, 1H), 3.43 (s, 3H), 3.38 (s, 3H), 3.35 (m, 1H), 2.54 (s, 3H), 2.38 (m, 2H), 2.07 (m, 2H)

LC-MS Rt 1.20 min [M+H]$^+$ 530.5 (Method 2minLowpHv03)

Preparation of Intermediates

Intermediate A 6-(2-Amino-ethyl)-1,3-dimethyl-5-phenyl-1,6-dihydro-pyrrolo[3,4-d]pyrimidine-2,4-dione

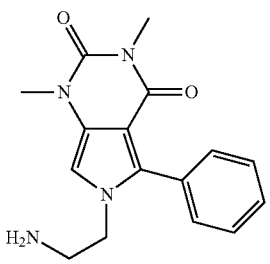 [SMILES: Cn1c(=O)c2c(-c3ccccc3)n(CCN)cc2n(C)c1=O]

Step 1: 1,3,6-Trimethylpyrimidine-2,4(1H,3H)-dione

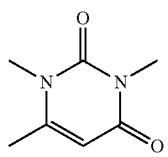

To a stirred suspension of N,N'-dimethylurea (commercial) (72.1 g, 819 mmol) and DMAP (commercial) (100 g, 819 mmol) in pyridine (300 mL) under N$_2$ was added dropwise with stirring acetic anhydride (255 mL, 2701 mmol). On complete addition the reaction mixture was allowed to stir at RT for 3 hours. After this time, the volatiles were removed under reduced pressure to afford a viscous orange pyridine solution, which was seeded with product. The mixture was stored at 0-4° C. for 7 days. The resulting crystalline solid was filtered under reduced pressure, washed with diethyl ether and dried to afford the title compound as colourless crystals. The mother liquors were further purified by chromatography on silica eluting with 30-50% EtOAc in iso-hexane. The resulting solid was diluted with diethyl ether (500 mL) and was stored at 0-4° C. overnight. The resulting crystals were filtered off and washed with iso-hexane, then dried to afford the title compound as colourless crystals and combined. The title product was obtained as white crystals.

$^1$H NMR (400 MHz, CDCl$_3$) δ 5.58 (1H, s), 3.38 (3H, s), 3.30 (3H, s), 2.22 (3H, 5); LC-MS Rt=0.55 min [M+H]+ 155.4 (method: 2minLC_v003).

Step 2: 5-Benzoyl-1,3,6-trimethylpyrimidine-2,4(1H,3H)-dione

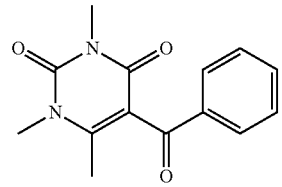 [SMILES: Cc1c(C(=O)c2ccccc2)c(=O)n(C)c(=O)n1C]

1,3,6-Trimethylpyrimidine-2,4(1H,3H)-dione (step 1) (5 g, 32.4 mmol) and chlorobenzene (50 mL) were charged to a 3 necked flask, and the vessel evacuated with nitrogen. Benzoyl chloride (commercial) (11.2 mL, 97 mmol) was added followed by zinc (II) chloride (5 g, 36.7 mmol) in one portion and the reaction was heated to 110° C. for 16 h. The reaction was cooled to RT then poured into water (100 mL) and EtOAc (100 mL). The layers were separated and the aqueous extracted with EtOAc (2×150 mL). The combined organics were washed with water (100 mL) and dried (Na$_2$SO$_4$), filtered under reduced pressure and evaporated to leave an orange solid. The solid was washed with hexane followed by hot diethyl ether, affording the product as an off white solid. The mother liquors were further purified by chromatography on silica, eluting with 10%-100% EtOAc/hexane. The title product was obtained as a pale orange solid.

1H NMR (400 MHz, CDCl$_3$) δ 7.89 (2H, dd), 7.60 (1H, t), 7.48 (2H, t), 3.52 (3H, s), 3.38 (3H, s), 2.26 (3H, 5);

LCMS Rt=0.80 min [M+H]+ 259 (Method 2minLC_v003).

Step 3: 5-Benzoyl-6-(bromomethyl)-1,3-dimethylpyrimidine-2,4(1H,3H)-dione

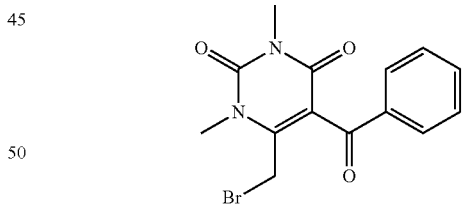

Bromine (0.497 mL, 9.68 mmol) was added to a solution of 5-benzoyl-1,3,6-trimethyl pyrimidine-2,4(1H,3H)-dione (step 2) (2.5 g, 9.68 mmol) in chloroform (50 mL) with stirring under nitrogen. The mixture was heated to 55° C. for 2 h. A further portion of bromine (0.25 mL, 0.5 equiv) was added and heating continued at 55° C. for a further 30 min. The mixture was cooled to RT, diluted with CHCl$_3$ (50 mL) and poured into saturated sodium thiosulfate solution (150 mL). The layers were separated and the aqueous phase was extracted with CHCl$_3$ (50 mL). The combined organics were washed with water (50 mL), brine (50 mL), dried (Na$_2$SO$_4$) and filtered under reduced pressure. The solvent was evaporated under reduced pressure to afford a pale yellow solid. This solid was dissolved in hot EtOAc (50 mL) and slowly evaporated until crystallisation was observed. The resulting white solid was collected by reduced pressure filtration and washed with cold EtOAc (10 mL) and dried in air. The compound was further dried under vacuum at 50° C. for 2 h. The title product was isolated as white micro needles.

$^1$H NMR (400 MHz, DMSO-d$_6$) δ 7.90 (2H, d), 7.67 (1H, t), 7.52 (2H, t), 4.40 (2H, s), 3.50 (3H, s), 3.17 (3H, s);

LC-MS Rt=2.75 min [M+H]+ 337/339 (Method 10min-LC_v003).

Step 4: [2-(1,3-Dimethyl-2,4-dioxo-5-phenyl-1,2,3,4-tetrahydro-pyrrolo[3,4-d]pyrimidin-6-yl)-ethyl]-carbamic acid tert-butyl ester

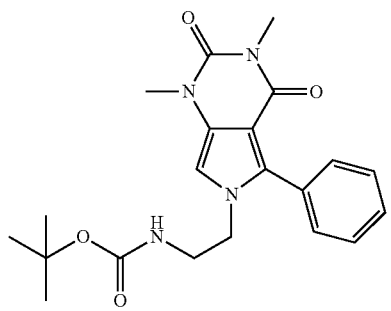 [SMILES: Cn1c(=O)c2c(-c3ccccc3)n(CCNC(=O)OC(C)(C)C)cc2n(C)c1=O]

5-Benzoyl-6-(bromomethyl)-1,3-dimethyl-1H-pyrimidine-2,4-dione (step 3) (1 g, 2.97 mmol) in EtOH (12 mL) was treated with TEA (0.41 mL, 2.97 mmol) and tert-butyl 2-aminoethylcarbamate (commercial) (0.465 mL, 2.97 mmol). The mixture was heated to 100° C. for 1 h using microwave irradiation. After this time, a white precipitate had formed. The solid was collected via reduced pressure filtration and was washed with diethyl ether. The title compound was obtained as white needles.

$^1$H NMR (400 MHz, CDCl$_3$) δ 7.49-7.42 (5H, m), 6.43 (1H, bs), 4.50 (1H, bs), 4.05 (2H, t), 3.43 (3H, s), 3.36 (3H, s), 3.34 (2H, m), 1.42 (9H, s);

LCMS Rt=1.06 min [M+H]+ 399 (Method 2min-LC_v003).

Step 5: 6-(2-Amino-ethyl)-1,3-dimethyl-5-phenyl-1,6-dihydro-pyrrolo[3,4-d]pyrimidine-2,4-dione

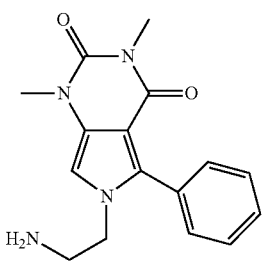 [SMILES: Cn1c(=O)c2c(-c3ccccc3)n(CCN)cc2n(C)c1=O]

[2-(1,3-Dimethyl-2,4-dioxo-5-phenyl-1,2,3,4-tetrahydro-pyrrolo[3,4-d]pyrimidin-6-yl)-ethyl]-carbamic acid tert-butyl ester (step 4) (1.11 g, 2.79 mmol) was dissolved in DCM (10 mL) and treated with trifluoroacetic acid (2.1 mL, 25.1 mmol). The reaction was stirred at RT for 4 h. The reaction was quenched by pouring into stirring 2M NaOH and further NaOH added until alkaline to pH paper. The layers were separated and the aqueous phase extracted with DCM (3×75 mL). The combined organic phases were washed with water (100 mL), brine (75 mL) and passed through a hydrophobic frit. The solvent was removed under reduced pressure, affording the title compound as an off-white solid.

$^1$H NMR (400 MHz, CDCl$_3$) δ 7.52-7.45 (5H, m), 6.48 (1H, s), 3.98 (2H, t), 3.44 (3H, s), 3.36 (3H, s), 2.97 (2H, t), 1.27 (1H, br s);

LC-MS Rt=0.72 min [M+H]+ 299 (Method 2min-LC_v003).

Intermediate Aa 6-(2-Amino-ethyl)-5-(4-fluoro-phenyl)-1,3-dimethyl-1,6-dihydro-pyrrolo[3,4-d]pyrimidine-2,4-dione

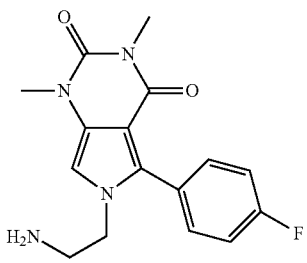 [SMILES: Cn1c(=O)c2c(-c3ccc(F)cc3)n(CCN)cc2n(C)c1=O]

This compound was prepared analogously to Intermediate A by replacing benzoyl chloride (step 2) with 4-fluorobenzoyl chloride.

$^1$H NMR (400 MHz, DMSO-d6) δ 7.51 (2H, dd), 7.29 (2H, t), 6.96 (1H, s), 3.82 (2H, t), 3.21 (3H, s), 3.14 (3H, s), 2.79 (2H, t), 1.57 (2H, br s);

LC-MS Rt=0.74 min [M+H]+ 317 (Method 2min-LC_v003).

Intermediate Ab 6-(2-Aminoethyl)-1,3-dimethyl-5-(m-tolyl)-1H-pyrrolo[3,4-d]pyrimidine-2,4(3H,6H)-dione

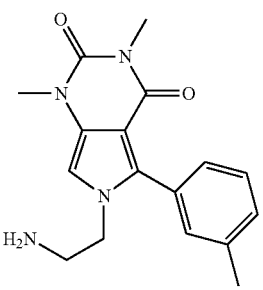 [SMILES: Cc1cccc(-c2c3c(=O)n(C)c(=O)n(C)c3cn2CCN)c1]

This compound was prepared analogously to Intermediate A by replacing benzoyl chloride (step 2) with 3-methylbenzoyl chloride (commercial).

LC-MS: Rt 0.58 mins; MS m/z 313 [M+H]+; Method 2minLowpH

Intermediate B 6-(2-Amino-ethyl)-5-(3-chloro-phenyl)-1,3-dimethyl-1,6-dihydro-pyrrolo[3,4-d]pyrimidine-2,4-dione

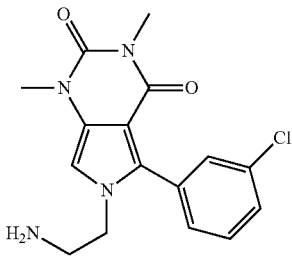 [SMILES: Cn1c(=O)c2c(-c3cccc(Cl)c3)n(CCN)cc2n(C)c1=O]

Step 1 1,3-Dimethyl-1H-pyrrolo[3,4-d]pyrimidine-2,4(3H,6H)-dione)

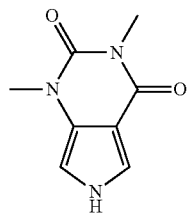

1,3-Dimethylpyrimidine-2,4(1H,3H)-dione (commercial (40 g, 285 mmol) and 1-(isocyano methylsulfonyl)-4-methylbenzene (commercial) (84 g, 428 mmol) were dissolved in 2-MeTHF (1000 mL) under nitrogen at 30° C. and held for 5 mins. The vessel was then cooled to 0° C. (internal). A solution of KOtBu (commercial) (64.1 g, 571 mmol) in 2-MeTHF (500 mL was added to the solution via a dropping funnel over 0.5 h, such that the internal temperature remained below 5° C. On addition of the KOtBu solution, an orange precipitate formed. An additional portion of 2-MeTHF (455 mL) was charged via dropping funnel over 5 mins. After 40 mins, the dark orange suspension was quenched with sat NH$_4$Cl solution (2×400 mL) charged via dropping funnel over 15 mins. The suspension was then diluted with EtOAc (1 L), the layers were separated and the aqueous extracted with EtOAc (3×1 L). The combined organics were dried (MgSO$_4$) and filtered under reduced pressure. The solvent was removed under reduced pressure to afford a brown semi-solid. The solids were suspended in MeOH (300 mL), sonicated and stirred at room temperature for 15 mins, filtered by reduced pressure filtration and washed with MeOH (100 mL). The solid was dried under vacuum at 50° C. for 24 h. The title compound was obtained as a pale brown amorphous solid (26.34 g, 52%)

LC-MS: Rt 0.59 mins; not ionised; Method 2minLowpHv01; indicates purity of >95 area %. A second crop of material could be obtained by evaporation of the MeOH to afford a red oil. Trituration with MeOH (50 mL), filtration under reduced pressure and washing with MeOH (20 mL) and drying under vacuum at 50° C. for 16 h afforded the title compound as a pale brown amorphous solid (1.03 g, 2%)

1H NMR (400 MHz, DMSO-d6) δ 11.82 (1H, s), 7.43 (1H, dd), 6.74 (1H, t), 3.29 (3H, s), 3.19 (3H, s).

Step 2 tert-Butyl 1,2,3-oxathiazolidine-3-carboxylate 2,2-dioxide

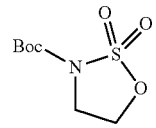

Step A tert-Butyl-2-hydroxyethylcarbamate (commercial), (6.19 ml, 40 mmol) was dissolved in anhydrous MeCN (18 mL) under nitrogen. The solution was added dropwise to a solution of SOCl$_2$ (commercial) (3.65 ml, 50.0 mmol) in anhydrous MeCN (200 ml) at −20° C. (internal), such that the internal temperature did not rise above −15° C. Anhydrous MeCN (2 mL) was used to rinse dropping funnel and this was added to reaction. After 10 min, anhydrous pyridine (12.94 ml, 160 mmol) was charged dropwise over 10 min via dropping funnel, keeping the temperature kept below −15° C. The reaction was then stirred for 1 h at −20° C., followed by a further 1 h at 0° C. After this time, the reaction was quenched by the addition of water (50 mL) and EtOAc (50 mL). The layers were separated and the organic layer washed with 1M HCl (100 mL); the aqueous layer was then extracted with EtOAc (100 mL). The combined organics were washed with saturated NaHCO$_3$ (100 mL), water (100 mL), brine (100 mL), dried (Na$_2$SO$_4$) and filtered under reduced pressure. The solvents were removed under reduced pressure to afford a dark orange oil.

Step B

The oil from step A was dissolved in MeCN (160 ml) and cooled to 0° C. (internal). Ruthenium(III) chloride hydrate (commercial) (0.045 g, 0.200 mmol) was charged followed by NaIO$_4$ (commercial) (12.83 g, 60.0 mmol) and water (160 ml). The reaction was stirred vigorously at 0° C. for 1 h, then quenched by the addition of water (80 mL). Diethylether (100 mL) was charged and the layers separated; the aqueous phase was extracted with ether (3×100 mL) and the combined organics were washed with water (60 mL) until black/green colour was removed. The organics were dried (Na$_2$SO$_4$) and filtered under reduced pressure; the solvent was removed under reduced pressure to afford a white solid. The solid was suspended in boiling MTBE (110 mL) and the suspension filtered whilst hot (>80° C.). The colourless solution was allowed to cool slowly to room temperature overnight, affording white needles. The needles were collected by reduced pressure filtration and then dried under vacuum at 50° C. for 2 h. The title compound was isolated as white needles;

1H NMR (400 MHz, CDCl$_3$) δ 4.62 (2H, t); 4.06 (2H, t); 1.57 (9H, s).

Step 3. [2-(1,3-Dimethyl-2,4-dioxo-1,2,3,4-tetrahydro-pyrrolo[3,4-d]pyrimidin-6-yl)-ethyl]-carbamic acid tert-butyl ester

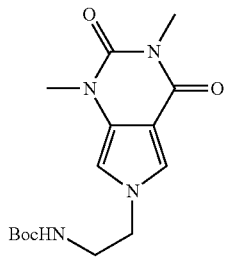 [SMILES: Cn1c(=O)c2cn(CCNC(=O)OC(C)(C)C)cc2n(C)c1=O]

1,3-Dimethyl-1H-pyrrolo[3,4-d]pyrimidine-2,4(3H,6H)-dione) (step 1) (4.43 g, 24.72 mmol) and sodium hydride (commercial) (60% dispersion in mineral oil) (1.286 g, 32.1 mmol) were degassed with nitrogen for 15 min. The reagents were then suspended in anhydrous THF (44.5 mL) and stirred for 15 mins at room temperature, then cooled to 0° C. (external). After 10 mins, a solution of tert-butyl-1,2,3-oxathiazolidine-3-carboxylate 2,2-dioxide (step 2) (6.07 g, 27.2 mmol) in anhydrous THF (44.5 mL) was charged in two portions (2×24 mL). After addition was complete, the ice-bath was removed and the reaction stirred at room temperature for 50 mins. The reaction was then quenched by addition of saturated NH$_4$Cl solution (30 mL). The reaction mixture was diluted with water (30 mL), EtOAc (60 mL) and the layers separated. The aqueous layer was extracted with EtOAc (2×50 mL), saturated with NaCl (s) and extracted with MeCN (4×50 mL). The aqueous layer was evaporated to (~20 mL) and extracted further with MeCN (3×50 mL). The combined organic layers were dried (Na$_2$SO$_4$) and filtered under reduced pressure and the solvent was evaporated. The resulting solid was adsorbed onto silica and purified via ISCO SiO$_2$ 125 g column eluting with 60-95% EtOAc/hexane. The fractions containing product were combined and evaporated to afford a white crystalline solid. The solid was dried under vacuum at 50° C. for 3 h. The title compound was afforded as a white crystalline solid.

LC-MS: Rt 0.81 mins; MS m/z 323 [M+H]$^+$; (Method 2minLowpH).

1H NMR (400 MHz, DMSO-d$_6$) δ 7.42 (1H, d), 6.95 (1H, t), 6.76 (1H, d), 4.03 (2H, t), 3.29 (2H, q), 3.27 (3H, s), 3.20 (3H, s), 1.35 (9H, s).

Step 4. (6-(2-((tert-Butoxycarbonyl)amino)ethyl)-1,3-dimethyl-2,4-dioxo-2,3,4,6-tetrahydro-1H-pyrrolo[3,4-d]pyrimidin-5-yl)boronic acid

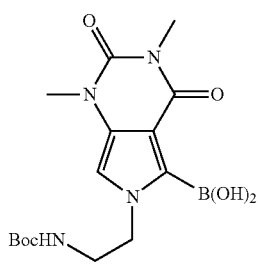 [SMILES: Cn1c(=O)c2c(B(O)O)n(CCNC(=O)OC(C)(C)C)cc2n(C)c1=O]

2-(1,3-Dimethyl-2,4-dioxo-1,2,3,4-tetrahydro-pyrrolo[3,4-d]pyrimidin-6-yl)-ethyl]-carbamic acid tert-butyl ester (step 3) (1.8 g, 5.58 mmol) was dissolved in anhydrous THF (49 ml) at room temperature. The flask was then evacuated and backfilled with nitrogen (×3) and cooled to −78° C. (external). After 10 mins, LDA (0.731 M, 22.92 ml, 16.75 mmol in THF, freshly prepared by standard procedure from BuLi and diisopropylamine) was charged over 3 mins. After 15 mins at −78° C., triisopropyl borate (3.87 ml, 16.75 mmol) was charged drop wise over 2 mins and the reaction held for 2 hr at −78° C. The reaction was then quenched with saturated NH$_4$Cl solution (10 mL) via syringe under nitrogen and diluted with water (60 mL) and EtOAc (40 mL). The layers were separated and the aqueous extracted with EtOAc (4×50 mL). The combined organics were washed with brine (20 mL), dried (Na$_2$SO$_4$) and filtered under reduced pressure to afford a pale yellow solution. The solvent volume reduced by half under reduced pressure to afford a suspension of a white solid. The solid was recovered by reduced pressure filtration and dried in air, followed by heating to 50° C. under vacuum for 3 h. This afforded the title compound as a white crystalline solid.

LC-MS: Rt 0.86 mins; MS m/z 367 [M+H]+; (Method 2minLowpH).

1H NMR (400 MHz, DMSO-d$_6$) δ 9.62 (2H, s), 6.96 (1H, s), 6.82 (1H, t), 4.41 (2H, t), 3.32 (3H, s), 3.30 (2H, m), 3.28 (3H, s), 1.32 (9H, s).

Step 5. {2-[5-(3-Chloro-phenyl)-1,3-dimethyl-2,4-dioxo-1,2,3,4-tetrahydro-pyrrolo[3,4-d]pyrimidin-6-yl]-ethyl}-carbamic acid tert-butyl ester

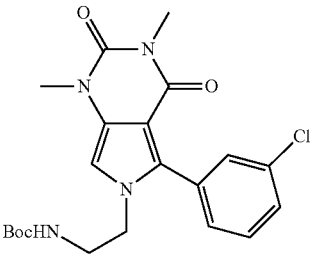 [SMILES: Cn1c(=O)c2c(-c3cccc(Cl)c3)n(CCNC(=O)OC(C)(C)C)cc2n(C)c1=O]

(6-(2-((tert-Butoxycarbonyl)amino)ethyl)-1,3-dimethyl-2,4-dioxo-2,3,4,6-tetrahydro-1H-pyrrolo[3,4-d]pyrimidin-5-yl)boronic acid (step 4) (631 mg, 1.724 mmol), Pd-118 (commercial, CAS 95408-45-0) (51.1 mg, 0.078 mmol, 5 mol %) and potassium carbonate (433 mg, 3.13 mmol) were suspended in n-butylacetate (11.2 mL). The vessel was evacuated and back filled with N$_2$ (×4). Under a stream of N$_2$ was charged 1-bromo-3-chlorobenzene (commercial) (0.184 mL, 1.567 mmol) and water (0.056 mL, 3.13 mmol). The vessel was heated to 80° C. for 2 hrs under microwave irradiation. An additional amount of water (100 μL) and 1-bromo-3-chlorobenzene (0.184 mL, 1.567 mmol) was charged and the mixture heated to 80° C. for a further 2 hrs under microwave irradiation. The reaction mixture was diluted with water (40 mL) and EtOAc (20 mL) and the layers were separated. The aqueous was extracted with EtOAc (4×20 mL) and the combined organics were washed with brine (20 mL), dried (Na$_2$SO$_4$) and filtered under reduced pressure. Silica gel was added to the solution and the solvent evaporated under reduced pressure. The residue was purified via ISCO SiO$_2$ 80 g RediSep® Rf column eluting with 50-70% EtOAc/hexane. The fractions containing product were combined and evaporated to afford a pale tan solid, which was dried under vacuum at 50° C. for 3 hrs. This afforded the title product as a pale tan solid.

LC-MS: Rt 1.04 mins; MS m/z 433/435 [M+H]+; (Method 2minLowpH).

1H NMR (400 MHz, CDCl₃) δ 7.48-7.40 (3H, m), 7.37-7.32 (1H, m), 6.45 (1H, s), 4.50 (1h, br s), 4.05 (2H, t), 3.43 (3H, s), 3.36 (3H, s), 3.35 (2H, q), 1.43 (9H, s).

Step 6: 6-(2-Amino-ethyl)-5-(3-chloro-phenyl)-1,3-dimethyl-1,6-dihydro-pyrrolo[3,4-d]pyrimidine-2,4-dione

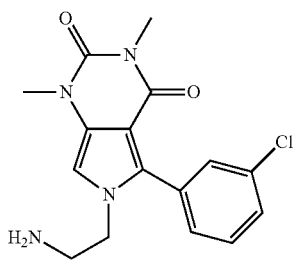

{2-[5-(3-Chloro-phenyl)-1,3-dimethyl-2,4-dioxo-1,2,3,4-tetrahydro-pyrrolo[3,4-d]pyrimidin-6-yl]-ethyl}-carbamic acid tert-butyl ester (step 5) (429 mg, 0.991 mmol) was dissolved in DCM (10 ml). TFA (1.374 ml, 17.84 mmol) was charged in 2 portions and the reaction stirred under nitrogen. After 2 hrs, the pH of the mixture was adjusted to pH 11 with saturated K₃CO₃ solution (20 mL). The layers were separated and the aqueous extracted with DCM (4×20 mL). The combined organics were passed through a hydrophobic frit and evaporated under reduced pressure to afford a tan solid, which was dried under vacuum at 50° C. for 5 h to afford the title compound as a tan solid.

LC-MS: Rt 0.58 mins; MS m/z 333/335 [M+H]⁺; (Method 2minLowpH).

1H NMR (400 MHz, CDCl₃) δ 7.5-7.31 (4H, m), 6.50 (1H, s), 3.97 (2H, t), 3.43 (3H, s), 3.36 (3H, s), 2.99 (2H, t), 1.29 (2H, br s).

Intermediate Ba 6-(2-Aminoethyl)-1,3-dimethyl-5-(3-(trifluoromethyl)phenyl)-1H-pyrrolo[3,4-d]pyrimidine-2,4(3H,6H)-dione

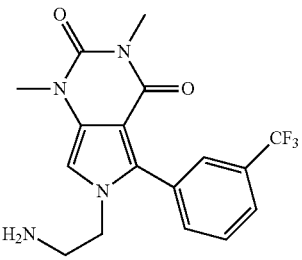 [SMILES: Cn1c(=O)c2c(-c3cccc(C(F)(F)F)c3)n(CCN)cc2n(C)c1=O]

The title compound was prepared analogously to Intermediate B by replacing 1-bromo-3-chlorobenzene with 1-bromo-3-(trifluoromethyl)benzene;

LC-MS: Rt 0.62 mins; MS m/z 367.5 [M+H]+; Method 2minLowpH

Intermediate Bb 6-(2-Aminoethyl)-5-(3-methoxyphenyl)-1,3-dimethyl-1H-pyrrolo[3,4-d]pyrimidine-2,4(3H,6H)-dione

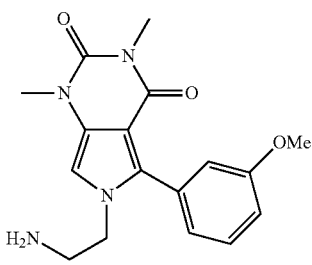 [SMILES: COc1cccc(-c2c3c(=O)n(C)c(=O)n(C)c3cn2CCN)c1]

The title compound was prepared analogously to Intermediate B by replacing 1-bromo-3-chlorobenzene with 3-bromoanisole;

LC-MS: Rt 0.63 mins; MS m/z [M+H]+; Method 2minLowpH

Intermediate Bc 6-(2-Aminoethyl)-5-(3,5-dimethylphenyl)-1,3-dimethyl-1H-pyrrolo[3,4-d]pyrimidine-2,4(3H,6H)-dione

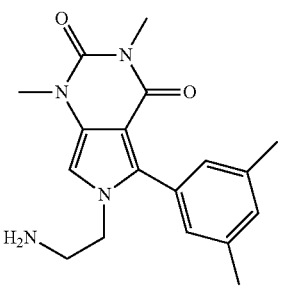

The title compound was prepared analogously to Intermediate B by replacing 1-bromo-3-chlorobenzene with 1-bromo-3,5-dimethylbenzene;

LC-MS: Rt 0.69 mins; MS m/z 327.5 [M+H]+; Method 2minLowpH

Intermediate Bd

Methyl 3-(6-(2-aminoethyl)-1,3-dimethyl-2,4-dioxo-2,3,4,6-tetrahydro-1H-pyrrolo[3,4-d]pyrimidin-5-yl)benzoate

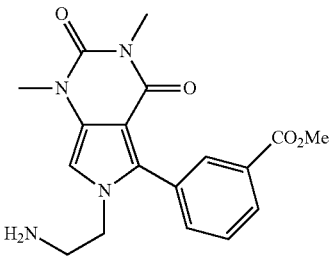 [SMILES: COC(=O)c1cccc(-c2c3c(=O)n(C)c(=O)n(C)c3cn2CCN)c1]

The title compound was prepared analogously to Intermediate B by replacing 1-bromo-3-chlorobenzene with methyl 3-bromobenzoate;

LC-MS: Rt 0.98 mins; MS m/z 457 [M+H]+; Method 2minLowpH

Intermediate Be 3-(6-(2-Aminoethyl)-1,3-dimethyl-2,4-dioxo-2,3,4,6-tetrahydro-1H-pyrrolo[3,4-d]pyrimidin-5-yl)benzonitrile

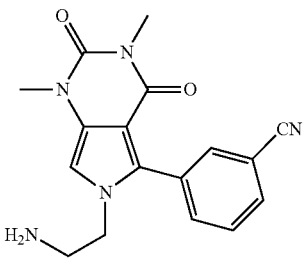 [SMILES: Cn1c(=O)c2c(-c3cccc(C#N)c3)n(CCN)cc2n(C)c1=O]

The title compound was prepared analogously to Intermediate B by replacing 1-bromo-3-chlorobenzene with 3-bromobenzonitrile.

LC-MS Rt 0.52 mins [M+H]+ 324.4 (Method 2min-LowpH)

Intermediate Bf 6-(2-Aminoethyl)-1,3-dimethyl-5-(4-methylthiazol-2-yl)-1H-pyrrolo[3,4-d]pyrimidine-2,4(3H,6H)-dione

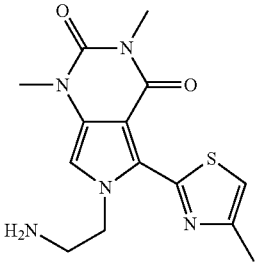

The title compound was prepared analogously to Intermediate B by replacing 1-bromo-3-chlorobenzene with 2-iodo-4-methylthiazole (Intermediate F)

LC-MS Rt 0.64 mins [M+H]+ 320.4 (Method 2minHighpHv01)

Intermediate C 6-(2-Hydroxyethyl)-1,3-dimethyl-5-phenyl-1H-pyrrolo[3,4-d]pyrimidine-2,4(3H,6H)-dione

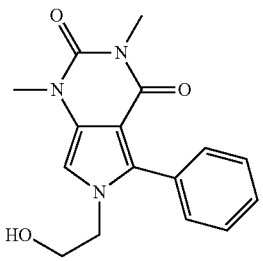 [SMILES: Cn1c(=O)c2c(-c3ccccc3)n(CCO)cc2n(C)c1=O]

5-Benzoyl-6-(bromomethyl)-1,3-dimethylpyrimidine-2,4(1H,3H)-dione (Intermediate A step 3) (400 mg 1.19 mmol) in EtOH (4 mL) was treated with TEA (0.16 mL, 1.19 mmol) and ethanolamine (72.5 mg, 1.19 mmol). The mixture was heated to 100° C. for 1 h under microwave irradiation. A further portion of ethanolamine (96 μL) was added and heating continued for a further 20 min. The reaction was poured into DCM (75 mL) and water (75 mL). The layers were separated and the aqueous phase extracted with DCM (2×50 mL). The combined organic phases were washed with water (2×50 mL), then passed through a hydrophobic frit. The solvent was removed under reduced pressure affording a pale yellow solid. The solid was triturated in hot EtOH and allowed to cool. The title product was collected by reduced pressure filtration as a white powder.

1H NMR (400 MHz, CDCl$_3$) δ 7.48-7.45 (5H, m), 6.54 (1H, s), 4.07 (2H, t), 3.87 (2H, m), 3.42 (3H, s), 3.35 (3H, s), 1.69 (1H, br s), 1.56 (1H, br S);

LC-MS Rt=0.83 min [M+H]+ 300 (Method 2min-LC_v003).

Intermediate D 6-((R)-2-Hydroxy-1-methyl-ethyl)-1,3-dimethyl-5-phenyl-1,6-dihydro-pyrrolo[3,4-d]pyrimidine-2,4-dione

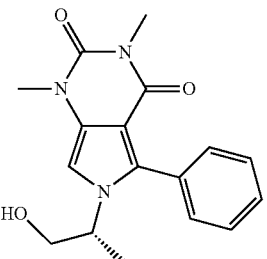

5-Benzoyl-6-(bromomethyl)-1,3-dimethyl-1H-pyrimidine-2,4-dione (Intermediate A step 3) (200 mg 0.59 mmol), triethylamine (82 μl, 0.59 mmol) and (R)-2-aminopropan-1-ol (45 mg, 0.59 mmol) (commercial) were combined in EtOH (2 mL). The mixture was heated at 100° C. under microwave irradiation for 1 hour. The solvent was evaporated under reduced pressure. The solid residue dissolved in DCM and water and extracted (×3). The combined organic phases were washed with water, passed through a hydrophobic frit and evaporated under reduced pressure to afford the title compound as an off-white solid.

1H NMR (400 MHz, CDCl$_3$) δ 7.46-7.44 (5H, m); 6.54 (1H, s); 4.06-4.00 (1H, m); 3.96-3.82 (2H, m); 3.41 (3H, s); 3.35 (3H, s); 1.11 (3H, d).

LCMS Rt=0.82 min [M+H]+ 314 (Method 2minLowpH).

Intermediate Ea (S)-(2,2-Dimethyl-1,3-dioxolan-4-yl)methyl trifluoromethanesulfonate

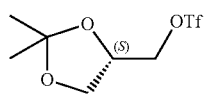

Trifluoromethanesulfonic anhydride (1.398 ml, 8.32 mmol) was added dropwise to a solution of commercially available R-solketal (1 g, 7.57 mmol) and 2.6-lutidine (1.139 ml, 9.84 mmol) in DCM (25.2 mL) at 0° C. The mixture was warmed to room temperature and stirred for 1 hour. The mixture was then evaporated under vacuum and the residue partitioned between water (10 mL) and DCM (20 mL). The phases were separated and the aqueous phase was extracted with DCM (3×10 mL). The combined organic extracts were dried over magnesium sulfate to afford the title compound as a crude material which was used without further purification.

Intermediate Eb (2,2-Dimethyl-1,3-dioxolan-4-yl)methyl trifluoromethanesulfonate

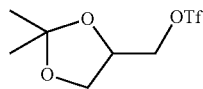

The title compound was prepared by an analogous method to Intermediate Ea from commercially available racemic solketal.

Intermediate F

2-Iodo-4-methylthiazole

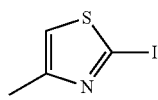

Methyllithium solution (1.6 M in Et$_2$O, 189 ml, 303 mmol) was added dropwise to 4-methylthiazole (22.94 ml, 252 mmol) in diethyl ether (505 ml) at −78° C. The mixture was stirred for 30 mins at −78° C., then iodine (83 g, 328 mmol) was added and the suspension slowly warmed to 0° C. and stirred for 45 mins. The reaction was quenched by the addition of water (150 ml), diluted with diethyl ether (100 ml) and the layers separated. The aqueous phase was extracted with diethyl ether (2×200 ml) and the combined organic phases were washed with saturated aqueous sodium thiosulfate solution (150 ml), 2M Na$_2$CO$_3$(aq) (100 ml), water (100 ml) and brine (100 ml), dried over magnesium sulfate and evaporated under vacuum. Purification by chromatography on silica, eluting with 0-5% TBME/iso-hexane afforded the title compound.

1H NMR (400 MHz, CDCl3) δ 6.87 (1H, s), 2.48 (3H, s)

LC-MS Rt 1.00 mins [M+H]$^+$ 2.26 (Method 2minLowpHv03)

Intermediate Ga 3-(1,3-Dimethyl-2,4-dioxo-2,3,4,6-tetrahydro-1H-pyrrolo[3,4-d]pyrimidin-5-yl)benzonitrile

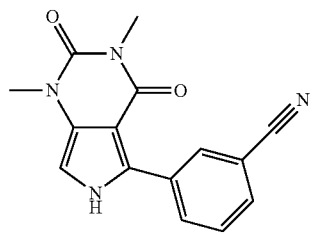 [SMILES: Cn1c(=O)c2c(-c3cccc(C#N)c3)[nH]cc2n(C)c1=O]

Step 1: 1,3-Dimethyl-6-((2-(trimethylsilyl)ethoxy)methyl)-1H-pyrrolo[3,4-d]pyrimidine-2,4(3H,6H)-dione Sodium hydride (60% in mineral oil, 335 mg, 8.4 mmol) was added to an ice cooled partial suspension of 1,3-dimethyl-1H-pyrrolo[3,4-d]pyrimidine-2,4(3H,6H)-dione (Intermediate B step 1) (1.00 g, 5.6 mmol), SEM-Cl (1.485 mL, 8.4 mmol) and benzyl triethylammonium chloride (76 mg, 0.34 mmol) in THF (15 mL). The mixture was allowed to reach room temperature slowly and was stirred for 18 hours. The reaction mixture was quenched cautiously with sat ammonium chloride solution (80 mL, added dropwise), then was extracted with ethyl acetate (3×40 mL). The combined organic layers were washed with water (1×40 mL), brine (1×40 mL) then dried with magnesium sulfate and the solvent was removed under vacuum. The residue was triturated with iso-hexane and dried under vacuum at 50° C. to afford the title compound.

1H NMR (400 MHz, CDCl3) δ 7.38 (1H, s), 6.47 (1H, s), 5.26 (2H, s), 3.48 (2H, t), 3.41 (3H, s), 3.40 (3H, s), 0.93 (2H, t), 0.00 (9H, s).

LC-MS Rt 1.15 mins; MS m/z 310.4 [M+H]+; (Method 2minLowpHv01)

Step 2: 1,3-Dimethyl-2,4-dioxo-6-((2-(trimethylsilyl)ethoxy)methyl)-2,3,4,6-tetrahydro-1H-pyrrolo[3,4-d]pyrimidin-5-ylboronic acid Butyl lithium (1.26M, 28.4 mL, 35.8 mmol) was added dropwise to a solution of diisopropylamine (3.63 g, 35.8 mmol) in THF (20 mL) at −78° C., keeping the internal temperature below −40° C. Once the addition was complete, the contents of the flask were allowed to warm to −5° C., then were re-cooled to −78° C. The resulting mixture was cannulated over a period of about 30 minutes into a suspension of 1,3-dimethyl-6-((2-(trimethylsilyl)ethoxy)methyl)-1H-pyrrolo[3,4-d]pyrimidine-2,4(3H,6H)-dione (step 1) (6.93 g, 22.4 mmol) in THF (75 mL) at −78° C. The mixture was stirred at −78° C. for 30 minutes, then triisopropylborate (8.3 mL, 35.8 mmol) was added dropwise. The solution was stirred at −78° C. for 1.5 hours, then was quenched by carefully adding sat ammonium chloride (200 mL). The mixture was allowed to reach room temperature and extracted with ethyl acetate (3×100 mL). The combined organic extracts were dried with magnesium sulfate and the solvent was removed under vacuum. The crude material was triturated with ether/hexane and dried under vacuum at 50° C. The solid was recombined with the mother liquor which was reduced under vacuum. The resultant semi-solid material was triturated with iso-hexane and dried under vacuum at 50° C. to afford the title compound;

LC-MS: Rt 1.19 mins; MS m/z 354.4 [M+H]+; (Method 2minLowpHv01)

Step 3: 3-(1,3-Dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile A mixture of 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (step 2) (2.0 g, 5.7 mmol), 3-bromobenzonitrile (937 mg, 5.2 mmol), Pd-118 (168 mg, 0.26 mmol) and potassium carbonate (1.42 g, 10.3 mmol) in n-butyl acetate (40 mL) was heated to 80° C., then water (2.23 mL, 124.0 mmol) was added and the mixture was heated at 80° C. for 90 minutes. The reaction mixture was diluted with water (100 mL), the layers were separated as much as possible, and the aqueous phase (and residual organic portion) was extracted with DCM (1×100 mL, 2×50 mL). The combined organic extracts were washed with brine (1×100 mL), dried with magnesium sulfate and the solvent was removed under vacuum. The resulting residue was re-crystallised from methanol and dried under vacuum at 50° C. to afford the title compound;

1H NMR (400 MHz, CDCl3) δ 7.87-7.82 (2H, mult), 7.74 (1H, d), 7.59 (1H, t), 6.59 (1H, s), 5.14 (2H, s), 3.50 (2H, t), 3.43 (3H, s), 3.56 (3H, s), 0.91 (2H, t), 0.00 (9H, s).

LC-MS: Rt 1.34 mins; MS m/z 411.4 [M+H]+; (Method 2minLowpHv01)

Step 4: 3-(1,3-Dimethyl-2,4-dioxo-2,3,4,6-tetrahydro-1H-pyrrolo[3,4-d]pyrimidin-5-yl)benzonitrile TBAF solution (20.3 mL, 20.3 mmol) was added to a suspension of 3-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile (step 3) (832 mg, 2.0 mmol) in THF (6 mL), giving a solution which was stirred at 60° C. for 1 hour. Most of the organic solvent was removed from the reaction mixture, water (100 mL) was added and the mixture was stirred for 5 minutes The aqueous suspension was extracted with chloroform (4×100 mL). A large amount of the mixture remained as an emulsion. Sat brine (100 mL) was added to break up the emulsion, and the aqueous phase was extracted with more chloroform (4×100 mL). The combined organic extracts were dried with magnesium sulfate and the solvent was removed under vacuum to yield a red oil. The crude red oil was triturated with methanol to give a pink solid which was dried under vacuum at 50° C. The solid was triturated with methanol again and dried under vacuum at 50° C. to afford the title compound.

LC-MS: Rt 0.91 mins; MS m/z 281.4 [M+H]+; (Method 2minLowpHv01)

Intermediate Gb 5-(3-Fluorophenyl)-1,3-dimethyl-1H-pyrrolo[3,4-d]pyrimidine-2,4(3H,6H)-dione

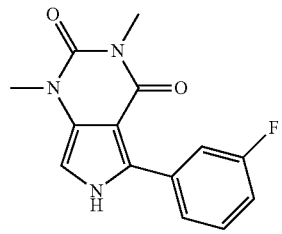 [SMILES: Cn1c(=O)c2c(-c3cccc(F)c3)[nH]cc2n(C)c1=O]

Step 1: 5-(3-fluorophenyl)-1,3-dimethyl-6-((2-(trimethylsilyl)ethoxy)methyl)-1H-pyrrolo[3,4-d]pyrimidine-2,4(3H,6H)-dione A mixture of 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (Intermediate Ga Step 2) (7.31 g, 20.7 mmol), 1-bromo-3-fluorobenzene (2.10 mL, 18.8 mmol), Pd-118 (245 mg, 0.38 mmol), and barium hydroxide (6.44 g, 37.6 mmol) in n-butyl acetate (64 mL) was heated to 80° C. Water (4.06 mL, 226.0 mmol) was added and the mixture was stirred vigorously at 80° C. for 30 minutes. The reaction mixture was cooled to room temperature diluted with 1M HCl(aq) (100 mL) and was extracted with DCM (3×100 mL). The combined organic layers were washed with saturated brine (1×100 mL), dried over magnesium sulfate and the evaporated under vacuum. The residue was recrystallised from methanol to afford the title compound.

1H NMR (400 MHz, CDCl3) δ 7.46 (1H, mult), 7.34 (1H, d), 7.29 (1H, mult), 7.18 (1H, t), 6.59 (1H, s), 5.20 (2H, s), 3.49-3.43 (5H, mult), 3.38 (3H, s), 0.88 (2H, t), 0.00 (9H, s).

LC-MS Rt 1.38 mins [M+H]+ 404.2 (Method 2minLowpHv02)

Step 2: 5-(3-fluorophenyl)-1,3-dimethyl-1H-pyrrolo[3,4-d]pyrimidine-2,4(3H,6H)-dione Tetra-n-butylammonium fluoride solution (1.0M, 24.8 mL, 24.8 mmol) was added to a suspension of 5-(3-fluorophenyl)-1,3-dimethyl-6-((2-(trimethylsilyl)ethoxy)methyl)-1H-pyrrolo[3,4-d]pyrimidine-2,4(3H,6H)-dione (1.00 g, 2.48 mmol) in THF (7 mL), and the mixture was stirred at 60° C. for 2 hours, then cooled to room temperature and stirred for 4 hours. The mixture was concentrated under vacuum and the residue was dissolved in ethyl acetate (50 mL). The mixture was washed with water (3×25 mL) and brine (1×25 mL). The organic phase was dried over magnesium sulfate and the solvent was evaporated under vacuum to afford the title compound.

1H NMR (400 MHz, DMSO-d6) δ 12.28 (1H, br s), 7.94 (1H, d), 7.79 (1H, d), 7.48 (1H, dd), 7.18 (1H, t), 6.94 (1H, s), 3.33 (3H, s)*, 3.24 (3H, s)

LC-MS Rt 0.96 mins [M+H]+ 274.5 (Method 2minLow-pHv01)

Intermediate Gc 1,3-Dimethyl-5-(4-methylthiazol-2-yl)-1H-pyrrolo[3,4-d]pyrimidine-2,4(3H,6H)-dione

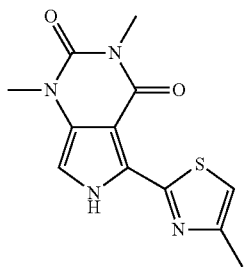

The title compound was prepared by an analogous method to 3-(1,3-dimethyl-2,4-dioxo-2,3,4,6-tetrahydro-1H-pyrrolo[3,4-d]pyrimidin-5-yl)benzonitrile (Intermediate Ga) by replacing 3-bromobenzonitrile (step 3) with 2-iodo-4-methylthiazole (Intermediate F).

LC-MS Rt 0.95 mins [M+H]+ 277.4 (Method 2minLowpHv03).

Intermediate Gd 1,3-Dimethyl-5-(2-methylthiazol-4-yl)-1H-pyrrolo[3,4-d]pyrimidine-2,4(3H,6H)-dione

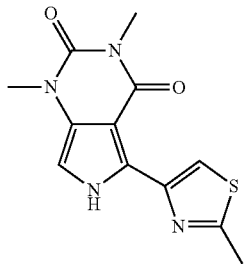

The title compound was prepared by an analogous method to 3-(1,3-dimethyl-2,4-dioxo-2,3,4,6-tetrahydro-1H-pyrrolo[3,4-d]pyrimidin-5-yl)benzonitrile (Intermediate Ga) by replacing 3-bromobenzonitrile (step 3) with 4-bromo-2-methylthiazole.

LC-MS Rt 0.95 mins [M+H]+ 277.4 (Method 2minLowpHv03)

Intermediate H

4-Chlorothiazole-2-carbaldehyde

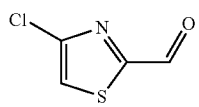

Step 1: 2,5-Dibromo-4-chlorothiazole 2,4-Dichlorothiazole (10 g, 64.9 mmol) was dissolved in acetic acid (50.0 ml) and heated to 60° C. Bromine (15.05 ml, 292 mmol) was added dropwise and the reaction mixture then stirred at 90° C. for 5.5 hours. The reaction was cooled to room temperature and made basic by slow addition of solid sodium carbonate, then diluted with water (100 mL) and extracted with Et₂O (3×150 ml). The combined organic extracts were washed with sat.aq. sodium thiosulfate (50 ml) dried over sodium sulfate evaporated under reduced pressure to afford the title compound as a pale yellow oil.

LC-MS Rt 1.43 min [M+H]+ 275.9/277.9/279.9/281.9 (Method 2minLowpHv03)

Step 2: 2-Bromo-4-chlorothiazole nBuLi (2.5M in hexanes, 7.21 mL, 18.03 mmol) was added dropwise over 20 mins to 2,5-dibromo-4-chlorothiazole (step 1) (5 g, 18.03 mmol) in THF (100 mL) at −90° C. and the mixture stirred at −90° C. for 30 mins. Water (0.341 mL, 18.93 mmol) in THF (2 mL) was added and the mixture stirred whilst slowly warming to room temperature. The reaction mixture was quenched with 0.1M HCl(aq) (100 mL) and extracted with Et₂O (150 ml). The organic phase was washed with saturated NaHCO₃(aq) (100 mL) and water (100 mL), dried over magnesium sulphate and evaporated under vacuo to afford the product as a pale yellow oil which slowly crystallised as pale yellow needles.

1H NMR: (400 MHz, CDCl3) δ 7.09 (1H, s).

LC-MS: Rt 1.12 mins [M+H]+ 199.9 (Method 2minLowpHv03)

Step 3: 4-Chlorothiazole-2-carbaldehyde n-Butyllithium (1.732 ml, 2.77 mmol) was added dropwise over 20 mins to a solution of 2-bromo-4-chlorothiaole (step 2) (500 mg, 2.52 mmol) in diethyl ether (25.200 ml) at −78°. The mixture was stirred at −78° C. for 20 mins and treated with DMF (0.215 ml, 2.77 mmol) and the mixture warmed to −35° C. over 40 mins. The reaction was quenched with 6M HCl and the phases separated. The aqueous phase was extracted with diethyl ether (20 ml). The pH of the aqueous layer was adjusted to pH10 by addition of solid potassium carbonate at 5° C. and extracted with diethyl ether (3×35 ml). The combined organic extracts were dried over magnesium sulfate and evaporated under vacuum. Purification by chromatography on silica, eluting with hexane, afforded the title compound.

1H NMR (400 MHz, CDCl3) δ 9.98 (1H, s), 7.59 (1H, s).

Intermediate I 5-(4-(((4-Methoxybenzyl)oxy)methyl)thiazol-2-yl)-1,3-dimethyl-1H-pyrrolo[3,4-d]pyrimidine-2,4(3H,6H)-dione

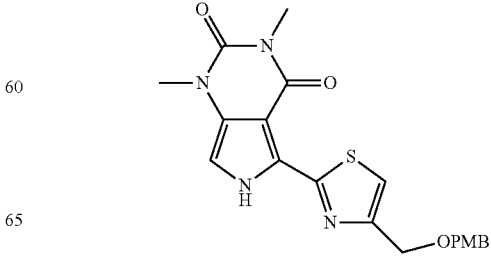

Step 1: Ethyl 2-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)thiazole-4-carboxylate The title compound was prepared analogously to 3-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile (Intermediate Ga, step 3) from 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (Intermediate Ga Step 2) and commercially available ethyl 2-bromothiazole-4-carboxylate.

1H NMR (400 MHz, DMSO-d6) δ 8.64 (1H, s), 7.33 (1H, s), 5.94 (2H, s), 4.33 (2H, q), 3.44 (2H, t), 3.34 (3H, s), 3.24 (3H, s), 1.32 (3H, t), 0.75 (2H, t), −0.15 (9H, s)

LC-MS Rt 1.55 mins [M+H]+ 465.3 (Method 2minLowpHv03)

Step 2: 5-(4-(Hydroxymethyl)thiazol-2-yl)-1,3-dimethyl-6-((2-(trimethylsilyl)ethoxy)methyl)-1H-pyrrolo[3,4-d]pyrimidine-2,4(3H,6H)-dione Sodium borohydride (0.856 g, 22.62 mmol) was added to a solution of ethyl 2-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)thiazole-4-carboxylate (step 1) (5.254 g, 11.31 mmol) and lithium chloride (0.959 g, 22.62 mmol) in ethanol (145 ml) and THF (290 ml) at 0° C. The mixture was stirred at room temperature for 16 hours. Further portions of lithium chloride (0.959 g, 22.62 mmol) and sodium borohydride (0.856 g, 22.62 mmol) were added and the mixture stirred for a further 4 hours. The reaction was quenched with saturated NaHCO$_3$ (aq) (250 ml), diluted with water (100 ml) and extracted with chloroform (3×350 ml). The combined organic extracts were washed with water (200 ml) and brine (2×200 ml), dried over sodium sulfate and evaporated under vacuum to afford the title compound.

1H NMR (400 MHz, DMSO-d6) δ 7.60 (1H, s), 7.23 (1H, s), 5.80 (2H, s), 5.38 (1H, t), 4.63 (2H, dd), 3.37 (2H, m), 3.33 (3H, s), 3.22 (3H, s), 0.73 (2H, m), −0.12 (9H, s).

LC-MS Rt 1.28 mins [M+H]+ 423.2 (Method 2minLowpHv03)

Step 3: A mixture of 5-(4-(((4-methoxybenzyl)oxy)methyl)thiazol-2-yl)-1,3-dimethyl-6-((2-(trimethylsilyl)ethoxy)methyl)-1H-pyrrolo[3,4-d]pyrimidine-2,4(3H,6H)-dione and 5-(4-(((4-methoxybenzyl)oxy)methyl)thiazol-2-yl)-1,3-dimethyl-1H-pyrrolo[3,4-d]pyrimidine-2,4(3H,6H)-dione Sodium hydride (60% wt, 0.637 g, 15.93 mmol) was added portionwise to a solution of 5-(4-(hydroxymethyl)thiazol-2-yl)-1,3-dimethyl-6-((2-(trimethylsilyl)ethoxy)methyl)-1H-pyrrolo[3,4-d]pyrimidine-2,4(3H,6H)-dione (step 2) (4.43 g, 7.97 mmol) in NMP (44 ml) at 0° C. and stirred for 1 hour. para-Methoxybenzyl chloride (1.404 ml, 10.36 mmol) was added and the mixture stirred at room temperature for 5 hours. Further portions of para-methoxybenzyl chloride (220 µl) and sodium hydride (60% wt, 64 mg) were added and the mixture stirred for a further 16 hours. The reaction was quenched at 0° C. with saturated NaHCO$_3$(aq) (50 ml), diluted with water (200 ml) and EtOAc (100 ml) and the phases separated. The aqueous phase was extracted with EtOAc (3×100 ml). The combined organic extracts were washed with water (2×100 ml) and brine (100 ml), dried over sodium sulfate and evaporated under vacuum. Purification by chromatography on silica, eluting with 40-60% EtOAc/hexane afforded the title mixture of compounds which was used in the next step without further purification.

Step 5: 5-(4-(((4-Methoxybenzyl)oxy)methyl)thiazol-2-yl)-1,3-dimethyl-1H-pyrrolo[3,4-d]pyrimidine-2,4(3H,6H)-dione tetra-n-Butylammonium fluoride solution (1.0 M in THF, 48.3 ml, 48.3 mmol) was added to a solution of 5-(4-(((4-methoxybenzyl)oxy)methyl)thiazol-2-yl)-1,3-dimethyl-6-((2-(trimethylsilyl)ethoxy)methyl)-1H-pyrrolo[3,4-d]pyrimidine-2,4(3H,6H)-dione and 5-(4-(((4-methoxybenzyl)oxy)methyl)thiazol-2-yl)-1,3-dimethyl-1H-pyrrolo[3,4-d]pyrimidine-2,4(3H,6H)-dione (step 4) (5.24 g) in THF (13.91 ml) at 60° C. After stirring at 60° C. for 6 hours, the mixture was cooled to room temperature and evaporated under vacuum. The residue was partitioned between EtOAc (100 ml) and water (150 ml) and the phases were separated. The organic phase was washed with water (3×200 ml) and both phases were allowed to stand for 60 hours. Both phases were filtered and the solids dried under vacuum to afford the title compound.

1H NMR (400 MHz, DMSO-d6) δ 12.79 (1H, s), 7.76 (1H, s), 7.45 (2H, d), 7.12-7.05 (3H, m), 4.77 (2H, s), 4.68 (2H, s), 3.90 (3H, s), 3.48 (3H, s), 3.40 (3H, s)

LC-MS Rt 1.24 mins [M+H]+ 413.5 (Method 2minLowpHv03)

The invention claimed is:
1. A compound of formula (I), or a pharmaceutically acceptable salt thereof:

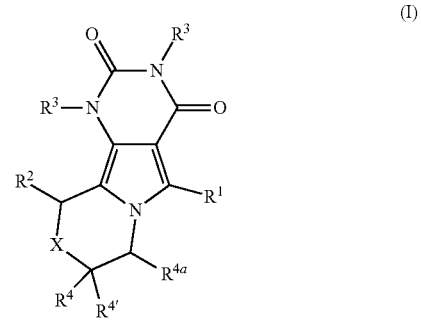

wherein $R^1$ represents phenyl, $(C_4-C_7)$cycloalkenyl or Het$^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1-C_4)$alkyl, halo, halo$(C_1-C_4)$alkyl, cyano, hydroxy$(C_1-C_4)$alkyl, $(C_1-C_4)$alkoxy, halo$(C_1-C_4)$alkoxy, $(C_1-C_4)$alkoxy$(C_1-C_4)$alkyl-, $R^6OC(O)$—, or $R^6OC(O)(C_1-C_4)$alkyl-;

$R^{a1}$ represents $(C_1-C_4)$alkyl, hydroxy$(C_1-C_4)$alkyl, $(C_1-C_4)$alkoxy$(C_1-C_4)$alkyl-, $(C_1-C_4)$alkylamino$(C_1-C_4)$alkyl-, di[$(C_1-C_4)$alkyl]amino$(C_1-C_4)$alkyl-, aryl$(C_1-C_4)$alkyl- or $R^6OC(O)(C_1-C_4)$alkyl-;

$R^2$ represents $(C_1-C_6)$alkyl, $(C_3-C_7)$cycloalkyl, $(C_4-C_7)$cycloalkenyl, phenyl, furanyl, thiazolyl, thienyl or pyrazolyl, which $R^2$ may be unsubstituted or substituted on from one to three carbon atoms with substituents $R^b$, and may further be substituted on a nitrogen atom with $(C_1-C_4)$alkyl;

each $R^b$ independently represents $(C_1-C_4)$alkyl, halo, halo$(C_1-C_4)$alkyl, cyano, $(C_1-C_4)$alkylamino$(C_1-C_4)$alkyl-, di[$(C_1-C_4)$alkyl]amino$(C_1-C_4)$alkyl-, $(R^6)_2NC(O)(C_1-C_4)$alkyl- or $R^6OC(O)(C_1-C_4)$alkyl-;

X represents O, NH or NCH$_3$; or

X represents —CH$_2$—O—, wherein the O atom is attached to the —C($R^{4'}$)($R^{4'}$) atom of the ring;

each $R^3$ independently represents methyl or ethyl;

$R^4$ represents hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, phenyl, Het$^1$$(C_1-C_4)$alkyl-, Het$^2$$(C_1-C_4)$alkyl-, $(C_1-C_4)$alkylS(O)$_2$NH$(C_1-C_4)$alkyl-, or $R^7C(O)NH(C_1-C_4)$alkyl-;

$R^{4'}$ represents hydrogen or methyl;

$R^{4a}$ represents hydrogen, $(C_1-C_4)$alkyl, halo$(C_1-C_4)$alkyl, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, Het$^1$$(C_1-C_4)$alkyl-, Het$^2$$(C_1-C_4)$alkyl-, or $R^6OC(O)$—;

$R^6$ represents hydrogen or $(C_1-C_4)$alkyl;

$R^7$ represents $(C_1-C_2)$alkyl, $(C_1-C_2)$alkoxy, $(C_1-C_2)$alkoxy$(C_1-C_2)$alkyl or phenyl;

Het$^1$ represents a 5- or 6-membered heteroaryl ring comprising a) one oxygen or sulphur atom and optionally one or two nitrogen atoms; or b) from one to four nitrogen atoms; and Het$^2$ represents a 4- to 7-membered heterocyclyl ring comprising a) 1 or 2 heteroatoms selected from nitrogen, oxygen and sulphur; or b) —C(O)— and 1 or 2 heteroatoms selected from nitrogen and oxygen.

2. The A compound according to claim 1, wherein the compound is of formula (Ia):

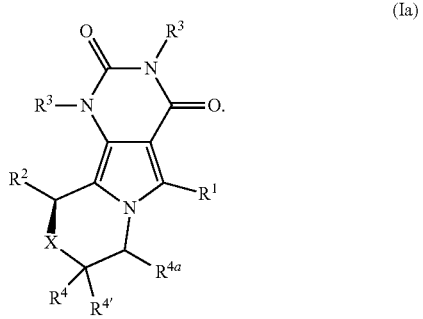

(Ia)

3. The compound according to claim 1, wherein X represents O.

4. The compound according to claim 1, wherein $R^1$ represents phenyl, cyclohexenyl, thiazolyl, pyrazolyl, thienyl, pyrimidin-2-yl or pyridin-2-yl and wherein $R^1$ may be unsubstituted or substituted on one or two carbon atoms by substituents $R^a$, and may further be substituted on a nitrogen atom with a substituent $R^{a1}$.

5. The compound according to claim 1, wherein each $R^a$ independently represents $(C_1-C_4)$alkyl, halo, halo$(C_1-C_4)$alkyl, cyano, $(C_1-C_4)$alkoxy, $R^6OC(O)$—, or $R^6OC(O)(C_1-C_4)$alkyl-.

6. The compound according to claim 1, wherein $R^2$ represents phenyl, furanyl, thiazolyl, thienyl or pyrazolyl, which $R^2$ may be unsubstituted or substituted on from one to three carbon atoms with substituents $R^b$, and may further be substituted on a nitrogen atom with $(C_1-C_4)$alkyl.

7. The compound according to claim 1, wherein each $R^b$ independently represents $(C_1-C_2)$alkyl, halo, halo$(C_1-C_2)$alkyl, or cyano.

8. The compound according to claim 1, wherein each $R^3$ represents methyl.

9. The compound according to claim 1, wherein $R^4$ represents hydrogen, methyl, phenyl or —CH$_2$OH.

10. The compound according to claim 1, wherein the compound is selected from the group consisting of:

1,3-Dimethyl-10-(5-methylfuran-2-yl)-5-phenyl-7,8,9,10-tetrahydropyrazino[1',2':1,2]pyrrolo[3,4-d]pyrimidine-2,4(1H,3H)-dione;

10-(5-chlorofuran-2-yl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione;

10-(4-Bromothiazol-2-yl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-5-phenyl-10-(thiazol-2-yl)-7,8,9,10-tetrahydropyrazino[1',2':1,2]pyrrolo[3,4-d]pyrimidine-2,4(1H,3H)-dione;

1,3-Dimethyl-10-(4-methylthiophen-2-yl)-5-phenyl-7,8,9,10-tetrahydropyrazino[1',2':1,2]pyrrolo[3,4-d]pyrimidine-2,4(1H,3H)-dione;

1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione;

10-(5-Ethylfuran-2-yl)-1,3-dimethyl-5-phenyl-7,8,9,10-tetrahydropyrazino[1',2':1,2]pyrrolo[3,4-d]pyrimidine-2,4(1H,3H)-dione;

5-(4-Fluorophenyl)-1,3-dimethyl-10-(5-methylfuran-2-yl)-7,8,9,10-tetrahydropyrazino[1',2':1,2]pyrrolo[3,4-d]pyrimidine-2,4(1H,3H)-dione;

1,3-Dimethyl-10-(1-methyl-1H-pyrazol-3-yl)-5-phenyl-7,8,9,10-tetrahydropyrazino[1',2':1,2]pyrrolo[3,4-d]pyrimidine-2,4(1H,3H)-dione;

1,3-Dimethyl-10-(5-methylthiophen-2-yl)-5-phenyl-7,8,9,10-tetrahydropyrazino[1',2':1,2]pyrrolo[3,4-d]pyrimidine-2,4(1H,3H)-dione;

10-(2,3-Difluorophenyl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-5,10-diphenyl-7,8,9,10-tetrahydropyrazino[1',2':1,2]pyrrolo[3,4-d]pyrimidine-2,4(1H,3H)-dione;

10-(5-Chlorofuran-2-yl)-1,3-dimethyl-5-(m-tolyl)-7,8,9,10-tetrahydropyrazino[1',2':1,2]pyrrolo[3,4-d]pyrimidine-2,4(1H,3H)-dione;

10-(Cyclohex-3-en-1-yl)-1,3-dimethyl-5-phenyl-7,8,9,10-tetrahydropyrazino[1',2':1,2]pyrrolo[3,4-d]pyrimidine-2,4(1H,3H)-dione;

10-(4-Bromofuran-2-yl)-1,3-dimethyl-5-phenyl-7,8,9,10-tetrahydropyrazino[1',2':1,2]pyrrolo[3,4-d]pyrimidine-2,4(1H,3H)-dione;

3-(1,3-Dimethyl-2,4-dioxo-5-phenyl-1,2,3,4,7,8,9,10-octahydropyrazino[1',2':1,2]pyrrolo[3,4-d]pyrimidin-10-yl)benzonitrile;

10-(furan-2-yl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-10-(2-methylthiazol-4-yl)-5-phenyl-7,8,9,10-tetrahydropyrazino[1',2':1,2]pyrrolo[3,4-d]pyrimidine-2,4(1H,3H)-dione;

10-(4-Fluorophenyl)-1,3-dimethyl-5-phenyl-7,8,9,10-tetrahydropyrazino[1',2':1,2]pyrrolo[3,4-d]pyrimidine-2,4(1H,3H)-dione;

10-(4-Chlorophenyl)-1,3-dimethyl-5-phenyl-7,8,9,10-tetrahydropyrazino[1',2':1,2]pyrrolo[3,4-d]pyrimidine-2,4(1H,3H)-dione;

3-(10-(5-Chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile;

3-(1,3-Dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile;

10-(5-Chlorofuran-2-yl)-1,3-dimethyl-5-(4-methylthiazol-2-yl)-7,8,9,10-tetrahydropyrazino[1',2':1,2]pyrrolo[3,4-d]pyrimidine-2,4(1H,3H)-dione;

1,3-Dimethyl-10-(4-methylthiazol-2-yl)-5-phenyl-7,8,9,10-tetrahydropyrazino[1',2':1,2]pyrrolo[3,4-d]pyrimidine-2,4(1H,3H)-dione;

10-(3-chlorophenyl)-1,3-dimethyl-5-phenyl-7,8,9,10-tetrahydropyrazino[1',2':1,2]pyrrolo[3,4-d]pyrimidine-2,4(1H,3H)-dione;

10-(5-Ethylfuran-2-yl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-5-phenyl-10-(4-(trifluoromethyl)thiazol-2-yl)-7,8,9,10-tetrahydropyrazino[1',2':1,2]pyrrolo[3,4-d]pyrimidine-2,4(1H,3H)-dione;

10-(2,3-Difluorophenyl)-1,3-dimethyl-5-phenyl-7,8,9,10-tetrahydropyrazino[1',2':1,2]pyrrolo[3,4-d]pyrimidine-2,4(1H,3H)-dione;

10-Cyclohexyl-1,3-dimethyl-5-phenyl-7,8,9,10-tetrahydropyrazino[1',2':1,2]pyrrolo[3,4-d]pyrimidine-2,4(1H,3H)-dione;

10-(Furan-2-yl)-1,3-dimethyl-5-phenyl-7,8,9,10-tetrahydropyrazino[1',2':1,2]pyrrolo[3,4-d]pyrimidine-2,4(1H,3H)-dione;

1,3-Dimethyl-5,10-diphenyl-7,8,9,10-tetrahydropyrazino[1',2':1,2]pyrrolo[3,4-d]pyrimidine-2,4(1H,3H)-dione;

3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzonitrile;

3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzonitrile;

10-(5-Chlorofuran-2-yl)-5-(3-chlorophenyl)-1,3-dimethyl-7,8,9,10-tetrahydropyrazino[1',2':1,2]pyrrolo[3,4-d]pyrimidine-2,4(1H,3H)-dione;

5-(3-Chlorophenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

5-(3-Methoxyphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

10-(5-Chlorofuran-2-yl)-5-(3-methoxyphenyl)-1,3-dimethyl-7,8,9,10-tetrahydropyrazino[1',2':1,2]pyrrolo[3,4-d]pyrimidine-2,4(1H,3H)-dione;

5-(3,5-Dimethylphenyl)-1,3-dimethyl-10-(4-methylthiazol-2-yl)-7,8,9,10-tetrahydropyrazino[1',2':1,2]pyrrolo[3,4-d]pyrimidine-2,4(1H,3H)-dione;

10-(5-Chlorofuran-2-yl)-5-(3,5-dimethylphenyl)-1,3-dimethyl-7,8,9,10-tetrahydropyrazino[1',2':1,2]pyrrolo[3,4-d]pyrimidine-2,4(1H,3H)-dione;

Methyl 3-(10-(5-chlorofuran-2-yl)-1,3-dimethyl-2,4-dioxo-1,2,3,4,7,8,9,10-octahydropyrazino[1',2':1,2]pyrrolo[3,4-d]pyrimidin-5-yl)benzoate;

Methyl 3-(1,3-dimethyl-10-(4-methylthiazol-2-yl)-2,4-dioxo-1,2,3,4,7,8,9,10-octahydropyrazino[1',2':1,2]pyrrolo[3,4-d]pyrimidin-5-yl)benzoate;

10-(5-Chlorofuran-2-yl)-1,3-dimethyl-5-(3-(trifluoromethyl)phenyl)-7,8,9,10-tetrahydropyrazino[1',2':1,2]pyrrolo[3,4-d]pyrimidine-2,4(1H,3H)-dione;

1,3-Dimethyl-10-(5-methylfuran-2-yl)-5-phenyl-7,8-dihydro-1H-pyrimido[4',5':3,4]pyrrolo[2,1-c][1,4]oxazine-2,4(3H,10H)-dione;

10-(5-Bromofuran-2-yl)-1,3-dimethyl-5-phenyl-7,8-dihydro-1H-pyrimido[4',5':3,4]pyrrolo[2,1-c][1,4]oxazine-2,4(3H,10H)-dione;

1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione;

10-(3-Chlorophenyl)-1,3-dimethyl-5-(m-tolyl)-7,8-dihydro-1H-pyrimido[4',5':3,4]pyrrolo[2,1-c][1,4]oxazine-2,4(3H,10H)-dione;

1,3-Dimethyl-10-(4-methylthiazol-2-yl)-5-(m-tolyl)-7,8-dihydro-1H-pyrimido[4',5':3,4]pyrrolo[2,1-c][1,4]oxazine-2,4(3H,10H)-dione;

1,3,7-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione;

10-(5-Chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]oxazine-2,4(3H,10H)-dione;

10-(5-Chlorofuran-2-yl)-8-(hydroxymethyl)-5-(4-(hydroxymethyl)thiazol-2-yl)-1,3-dimethyl-7,8-dihydro-1H-pyrimido[4',5':3,4]pyrrolo[2,1-c][1,4]oxazine-2,4(3H,10H)-dione;

10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione;

10-(4-Chlorothiazol-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]oxazine-2,4(3H,10H)-dione;

5-(3-Chlorophenyl)-10-(4-chlorothiazol-2-yl)-8-(hydroxymethyl)-1,3-dimethyl-7,8-dihydro-1H-pyrimido[4',5':3,4]pyrrolo[2,1-c][1,4]oxazine-2,4(3H,10H)-dione;

10-(5-Chlorofuran-2-yl)-5-(3-chlorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]oxazin-5-yl)benzonitrile;

10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]oxazine-2,4(3H,10H)-dione;

10-(5-Chlorofuran-2-yl)-8-(hydroxymethyl)-1,3-dimethyl-5-phenyl-7,8,9,10-tetrahydropyrazino[1',2':1,2]pyrrolo[3,4-d]pyrimidine-2,4(1H,3H)-dione;

1,3,8-trimethyl-10-(4-methylthiazol-2-yl)-5-phenyl-7,8-dihydro-1H-pyrimido[4',5':3,4]pyrrolo[2,1-c][1,4]oxazine-2,4(3H,10H)-dione;

10-(5-chlorofuran-2-yl)-1,3,8-trimethyl-5-(m-tolyl)-7,8-dihydro-1H-pyrimido[4',5':3,4]pyrrolo[2,1-c][1,4]oxazine-2,4(3H,10H)-dione;

10-(5-chlorofuran-2-yl)-5-(3-chlorophenyl)-8-(methoxymethyl)-1,3-dimethyl-7,8-dihydro-1H-pyrimido[4',5':3,4]pyrrolo[2,1-c][1,4]oxazine-2,4(3H,10H)-dione;

10-(5-chlorofuran-2-yl)-1,3-dimethyl-5,8-diphenyl-7,8-dihydro-1H-pyrimido[4',5':3,4]pyrrolo[2,1-c][1,4]oxazine-2,4(3H,10H)-dione;

10-(5-chlorofuran-2-yl)-5-(3-chlorophenyl)-8-((dimethylamino)methyl)-1,3-dimethyl-7,8-dihydro-1H-pyrimido[4',5':3,4]pyrrolo[2,1-c][1,4]oxazine-2,4(3H,10H)-dione;

10-(5-Chlorofuran-2-yl)-1,3,8,8-tetramethyl-5-phenyl-7,8-dihydro-1H-pyrimido[4',5':3,4]pyrrolo[2,1-c][1,4]oxazine-2,4(3H,10H)-dione;

11-(4-Chlorothiazol-2-yl)-1,3-dimethyl-5-phenyl-7,8,10,11-tetrahydropyrimido[4',5':3,4]pyrrolo[1,2-d][1,4]oxazepine-2,4(1H,3H)-dione;

3-(11-(4-chlorothiazol-2-yl)-8-(hydroxymethyl)-1,3-dimethyl-2,4-dioxo-1,2,3,4,7,8,10,11-octahydropyrimido[4',5':3,4]pyrrolo[1,2-d][1,4]oxazepin-5-yl)benzonitrile;

8-((1H-Imidazol-1-yl)methyl)-10-(5-chlorofuran-2-yl)-5-(3-fluorophenyl)-1,3-dimethyl-7,8-dihydro-1H-pyrimido[4',5':3,4]pyrrolo[2,1-c][1,4]oxazine-2,4(3H,10H)-dione; and (5-Chlorofuran-2-yl)-1,3-di methyl-5-(4-methylthiazol-2-yl)-8-((2-oxopyrrolidin-1-yl)methyl)-7,8-dihydro-1H-pyrimido[4',5':3,4]pyrrolo[2,1-c][1,4]oxazine-2,4(3H,10H)-dione; or a pharmaceutically acceptable salt thereof.

11. A pharmaceutical composition comprising a therapeutically effective amount of a compound according to claim 1 or a pharmaceutically acceptable salt thereof and one or more pharmaceutically acceptable carriers.

12. A pharmaceutical composition comprising a therapeutically effective amount of a compound according to claim 2 or a pharmaceutically acceptable salt thereof and one or more pharmaceutically acceptable carriers.

13. A pharmaceutical composition comprising a therapeutically effective amount of a compound according to claim 10 or a pharmaceutically acceptable salt thereof and one or more pharmaceutically acceptable carriers.

14. A combination comprising a therapeutically effective amount of a compound according to claim 1 or a pharmaceutically acceptable salt thereof and one or more therapeutically active co-agents.

15. A combination comprising a therapeutically effective amount of a compound according to claim 2 or a pharmaceutically acceptable salt thereof and one or more therapeutically active co-agents.

16. A combination comprising a therapeutically effective amount of a compound according to claim 10 or a pharmaceutically acceptable salt thereof and one or more therapeutically active co-agents.

17. A method of modulating cystic fibrosis transmembrane conductance regulator activity in a subject, comprising administering to the subject a therapeutically effective amount of the compound according to claim 1 or a pharmaceutically acceptable salt thereof.

18. A method of modulating cystic fibrosis transmembrane conductance regulator activity in a subject, administering to the subject a therapeutically effective amount of the compound according to claim 2 or a pharmaceutically acceptable salt thereof.

19. A method of modulating cystic fibrosis transmembrane conductance regulator activity in a subject, administering to the subject a therapeutically effective amount of the compound according to claim 10 or a pharmaceutically acceptable salt thereof.

20. A method of treating polycystic kidney disease or diarrhea, comprising administering to the subject a therapeutically effective amount of the compound according to claim 1 or a pharmaceutically acceptable salt thereof.

21. A method of treating polycystic kidney disease or diarrhea, comprising administering to the subject a therapeutically effective amount of the compound according to claim 2 or a pharmaceutically acceptable salt thereof.

22. A method of treating polycystic kidney disease or diarrhea, comprising administering to the subject a therapeutically effective amount of the compound according to claim 10 or a pharmaceutically acceptable salt thereof.

* * * * *